United States Patent
Chen et al.

(10) Patent No.: US 10,745,746 B2
(45) Date of Patent: Aug. 18, 2020

(54) SPECIFIC NUCLEIC ACID AMPLIFICATION WITH COMPOUNDED SELECTIVITY

(71) Applicant: President and Fellows of Harvard College, Cambridge, MA (US)

(72) Inventors: Xi Chen, Newton, MA (US); David Yu Zhang, Houston, TX (US); Peng Yin, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 722 days.

(21) Appl. No.: 14/905,021

(22) PCT Filed: Jul. 18, 2014

(86) PCT No.: PCT/US2014/047196
§ 371 (c)(1),
(2) Date: May 26, 2016

(87) PCT Pub. No.: WO2015/010020
PCT Pub. Date: Jan. 22, 2015

(65) Prior Publication Data
US 2016/0153036 A1 Jun. 2, 2016

Related U.S. Application Data

(60) Provisional application No. 61/856,028, filed on Jul. 18, 2013.

(51) Int. Cl.
*C12Q 1/6858* (2018.01)
*C12Q 1/6848* (2018.01)
*C12N 1/00* (2006.01)

(52) U.S. Cl.
CPC ......... *C12Q 1/6858* (2013.01); *C12Q 1/6848* (2013.01)

(58) Field of Classification Search
CPC ............ C12Q 1/6848; C12Q 2525/161; C12Q 2525/197; C12Q 2537/1376; C12Q 1/6858
See application file for complete search history.

(56) References Cited

U.S. PATENT DOCUMENTS 5,436,149 A 7/1995 Barnes
8,815,514 B2 8/2014 Satterfield et al.
(Continued)

FOREIGN PATENT DOCUMENTS

WO WO 02/22882 A2 3/2002
WO WO 03/095664 A2 11/2003
(Continued)

OTHER PUBLICATIONS

Chun et al., Dual priming oligonucleotide system for the multiplex detection of respiratory viruses and SNP genotyping of CYP2C19 gene Nucl. Acids Res., vol. 35, e40, pp. 1-6, (Year: 2007).*
(Continued)

*Primary Examiner* — Teresa E Strzelecka
(74) *Attorney, Agent, or Firm* — Wolf, Greenfield & Sacks, P.C.

(57) ABSTRACT

The present disclosure provides, in various aspects and embodiments, methods and compositions for selectively amplifying a rare target nucleic acid and/or suppressing amplification of non-target nucleic acids with sequences similar to the rare target nucleic acid. The methods and composition are useful, for example, for detecting rare alleles among a population of wild-type alleles.

12 Claims, 18 Drawing Sheets

Specification includes a Sequence Listing.

(56) References Cited

U.S. PATENT DOCUMENTS

| | | | |
|---|---|---|---|
| 9,284,602 | B2 | 3/2016 | Zhang et al. |
| 9,862,994 | B2 | 1/2018 | Schmidt et al. |
| 2012/0035065 | A1 | 2/2012 | Smolke et al. |
| 2012/0171673 | A1* | 7/2012 | Nakamura ............ C12Q 1/6809 435/6.11 |
| 2013/0072390 | A1 | 3/2013 | Wang et al. |
| 2013/0274135 | A1 | 10/2013 | Zhang et al. |
| 2014/0066610 | A1 | 3/2014 | Schaus et al. |
| 2015/0024972 | A1 | 1/2015 | Schmidt et al. |
| 2015/0152491 | A1 | 6/2015 | Zhang et al. |
| 2018/0094309 | A1 | 4/2018 | Chen et al. |

FOREIGN PATENT DOCUMENTS

| | | |
|---|---|---|
| WO | WO 2004/044549 A2 | 5/2004 |
| WO | WO 2007/106534 A2 | 9/2007 |
| WO | WO 2008/104794 A2 | 9/2008 |
| WO | WO 2010/120853 A2 | 10/2010 |
| WO | WO 2012/058488 A1 | 5/2012 |
| WO | WO 2012/149154 A1 | 11/2012 |
| WO | WO 2014/014988 A2 | 1/2014 |
| WO | WO 2015/010020 A1 | 1/2016 |
| WO | WO 2017/205719 A1 | 11/2017 |

OTHER PUBLICATIONS

Cha et al., Mismatch amplification mutation assay (MAMA): application to the c-H-ras gene. PCR Methods Appl. Aug. 1992;2(1):14-20.

Dirks et al., Triggered amplification by hybridization chain reaction. PNAS. Oct. 2004;101(43): 15275-78.

Dobosy et al., RNase H-dependent PCR (rhPCR): improved specificity and single nucleotide polymorphism detection using blocked cleavable primers. BMC Biotechnol. Aug. 10, 2011;11:80. doi:10.1186/1472-6750-11-80. 18 pages.

Gevensleben et al., Noninvasive detection of HER2 amplification with plasma DNA digital PCR. Clin Cancer Res. Jun. 15, 2013;19(12):3276-84. doi:10.1158/1078-0432.CCR-12-3768. Epub May 1, 2013.

Kinde et al., Detection and quantification of rare mutations with massively parallel sequencing. Proc Natl Acad Sci U S A. Jun. 7, 2011;108(23):9530-5. doi: 10.1073/pnas.1105422108. Epub May 17, 2011.

Li et al., Replacing PCR with Cold-PCR enriches variant DNA sequences and redefines the sensitivity of genetic testing. Nat Med. May 2008;14(5):579-84. doi: 10.1038/nm1708. Epub Apr. 13, 2008.

Li et al., A new class of homogeneous nucleic acid probes based on specific displacement hybridization. Nucleic Acids Research. 2002;30(2):e5:1-9.

Liu et al., Pyrophosphorolysis-activated polymerization (PAP): application to allele-specific amplification. Biotechniques. Nov. 2000;29(5):1072-6, 1078, 1080 passim.

Lizardi et al., Mutation detection and single-molecule counting using isothermal rolling-circle amplification. Nat Genet. Jul. 1998;19(3):225-32.

Milbury et al., Multiplex amplification coupled with Cold-PCR and high resolution melting enables identification of low-abundance mutations in cancer samples with low DNA content. J Mol Diagn. Mar. 2011;13(2):220-32. doi: 10.1016/j.jmoldx.2010.10.008.

Milbury et al., PCR-based methods for the enrichment of minority alleles and mutations. Clin Chem. Apr. 2009;55(4):632-40. doi:10.1373/clinchem.2008.113035. Epub Feb. 6, 2009.

Morandi et al., Allele specific locked nucleic acid quantitative PCR (ASLNAqPCR):an accurate and cost-effective assay to diagnose and quantify KRAS and BRAF mutation. PLoS One. 2012;7(4):e36084. doi: 10.1371/journal.pone.0036084. Epub Apr. 30, 2012.

Morlan et al., Mutation detection by real-time PCR: a simple, robust and highly selective method. PLoS One. 2009;4(2):e4584. doi:10.1371/journal.pone.0004584. Epub Feb. 25, 2009.

Newman at al., An ultrasensitive method for quantitating circulating tumor DNA with broad patient coverage. Nat Med. May 2014;20(5):548-54. doi: 10.1038/nm.3519. Author Manuscript. Epub Apr. 6, 2014.

Newton et al., Analysis of any point mutation in DNA. The amplification refractory mutation system (ARMS). Nucleic Acids Res. Apr. 11, 1989;17(7):2503-16.

Orum et al., Single base pair mutation analysis by PNA directed PCR clamping. Nucleic Acids Res. Nov. 25, 1993;21(23):5332-6.

Satterfield, Technical Advance. Cooperative primers—2.5 million—fold improvement in the reduction of nonspecific amplification. J Mol Diag. Mar. 2014;16(2):163-173.

Seyama et al., A novel blocker-PCR method for detection of rare mutant alleles in the presence of an excess amount of normal DNA. Nucleic Acids Res. May 25, 1992;20(10):2493-6.

Yurke et al., A DNA-fuelled molecular machine made of DNA. Nature. Aug. 10, 2000;406(6796):605-8.

Zhang et al., Optimizing the specificity of nucleic acid hybridization. Nat Chem. Jan. 22, 2012;4(3):208-14. doi: 10.1038/nchem.1246. 7 pages.

Zhang et al., Robustness and modularity properties of a non-covalent DNA catalytic reaction. Nucleic Acids Res. Jul. 2010;38(12):4182-97. doi:10.1093/nar/gkq088. Epub Mar. 1, 2010.

Zhou et al., Enrichment and detection of rare alleles by means of snapback primers and rapid-cycle PCR. Clin Chem. May 2010;56(5):814-22. doi: 10.1373/clinchem.2009.142034. Epub Mar. 18, 2010.

Zhou et al., Rare allele enrichment and detection by allele-specific PCR, competitive probe blocking, and melting analysis. BioTechniques. May 2011; 50(5): 311-318.

Genot et al., Remote Toehold: A Mechanism for Flexible Control of DNA Hybridization Kinetics. J. Am. Chem. Soc. 2011:133(7):2177-82.

Zhang et al., Control of DNA strand displacement kinetics using toehold exchange. J Am Chem Soc. Dec. 2, 2009;131(47):17303-14.

Zhang et al., Dynamic DNA nanotechnology using strand-displacement reactions. Nat Chem. Feb. 2011;3(2):103-13. doi: 10.1038/nchem.957.

* cited by examiner

Below Tm    Above Tm

SEQUENCE LISTING

```
<160> NUMBER OF SEQ ID NOS: 57

<210> SEQ ID NO 1
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 1
ttcatcagtg atcaccgccc atccgacgct atttgtgccg atatctaagc ctattgagta     60
tttc                                                                  64

<210> SEQ ID NO 2
<211> LENGTH: 64
<212> TYPE: DNA
<213> ORGANISM: Artificial Sequence
```

<220> FEATURE:
<223> OTHER INFORMATION: Synthetic Polynucleotide

<400> SEQUENCE: 2
ttcatcagtg atcaccgccc atccgacgct atttgtgccg ctatctaagc ctattgagta     60
tttc                                                                 64

<210> SEQ ID NO 3
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 3
gcttagatat cggcacaaat agcgtcggat                                      30

<210> SEQ ID NO 4
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 4
gcttagatat cggcacaaat agcgtcggat gggcgtcttc ttca                      44

<210> SEQ ID NO 5
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 5
tgaagaagac gcccatccga cgctatttgt gc                                   32

<210> SEQ ID NO 6
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 6
gctatcggca caaatagcgt ttttttttat ggataagaaa tac                       43

<210> SEQ ID NO 7
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 7
accttatatt catcagtgat caccg                                           25

<210> SEQ ID NO 8
<211> LENGTH: 80
<212> TYPE: DNA
<213> ORGANISM: Artificial Sequence
<220> FEATURE:
<223> OTHER INFORMATION: Synthetic Polynucleotide

<400> SEQUENCE: 8

```
atggataaga aatactcaat aggcttagct atcggcacaa atagcgtcgg atgggcggtg    60
atcactgatg aatataaggt                                                80
```

<210> SEQ ID NO 9
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 9

```
atggataaga aatactttt tcaataggct tagctatcgg cacaaatagc gtcggatggg    60
cggtgatcac tgatgaatat aaggt                                          85
```

<210> SEQ ID NO 10
<211> LENGTH: 90
<212> TYPE: DNA
<213> ORGANISM: Artificial Sequence
<220> FEATURE:
<223> OTHER INFORMATION: Synthetic Polynucleotide

<400> SEQUENCE: 10

```
atggataaga aatactttt tttttcaat aggcttagct atcggcacaa atagcgtcgg    60
atgggcggtg atcactgatg aatataaggt                                     90
```

<210> SEQ ID NO 11
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 11

```
tttttttat ggataagaaa tac                                             23
```

<210> SEQ ID NO 12
<211> LENGTH: 66
<212> TYPE: DNA
<213> ORGANISM: Artificial Sequence
<220> FEATURE:
<223> OTHER INFORMATION: Synthetic Polynucleotide

<400> SEQUENCE: 12

```
ttgagaatgg attaagtcaa cctcatcttt atttttggg cgggccaaac ctctacttca    60
tacacc                                                               66
```

<210> SEQ ID NO 13
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 13

```
tgaggttgac ttaatccatt ctcaaaacgt actggtga                            38
```

<210> SEQ ID NO 14
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 14

```
ttgagaatgg attaagtcaa cctcatcttt attttttggg cgggccaaa        49
```

<210> SEQ ID NO 15
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 15

```
gcctggtccc tggtgtcagg aaa                                   23
```

<210> SEQ ID NO 16
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 16

```
caccagggac caggc                                            15
```

<210> SEQ ID NO 17
<211> LENGTH: 155
<212> TYPE: DNA
<213> ORGANISM: Artificial Sequence
<220> FEATURE:
<223> OTHER INFORMATION: Synthetic Polynucleotide

<400> SEQUENCE: 17

```
aacgtactgg tgaaaacacc gcagcatgtc aagatcacag attttgggct ggccaaactg    60
ctgggtgcgg aagagaaaga ataccatgca gaaggaggca agtaaggag gtggctttag    120 gtcagccagc attttcctga caccagggac caggc                               155
```

<210> SEQ ID NO 18
<211> LENGTH: 155
<212> TYPE: DNA
<213> ORGANISM: Artificial Sequence
<220> FEATURE:
<223> OTHER INFORMATION: Synthetic Polynucleotide

<400> SEQUENCE: 18

```
aacgtactgg tgaaaacacc gcagcatgtc aagatcacag attttgggcg ggccaaactg    60
ctgggtgcgg aagagaaaga ataccatgca gaaggaggca agtaaggag gtggctttag    120 gtcagccagc attttcctga caccagggac caggc                               155
```

<210> SEQ ID NO 19
<211> LENGTH: 170
<212> TYPE: DNA
<213> ORGANISM: Artificial Sequence
<220> FEATURE:
<223> OTHER INFORMATION: Synthetic Polynucleotide

<400> SEQUENCE: 19

```
aacgtactgg tgaaaacacc gcagcatgtc aagatcacag attttgggcg ggccaaactg    60
ctgggtgcgg aagagaaaga ataccatgca gaaggaggca agtaaggtt ttactttact    120 ttaaggtggc tttaggtcag ccagcatttt cctgacacca gggaccaggc              170
```

<210> SEQ ID NO 20
<211> LENGTH: 31
<212> TYPE: DNA

```
<213> ORGANISM: Artificial Sequence
<220> FEATURE:
<223> OTHER INFORMATION: Synthetic Polynucleotide

<400> SEQUENCE: 20
gaggcaaaaa tggataagaa atactcaata g                                  31

<210> SEQ ID NO 21
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 21
taagattttt tttgatactg tggcggtctg tatttcccag aaccttg                 47

<210> SEQ ID NO 22
<211> LENGTH: 151
<212> TYPE: DNA
<213> ORGANISM: Artificial Sequence
<220> FEATURE:
<223> OTHER INFORMATION: Synthetic Polynucleotide

<400> SEQUENCE: 22
taagattttt tttgatactg tggcggtctg tatttcccag aaccttgaac tttttagacg   60
gaaccttata ttcatcagtg atcaccgccc atccgacgct atttgtgccg atatctaagc  120
ctattgagta tttcttatcc atttttgcct c                                 151

<210> SEQ ID NO 23
<211> LENGTH: 151
<212> TYPE: DNA
<213> ORGANISM: Artificial Sequence
<220> FEATURE:
<223> OTHER INFORMATION: Synthetic Polynucleotide

<400> SEQUENCE: 23
taagattttt tttgatactg tggcggtctg tatttcccag aaccttgaac tttttagacg   60
gaaccttata ttcatcagtg atcaccgccc atccgacgct atttgtgccg atagctaagc  120
ctattgagta tttcttatcc atttttgcct c                                 151

<210> SEQ ID NO 24
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 24
gcttagatat cggcacaaat agcgtcggat gggcgtcttc ttcaaatcgg g            51

<210> SEQ ID NO 25
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 25
cccgatttga agaagacgcc catccgacgc tatt                              34

<210> SEQ ID NO 26
<211> LENGTH: 31
```

```
<212> TYPE: DNA
<213> ORGANISM: Artificial Sequence
<220> FEATURE:
<223> OTHER INFORMATION: Synthetic Polynucleotide

<400> SEQUENCE: 26
gaggcaaaaa tggataagaa atactcaata g                                    31

<210> SEQ ID NO 27
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 27
cagaaccttg aactttttag acgg                                            24

<210> SEQ ID NO 28
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 28
taagattttt tttgatactg tggcggtctg tatttcccag aaccttg                   47

<210> SEQ ID NO 29
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 29
accgccacag tatcaaaaaa aatctta                                         27

<210> SEQ ID NO 30
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 30
gcttagctat cggcacaaat agcgtcggat gggcgtcttc ttcaaatcgg g               51

<210> SEQ ID NO 31
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 31
ctcatcacgc agctcatgcc cttcggctgc ctcctggact cctgacaccg caaaa           55

<210> SEQ ID NO 32
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 32
```

```
cggtgtcagg agtccaggag gcagccgaag ggcatgaaaa a                    41
```

<210> SEQ ID NO 33
<211> LENGTH: 175
<212> TYPE: DNA
<213> ORGANISM: Artificial Sequence
<220> FEATURE:
<223> OTHER INFORMATION: Synthetic Polynucleotide

<400> SEQUENCE: 33

```
gctgggcatc tgcctcacct ccaccgtgca gctcatcatg cagctcatgc ccttcggctg    60
cctcctggac tatgtccggg aacaaatact tactattact tatacaaaga caatattggc   120
tcccagtacc tgctcaactg gtgtgtgcag atcgcaaagg taatcaggga aggga        175
```

<210> SEQ ID NO 34
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 34

```
tgcacggctc acctccaccg tgca                                        24
```

<210> SEQ ID NO 35
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 35

```
ctcaactgga tctgcacaca ccagttgag                                   29
```

<210> SEQ ID NO 36
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 36

```
tgcacggctc acctccaccg tgca                                        24
```

<210> SEQ ID NO 37
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 37

```
ctcaactgga tctgcacaca ccagttgag                                   29
```

<210> SEQ ID NO 38
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 38

```
cctgacaccg                                                        10
```

<210> SEQ ID NO 39
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 39
ctcatcacgc agc                                                          13

<210> SEQ ID NO 40
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 40
tcatgccctt cggctgcctc ctggact                                           27

<210> SEQ ID NO 41
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 41
cggtgtcagg                                                              10

<210> SEQ ID NO 42
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 42
agtccaggag gcagccgaag ggcatga                                           27

<210> SEQ ID NO 43
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 43
aatacttact attacttata                                                   20

<210> SEQ ID NO 44
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 44
ttttacttta cttta                                                        15

<210> SEQ ID NO 45
<211> LENGTH: 15
<212> TYPE: DNA
<213> ORGANISM: Artificial Sequence
<220> FEATURE:
<223> OTHER INFORMATION: Synthetic Polynucleotide

```
<400> SEQUENCE: 45 ttttactttta cttta                                                  15

<210> SEQ ID NO 46
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 46
ttttgggcgg gccaaac                                                 17

<210> SEQ ID NO 47
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 47
ttgagaatgg attaagtcaa cctca                                        25

<210> SEQ ID NO 48
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 48
tgaggttgac ttaatccatt ctcaa                                        25

<210> SEQ ID NO 49
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 49
gtgtatgaag tagaggtttg g                                            21

<210> SEQ ID NO 50
<211> LENGTH: 6
<212> TYPE: DNA
<213> ORGANISM: Artificial Sequence
<220> FEATURE:
<223> OTHER INFORMATION: Synthetic Polynucleotide

<400> SEQUENCE: 50 gtttgg                                                              6

<210> SEQ ID NO 51
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 51
gtgtatgaag tagag                                                   15

<210> SEQ ID NO 52
<211> LENGTH: 25
```

```
<212> TYPE: DNA
<213> ORGANISM: Artificial Sequence
<220> FEATURE:
<223> OTHER INFORMATION: Synthetic Polynucleotide

<400> SEQUENCE: 52
ttgagaatgg attaagtcaa cctca                                       25

<210> SEQ ID NO 53
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 53
tggccaaact gctg                                                   14

<210> SEQ ID NO 54
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 54
attgctgacc                                                        10

<210> SEQ ID NO 55
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 55
ggtcagcaat                                                        10

<210> SEQ ID NO 56
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 56
aacgtactgg tga                                                    13

<210> SEQ ID NO 57
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 57
ttttgggcgg gccaaa                                                 16
```

SPECIFIC NUCLEIC ACID AMPLIFICATION WITH COMPOUNDED SELECTIVITY

RELATED APPLICATIONS

This application is a national stage filing under 35 U.S.C. § 371 of international application number PCT/US2014/047196, filed Jul. 18, 2014, which was published under PCT Article 21(2) in English and claims the benefit under 35 U.S.C. § 119(e) of U.S. provisional application Ser. No. 61/856,028, filed Jul. 18, 2013, each of which is incorporated by reference herein in its entirety.

GOVERNMENT SUPPORT

This invention was made with Government support under D007292 awarded by the National Institutes of Health. The Government has certain rights in the invention.

FIELD OF THE INVENTION

Aspects and embodiments of the present disclosure relate to the field of nucleic acid technology.

BACKGROUND OF INVENTION

Nucleic acid amplification is an essential step in most nucleic acid-based detection assays. Accurate detection of nucleic acid biomarkers often relies on the ability to amplify the target nucleic acid in the presence of overwhelming excess (usually 10-fold to 1,000,000-fold) of non-target nucleic acids with sequences similar to the target nucleic acid. In some cases, a non-target nucleic acid differs from a target nucleic acid by as little as one nucleotide (or one nucleotide base pair). Methods of enriching and detecting such rare nucleic acids are often referred to as rare-allele enrichment and rare-allele detection, respectively.

SUMMARY OF INVENTION

The present disclosure is directed, generally, to compositions and methods for improving selectivity of nucleic acid amplification. For some practical applications, it may be advantageous to selectively amplify a rare (e.g., mutant) nucleic acid that differs from an abundant (e.g., wild-type) nucleic acid. One non-limiting example is the detection of circulating tumor DNA (ctDNA), which is released from tumor cells (e.g., into circulating blood). Circulating tumor DNA may be distinguished from normal cell-free DNA of the same locus, which is released from normal cells, by the presence of tumor-specific mutations. A blood (e.g., serum or plasma) sample obtained from a subject with ctDNA contains the ctDNA as well as an overwhelming excess of wild-type cell-free DNA of the same locus. In early stages of cancer, 1 mL of plasma usually contains 1,000 to 10,000 copies of fragmented genome from healthy cells, but possibly as little as less than 10 copies of fragmented genome from cancer cells. Identifying the ctDNA may be assisted by selectively amplifying the ctDNA and/or suppressing amplification of wild-type cell-free DNA. Thus, the disclosure provides, in various aspects and embodiments, methods of selectively amplifying a rare allele of interest and/or suppressing amplification of an abundant (e.g., wild-type) allele. The terms "rare" and "abundant" refer to the relative abundance of nucleic acid of a particular sequence in a sample.

The present disclosure provides, in part, nucleic acids (e.g., oligonucleotides, such as oligonucleotides less than 100 nucleotides in length) engineered to contain specific binding domains that enhance the amplification of a (e.g., at least one) target nucleic acid (e.g., a rare and/or mutant allele) and/or that suppress the amplification of non-target nucleic acids (e.g., wild-type alleles) having sequences similar to the target nucleic acid. As used herein, a nucleic acid "domain" is a consecutive stretch of nucleobase-recognizing moieties of defined length. It some embodiments, a nucleic acid "region" or "domain" is a consecutive stretch of nucleotides of any length. It should be understood that the term "nucleobase-recognizing moieties" is intended to encompass moieties that include, without limitation, nucleotides (e.g., naturally-occurring or modified), modified amino acids, monomers of peptide nucleic acid (PNA), monomers of locked nucleic acid (LNA), and monomers of morpholinos. A "monomer" refers to a single unit of a polymer. For example, nucleotides are monomers of polynucleotides (e.g., nucleic acids), and amino acids are monomers of polypeptides (e.g., proteins). It should be understood that a "nucleotide," in some embodiments, may be replaced with another nucleobase-recognizing moiety.

In some embodiments, methods and composition of the present disclosure may be used to selectively amplify a (e.g., at least one) rare (e.g., mutant) allele present among an excess of abundant (e.g., wild-type) alleles. Thus, abundant alleles that differ from rare alleles by, for example, only a single nucleotide (or nucleotide base pair, in the form of mutation, insertion, or deletion) are referred to herein as "pseudo-target" alleles. For brevity and clarity, target and psuedo-target nucleic acids may be referred to herein as an alleles; however, it should be understood that the methods and compositions as provided herein may be used to amplify any nucleic acid and is not limited to alleles of genes.

In some embodiments, biased amplification of a rare target allele is achieved by engineering a set of nucleic acids that collectively function as primers to enhance amplification of a rare target allele (e.g., mutant allele). For example, in some embodiments, biased amplification of a rare target allele may be achieved by engineering a primer (e.g., a single-stranded primer) with at least two domains: (a) a specificity domain (e.g., a 5' specificity domain) that is complementary to and binds to, for example, a region with a polymorphism in a rare target allele, and (b) a priming domain (e.g., a 3' priming domain) that binds downstream (e.g., in the 3'direction) relative to the polymorphism in a rare target allele (FIG. 1A). The foregoing primer is referred to herein as a "ssPrimer." In some embodiments, a ssPrimer further comprises a competitive domain that is complementary to, or partially complementary to, identical to or similar to as the specificity domain (FIG. 5, bottom panel showing "Toehold Exchange" primer). Thus, it should be understood that the term "ssPrimer" encompasses single-stranded nucleic acids, partially-double stranded primers (e.g., formed by base-pairing of two single-stranded nucleic acids of different lengths), and a collection of nucleic acids (e.g., oligonucleotides) some of which are not intended to bind or be linked to each other.

When a ssPrimer designed to bind to a rare target allele contacts the rare target allele (e.g., mutant allele), binding of both the specificity domain and the priming domain is favored. When a DNA polymerase (e.g., a DNA polymerase with strand displacement activity) is present, the 3' end of the priming domain is extended along the length of a strand of the rare target allele, and the specificity domain of the ssPrimer is displaced via one or more of several possible mechanisms. For example, the specificity domain may be displaced by the extending polymerase (e.g., if the polymerase has strand-displacement activity), by partial or complete degradation by the extending polymerase (e.g., if the polymerase has 5'-to-3' exonuclease activity), by spontaneous dissociation (e.g., if the temperature of the reaction is held at or raised to a temperature similar to or above the melting temperature of the duplex formed by binding of the specificity domain to a strand of the rare target allele), or by a combination of the foregoing mechanisms. It should be understood that the mechanism of displacement of the specificity domain depends, for example, on the design of the ssPrimer (e.g., single-stranded v. partially double-stranded) and the activity of the DNA polymerase (e.g., strand-displacement activity v. exonuclease activity). Thus, the extended (e.g., amplified) product contains the mutation (e.g., polymorphism) that is present in the rare target allele.

By contrast, when the ssPrimer contacts a pseudo-target allele (e.g., wild-type allele), binding of the specificity domain and the priming domain is not favored, and the pseudo-target allele is less likely to be amplified.

The length of the priming domain may differ from the length of the specificity domain. For example, the priming domain may be shorter than the specificity domain. In some embodiments, the difference in length between the priming domain and the specificity domain may be about 2 to about 30, about 5 to about 20, or about 10 to about 20 nucleotides. In some embodiments, the difference in length between the priming domain and the specificity domain is 2, 3, 4, 5, 6, 7, 8, 9, 10, 11, 12, 13, 14, 15, 16, 17, 18, 19, 20, 21, 22, 23, 24, 25, 26, 27, 28, 29, 30 or more nucleotides. Thus, the priming domain may be about 2 to about 30, about 5 to about 20, or about 10 to about 20 nucleotides shorter than the specificity domain. In some embodiments, the length of the priming domain is 2, 3, 4, 5, 6, 7, 8, 9, 10, 11, 12, 13, 14, 15, 16, 17, 18, 19, 20, 21, 22, 23, 24, 25, 26, 27, 28, 29, 30 or more nucleotides shorter than the specificity domain.

One example of a primer of the present disclosure is shown in FIGS. 1A and 2A. FIG. 2A shows a single-stranded nucleic acid containing a 5' specificity domain linked, directly or indirectly (e.g., through a linker, shown as a gray bar) to a single-stranded nucleic acid containing a 3' priming domain. A single-stranded nucleic acid containing an specificity domain may be covalently or non-covalently linked to a single-stranded nucleic acid containing a priming domain. As shown in the example of FIG. 2A, the primer is designed to bind to a strand of a rare target allele via its specificity domain, which has, for example, a point mutation, and via its priming domain, which binds to the strand of the rare target allele downstream (in the 3' direction) of region containing the point mutation. In the presence of a DNA polymerase with strand-displacement activity, the priming domain is extended and the specificity binding domain is displaced.

Another example of a primer of the present disclosure is shown in FIGS. 1B and 2B. FIG. 1B, top panel, shows a single-stranded nucleic acid competitive domain (CD) and a single-stranded nucleic acid containing a specificity domain (SD) linked, directly or indirectly (e.g., through a linker), to a single-stranded nucleic acid containing a priming domain (PD). A single-stranded nucleic acid containing an SD may be covalently or non-covalently linked to a single-stranded nucleic acid containing a PD. As shown in the example of FIG. 1B, bottom panel, the primer is designed to bind to a strand of a rare target allele having a specificity domain binding site (SBS) and a primer binding site (PBS) located downstream (in the 3' direction) of the SBS. The SD is designed to be complementary to and to bind to the SBS on a strand of the rare target allele, and the PD is designed to be complementary to and to bind to the PBS on the same strand of the rare target allele. The CD is designed to be complementary to, partially complementary to, identical to (i.e., 100% identity), or similar to (i.e., less than 100% identity, or less than 99%, less than 98%, less than 95%, less than 90%, less than 85%, less than 80%, or less than 75% identity) the SD. Competitive domains that are complementary to or partially complementary to the specificity domain bind to the specificity domain. Competitive domains that are identical to or similar to the specificity domain bind to a specificity domain binding site on a nucleic acid.

Thus, various aspects and embodiments of the invention provide methods of contacting a pool of target nucleic acids and pseudo-target nucleic acids with an engineered primer (e.g., single-stranded primer) that comprises a specificity domain (e.g., 5' specificity domain) linked to a priming domain (e.g., a shorter 3' priming domain), wherein the specificity domain binds to a specificity domain binding site on the target nucleic acid and the priming domain binds to a priming domain binding site on the target nucleic acid that is downstream of the specificity domain binding site, and extending the priming domain at its 3' end in a target-complementary manner in the presence of a polymerase (e.g., a polymerase that displaces the specificity domain of the engineered primer from the target nucleic acid). In some embodiments, the engineered primer further comprises a competitive domain that is complementary to, partially complementary to, identical to or similar to the specificity domain. In some embodiments, the competitive domain binds to (e.g., binds to at least a portion of) the specificity domain. In some embodiments, the competitive domain competes with the specificity domain.

In some embodiments, a polymerase is a DNA polymerase (e.g., Vent polymerase, Bsm polymerase, Bst polymerase, Csa polymerase or 96-7 polymerase). In some embodiments, a polymerase is a reverse transcriptase. In some embodiments, a polymerase is a reverse transcriptase without RNaseH activity.

In some embodiments, an engineered primer of the present disclosure comprises a deoxyribonucleic acid (DNA), a ribonucleic acid (RNA), a modified RNA (such as those with 2'-fluoro and/or 2'-O-methyl riboses), a locked nucleic acid (LNA), a peptide nucleic acid (PNA) and/or a morpholino.

In some embodiments, a primer (e.g., including a specificity domain and a priming domain) is a contiguous sequence with a (e.g., at least one) non-extendable nucleotide located between the specificity domain and the priming domain. A "non-extendable nucleotide," as used herein, refers to a nucleotide that blocks nucleic acid polymerization (e.g., blocks polymerase read-through). In some embodiments, the non-extendable nucleotide is a non-naturally occurring nucleotide or a dideoxynucleotide (e.g., 2',3' dideoxynucleotides, ddGTP, ddATP, ddTTP and ddCTP). In some embodiments, the non-naturally occurring nucleotide is isoC, isoG, deoxyuridine, 3'-deoxyadenosine, 3'-deoxythymidine, 3'-deoxyguanosine, 3'-deoxycytidine, and/or an otherwise naturally-occurring nucleotide inserted in an inverted orientation.

In some embodiments, a specificity domain and a priming domain are linked to each other through a chemical moiety, referred to as a linker or linkage. In some embodiments, the specificity domain and the priming domain are linked to each other through a 5'-3' linkage. In some embodiments, the specificity domain and the priming domain are linked to each other through a 5'-5' linkage. In some embodiments, a linker is attached to the 5' end of a specificity domain. In some embodiments, a linker is attached to a 3' end of the specificity domain. In some embodiments, a linker is attached to a middle region of a specificity domain (e.g., via a nucleobase that is modified with a conjugation handle). A middle region of a domain is any region that is not at the 3' or 5' end of the domain. In some embodiments, a linker is attached to an additional functional or non-functional moiety, which is in turn attached to the 5' end, the 3' end, or a middle region of the specificity domain. Other linker arrangements are contemplated herein. In some embodiments, the specificity domain and the priming domain are linked to each other through a polyethylene glycol linkage, an alkyl spacer, a PNA linkage or a LNA linkage.

In some embodiments, the specificity domain and the priming domain are chemically conjugated. In some embodiments, the specificity domain and the priming domain are chemically conjugated by azide-alkyne Huisgen cycloaddition or other conjugation reaction involving amine, carboxyl, sulfhydryl, or carbonyl groups, or a combination of any two or more of the foregoing reactions.

In some embodiments, a specificity domain and a priming domain (or a nucleic acid that contains a specificity domain and a nucleic acid that contains a priming domain) are linked to each other by hybridization to a common oligonucleotide or a common multimeric oligonucleotide complex, or by hybridization to each other.

In some embodiments, a specificity domain is engineered to form a hairpin structure. In some embodiments, a specificity domain and a competitive domain are linked (e.g., covalently linked) to form a hairpin structure. In some embodiments, a specificity domain is partially double-stranded (e.g., is bound to a competitive domain as provided herein). In some embodiments, a specificity domain and a competitive domain are linked to moieties that can interact with each other or with a common molecule or molecular complex. In some embodiments, the moieties are nucleic acids (e.g., oligonucleotides, or domains within an oligonucleotide).

In some embodiments, the 3' end of a specificity domain contains a blocking moiety. In some embodiments, a blocking moiety prevents the 3' end of a specificity domain from being extended and/or from being degraded by a nucleic acid-modifying enzyme (e.g., a DNA polymerase or an exonuclease).

In some embodiments, a target nucleic acid is single-stranded. In some embodiments, a target nucleic acid is DNA or RNA.

In some embodiments, a target nucleic acid is present in a single copy or in low copy. In some embodiments, a target nucleic acid contains at least one mutation (e.g., point mutation, deletion or insertion) relative to a wild-type counterpart nucleic acid. In some embodiments, a target nucleic acid contains a single nucleotide polymorphism (SNP).

In some embodiments, a method further comprises amplifying a nucleic acid bound by an engineered primer. In some embodiments, a nucleic acid bound by an engineered primer is amplified by polymerase chain reaction. In some embodiments, a method further comprises amplifying a nucleic acid that is recognized by an engineered primer. In some embodiments, a nucleic acid that is recognized by an engineered primer is amplified by polymerase chain reaction. In some embodiments, a nucleic acid that is recognized by an engineered primer is amplified by an isothermal amplification reaction.

In some embodiments, provided herein are compositions comprising an engineered primer (e.g., ssPrimer) of the present disclosure, a target nucleic acid and polymerase. In some embodiments, provided herein are compositions comprising an engineered primer (e.g., ssPrimer) of the present disclosure, a target nucleic acid and a pseudo-target nucleic acid. In some embodiments, provided herein are compositions comprising an engineered primer (e.g., ssPrimer) of the present disclosure, a target nucleic acid, a pseudo-target nucleic acid and polymerase. In some embodiments, provided herein are compositions comprising a plurality of engineered primers (e.g., ssPrimers). It should be understood that a plurality of engineered primers refers to a plurality of heterogeneous (e.g., a mixed population of different) or homogenous (e.g., a population of the same primer) engineered primers. In some embodiments, provided herein are compositions comprising an engineered primer comprising a priming domain and a specificity domain and optionally a competitive domain. In some embodiments, the competitive domain is complementary to, or partially complementary to, the specificity domain.

In some embodiments, biased amplification of a rare target allele is achieved by engineering a set of nucleic acids that collectively function to block amplification of abundant pseudo-target alleles (e.g., wild-type alleles). In some embodiments, biased amplification of rare target alleles is achieved by engineering a thermodynamic, partially double-stranded nucleic acid with enhanced target specificity having first and second nucleic acid strands arranged into (a) one double-stranded pseudo-target non-specific domain, (b) one double-stranded pseudo-target specific domain, and (c) one single-stranded pseudo-target specific domain contributed to by the first nucleic acid strand, wherein the double-stranded pseudo-target non-specific domain has a standard free energy approximately equal to the standard free energy for the single-stranded pseudo-target specific domain bound to a pseudo-target nucleic acid, and wherein the 3' end of the first nucleic acid strand and the 3' of the second nucleic acid strand are non-extendable. Variations and functional analogs of the double-stranded pseudo-target non-specific domain including two nucleic-acid or non-nucleic-acid moieties interacting with each other, with a common molecule, or a common molecular complex are contemplated herein. The foregoing partially double-stranded nucleic acid of the invention is referred to herein as a "dsBlocker."

In some embodiments, biased amplification of rare target alleles is achieved by engineering a thermodynamic, partially double-stranded nucleic acid with enhanced target specificity having first and second nucleic acid strands arranged into (a) one double-stranded pseudo-target non-specific domain, (b) one double-stranded pseudo-target specific domain, and (c) one single-stranded pseudo-target specific domain contributed to by the first nucleic acid strand, wherein the double-stranded pseudo-target non-specific domain has a dissociation constant equal to or lower than 10 mM at the condition under which the partially double-stranded nucleic acid is to be used. In some embodiments, the 3' end of the first nucleic acid strand and the 3' of the second nucleic acid strand are non-extendable. Variations and functional analogs of the double-stranded pseudo-target non-specific domain including two nucleic-acid or non-nucleic-acid moieties interacting with each other, with a common molecule, or a common molecular complex are contemplated herein.

When a dsBlocker designed to bind to a pseudo-target allele (e.g., wild-type allele) contacts the pseudo-target allele, a strand of the pseudo-target allele displaces the second nucleic acid strand of the dsBlocker and binds to first nucleic acid strand of the dsBlocker (i.e., the strand containing the single-stranded pseudo-target specific domain), and amplification of the pseudo-target allele is blocked. By contrast, when the dsBlocker contacts a strand of a rare target allele (which is not complementary to first strand of the dsBlocker), binding of the first nucleic acid strand of the dsBlocker to the second nucleic acid strand of the dsBlocker is favored over binding of the first nucleic acid strand of the dsBlocker to the rare target allele. This is because a single-nucleotide change between the first nucleic acid strand of the dsBlocker and the strand of the rare target allele can destabilize a nucleic acid duplex (e.g., double-stranded nucleic acid). When a dsBlocker of the present disclosure is used in an amplification reaction in combination with a generic forward primer that binds to both the target and pseduo-target nucleic acids (e.g., downstream of the polymorphism in the rare target allele), the dsBlocker preferentially binds to the pseduo-target nucleic acid (e.g., downstream of the generic primer) and blocks extension of the generic primer. On the target nucleic acid, which remains free of the dsBlocker, the generic forward primer binds and is extended, and thus the target allele is preferentially amplified.

Thus, various other aspects and embodiments of the present disclosure provides methods of contacting a pool of target nucleic acids and pseudo-target nucleic acids with (a) a nondiscriminatory primer (e.g., that can bind to the target and the pseudo-target nucleic acids), and (b) an engineered partially double-stranded nucleic acid that comprises first and second nucleic acid strands arranged into (i) one double-stranded pseudo-target non-specific domain, (ii) one double-stranded pseudo-target specific domain, and (iii) one single-stranded pseudo-target specific domain contributed to by the first nucleic acid strand, wherein the double-stranded pseudo-target non-specific domain has a standard free energy approximately equal to the standard free energy for the single-stranded pseudo-target specific domain bound to a pseudo-target nucleic acid, and wherein the 3' end of the first nucleic acid strand and the 3' of the second nucleic acid strand are non-extendable; and extending the nondiscriminatory primer of (a) at its 3' end in a target-complementary manner in the presence of a polymerase. As used herein, a "nondiscriminatory primer" refers to a 'traditional' single-stranded oligonucleotide (e.g., about 4 to about 35, about 10 to about 30, or about 15 to about 25 nucleotides in length, or longer) that binds to both a target nucleic acid and a pseudo-target nucleic acid. This single-stranded primer typically does not discriminate between a target and pseudo target nucleic acid. When bound to a target nucleic acid in the presence of polymerase, a nondiscriminatory primer is extended in a target-complementary manner. By contrast, when bound to a pseudo-target nucleic acid in the presence of polymerase, a nondiscriminatory primer is blocked by the presence of a blocking strand of a dsBlocker.

In some embodiments, the present disclosure provide methods of contacting a pool of target nucleic acids and pseudo-target nucleic acids with (a) a nondiscriminatory primer (e.g., that can bind to the target and the pseudo-target nucleic acid), and (b) an engineered partially double-stranded nucleic acid that comprises first and second nucleic acid strands arranged into (i) one double-stranded pseudo-target non-specific domain, (ii) one double-stranded pseudo-target specific domain, and (iii) one single-stranded pseudo-target specific domain contributed to by the first nucleic acid strand, wherein the double-stranded pseudo-target non-specific domain has a dissociation constant equal to or lower than 10 mM at the condition under which the partially double-stranded nucleic acid is to be used; and extending the nondiscriminatory primer of (a) at its 3' end in a target-complementary manner in the presence of a polymerase. In some embodiments, the 3' end of the first nucleic acid strand and the 3' of the second nucleic acid strand are non-extendable.

In some embodiments, the first nucleic acid strand and/or the second nucleic acid strand comprises a non-extendable nucleotide at its 3' end. In some embodiments, the non-extendable nucleotide is a non-naturally occurring nucleotide or a dideoxynucleotide. In some embodiments, the non-naturally occurring nucleotide is isoC, isoG, deoxyuridine, 3'-deoxyadenosine, 3'-deoxythymidine, 3'-deoxyguanosine, 3'-deoxycytidine, and/or an otherwise naturally-occurring nucleotide inserted in an inverted orientation.

In some embodiments, the nondiscriminatory primer of (a) is about 4-35 nucleotides in length.

In some embodiments, the double-stranded pseudo-target non-specific domain of (b) is about 4-150 (e.g., 4-21) nucleotides in length.

In some embodiments, the double-stranded pseudo-target specific domain of (b) is about 4-150 nucleotides in length.

In some embodiments, the single-stranded pseudo-target specific domain of (b) is about 4-30 (e.g., 4-20) nucleotides in length.

In some embodiments, an engineered primer of the present disclosure comprises a deoxyribonucleic acid (DNA), a ribonucleic acid (RNA), a modified RNA (such as those with 2'-fluoro and/or 2'-O-methyl riboses), a locked nucleic acid (LNA), a peptide nucleic acid (PNA) and/or a morpholino.

In some embodiments, the target nucleic acid is present in a single copy or in low copy.

In some embodiments, the target nucleic acid comprises at least one mutation.

In some embodiments, the target nucleic acid comprises a single nucleotide polymorphism (SNP).

In some embodiments, the method further comprises amplifying the nucleic acid bound by the nondiscriminatory primer of (a). In some embodiments, the nucleic acid bound by the nondiscriminatory primer of (a) is amplified by polymerase chain reaction. In some embodiments, the nucleic acid bound by the nondiscriminatory primer of (a) is amplified by an isothermal amplification reaction.

In some embodiments, provided herein are compositions comprising a dsBlocker of the present disclosure, a target nucleic acid and polymerase. In some embodiments, provided herein are compositions comprising a dsBlocker of the invention, a target nucleic acid and a pseudo-target nucleic acid. In some embodiments, provided herein are compositions comprising a dsBlocker of the invention, a target nucleic acid, a pseudo-target nucleic acid and polymerase. In some embodiments, provided herein are compositions comprising a dsBlocker of the invention, a single-stranded primer that binds to a target nucleic acid, the target nucleic acid, and polymerase. In some embodiments, provided herein are compositions comprising a dsBlocker of the invention, a single-stranded primer that binds to a target nucleic acid, the target nucleic acid and a pseudo-target nucleic acid. In some embodiments, provided herein are compositions comprising a dsBlocker of the invention, a single-stranded primer that binds to a target nucleic acid, the target nucleic acid, a pseudo-target nucleic acid and polymerase. In some embodiments, provided herein are compositions comprising a plurality of dsBlockers. It should be understood that a plurality of dsBlockers refers to a plurality of heterogeneous (e.g., a mixed population of different) or homogenous (e.g., a population of the same primer) dsBlockers.

Also provided herein is a nucleic acid bound to an engineered single-stranded primer that comprises a 5' specificity domain linked to a 3' priming domain, wherein the specificity domain is bound to a specificity domain binding site on the target nucleic acid and the priming domain is bound to a priming domain binding site on the target nucleic acid that is upstream of the specificity binding site.

Additionally, the present disclosure provides a nucleic acid bound to (a) a nondiscriminatory primer and (b) a blocker strand comprising an initial toehold domain, a branch migration domain and a balancing toehold domain, wherein or optionally wherein the 3' end of the blocker strand is non-extendable.

The present disclosure also provides compositions and methods of detecting multiple nucleic acid amplification products. In some embodiments, a composition comprises a set of molecules that comprise (1) a first domain having a sequence that is not restricted by the target sequence and that is attached to a signal-generating moiety, (2) a second domain that is complementary to or partially complementary to a target and is attached to a first signal-modulating moiety that can affect the signal generated by the signal-generating moiety, and (3) a third domain that is complementary to or partially complementary to the first domain and is attached to a second signal-modulating moiety that can affect the signal generated by the signal-generating moiety, wherein the signal-generating moiety and the first signal-modulating moiety are separated by at least one phosphodiester bond. The foregoing set of molecules is referred to herein as a "Temperature Barcoded Hydrolysis Probe," or "TBHP."

Various aspects and embodiments of the present disclosure provide methods of contacting a plurality of target nucleic acids with a plurality of TBHPs. In some embodiments, a method further comprises contacting the plurality of target nucleic acids with the plurality of TBHPs in the presence of at least one enzyme with nuclease activity.

BRIEF DESCRIPTION OF THE FIGURES

It is to be understood that the Figures are not necessarily to scale, emphasis instead being placed upon generally illustrating the various concepts discussed herein.

FIG. 4B depicts examples of non-covalent linkers. FIG. 4C depicts examples of linkage configurations.

DETAILED DESCRIPTION OF INVENTION

Figure 1A:
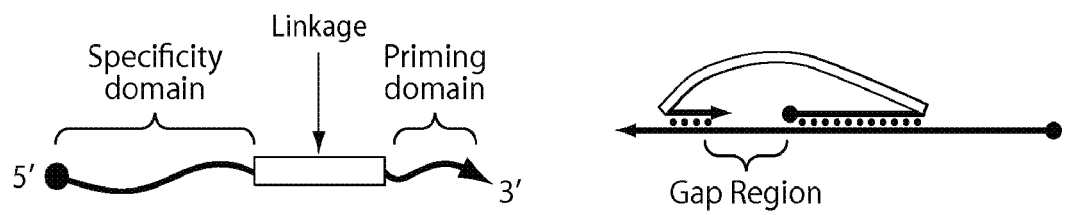
FIGS. 1A-1B depict examples of ssPrimers of the present disclosure.

Nucleic acid amplification is an essential step in most nucleic acid-detection assays. In many cases, accurate detection of nucleic acid biomarkers, for example, relies on the ability to amplify the true target in the presence of excess non-target nucleic acids that have sequences similar to the target nucleic acid. As discussed above, many aspects of the invention may be used to selectively amplify and/or detect a rare and/or mutant allele present amongst an excess of the wild-type alleles. Thus, abundant non-target (e.g., wild-type) alleles will be referred to herein as pseudo-target alleles/nucleic acids, while rare and/or mutant alleles will be referred to herein as target alleles/nucleic acids. Further, for brevity and clarity, the target nucleic acid of interest may be referred to herein as a target allele; however, it should be understood that the invention may be used to amplify any nucleic acid of interest and is not limited to genes/alleles.

Typical amplification reactions for detecting, for example, a polymorphism (e.g., mutation), use a primer (e.g., single-stranded primer or partially-double-stranded primer) that is complementary to a region on a rare target strand that contains the mutation (Newton, C. R. et al. *Nucleic Acids Res.*, 17(7):2503-16, April 1989; Cha, R. S. et al. *PCR Methods Appl.*, 2(1):14-20, August 1992). Thus, the primer preferentially binds to the region with the polymorphism (e.g., mutation), and the DNA polymerase extends the primer bound to its intended target. In some instances, however, the primer binds to an unintended nucleic acid such as a strand of a wild-type allele (i.e., strand of a pseudo-target allele), and then DNA polymerase extends the primer bound to the strand of the wild-type, which results in an extension product that contains the polymorphism of the rare target allele (because the primer contains the polymorphism of the rare target allele). Thus, the extension product is amplified, sequenced and/or identified as representative of a rare target allele containing the polymorphism, when in fact the allele was a wild-type allele. Presence of the amplified product incorrectly indicates that the rare target allele was present initially. This is often how false-positive results are obtained.

As used herein, "fold amplification" refers to the ratio of a nucleic acid amplification product to its initial template nucleic acid:

$$\text{Fold-amplification} = \frac{\text{Number of molecules of the amplification product}}{\text{Number of molecules of the template}}$$

As used herein, "selectivity" refers to the ratio of fold amplification of target sequence to fold amplification of pseudo-target sequence:

$$\text{Selectivity} = \frac{\text{Fold amplication of target}}{\text{Fold amplication of pseudo-target}}$$

Various aspects and embodiments of the present disclosure require predicting or estimating thermodynamic parameters (e.g., $\Delta G$, $\Delta H$, $\Delta S$ and melting temperature) of nucleic hybridization and minimum free energy (MFE) structure and partition function of a nucleic acid molecule or a nucleic acid complex. Several established computational frameworks, algorithms, and databases (SantaLucia, J., et al. *Annu Rev Biophys Biomol Struct*, 33:415-440, 2004; Dirks, R. M., et al. *SIAM Rev*, 49(1):65-88, 2007) can be used to achieve these tasks. Several publicly available software programs (e.g., HyTher, Mfold, UNAfold and NUPACK) can facilitate the process.

ssPrimer and ssPrimer Nucleic Acid Amplification

Figure 1B:
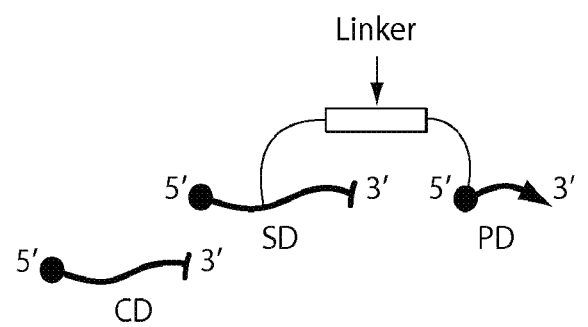
Figure 1B:
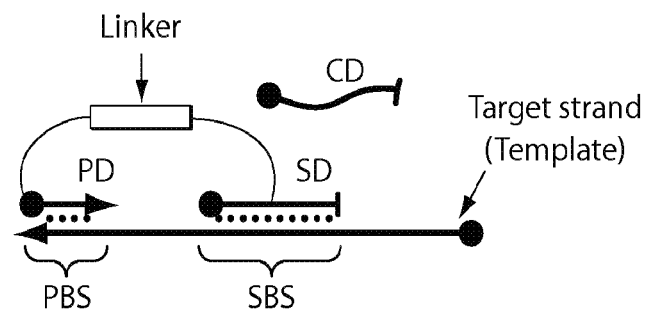

In some aspects of the present disclosure, the problem of false-positive results is addressed using a single-stranded primer and method of amplification. As used herein, a "ssPrimer" of the invention refers to an engineered single-stranded primer with a specificity domain (e.g., 5' specificity domain) linked to a shorter priming domain (e.g., 3' priming domain) (FIG. 1). In some embodiments, a ssPrimer comprises a specificity domain (SD), a priming domain (PD), and a linker that connects the two domains to each other (FIG. 1, left). The region on a nucleic acid that is complementary to the SD is referred to herein as a "SD binding site," or "SBS." Likewise, the region on a nucleic acid that is complementary to the PD is referred to herein as a "PD binding site," or "PBS." A ssPrimer is engineered to have a 3' PD that binds to the target allele upstream of the 5' SD, thereby forming a pseudo-knotted structure (FIG. 1, right). When a DNA polymerase with strand displacement activity (e.g., Vent polymerase) is present, the 3' end of the PD can be extended along the target allele, and the SD is displaced. It should be understood that, in some instances, the position of the PD may be described relative to the SD and relative to an extended complementary strand. Thus, a PD that is described as "upstream" of the SD is positioned such that when the priming domain is extended in the 5' to 3' direction in the presence of polymerase, the newly formed extension is able to displace the SD. In some instances, the position of the PD may be described relative to the SD binding site on the target strand. Thus, a PD that is described as "downstream" of a SD binding site is positioned such that when the priming domain is extended in the 5' to 3' direction in the presence of polymerase, the newly formed extension is able to displace the SD. The binding site for the specificity domain is upstream of the binding site for the priming domain. Thus, the priming domain binds downstream of the specificity domain, as shown for example, in FIG. 1B.

In some embodiments, a ssPrimer further comprises a competitive domain (CD). Thus, in some embodiments, a primer of the present disclosure comprises a set of nucleic acids that comprises at least three domains: (a) a specificity domain (SD) that binds to, for example, a region with polymorphism in the rare target strand, (b) a priming domain (PD) that binds to the target strand downstream (e.g., in the 3' direction) of the region with the polymorphism, and (c) a competitive domain (CD) whose sequence is complementary, partially complementary, identical or similar to the SD, wherein the priming domain (PD) comprises a 3' end that can be extended by a DNA polymerase, and the SD and the PD are connected directly or indirectly by covalent or non-covalent interaction(s).

In the Figures, a filled circle represents the 5' end of a nucleic acid strand and an arrow represents the 3' end of a nucleic acid strand. When a ssPrimer designed to bind to a target strand contacts the target strand, binding of both the SD and the PD is favored. When a DNA polymerase is present, the 3' end of the PD is extended along the length of the target strand, and the SD of the ssPrimer is displaced via several possible mechanisms including, without limitation, displacement by the extending polymerase (e.g., if the polymerase has strand-displacement activity), partial or complete degradation by the extending polymerase (e.g., if the polymerase has 5'-to-3' exonuclease activity), spontaneous dissociation (e.g., if the temperature of the reaction is held at or raised to a temperature similar to or above the melting temperature of the duplex formed by the SBS and the SD), or a combination of the foregoing mechanisms. Thus, the extended product contains the version of the polymorphism (e.g., mutation) that is present in the target allele.

Figure 2A:
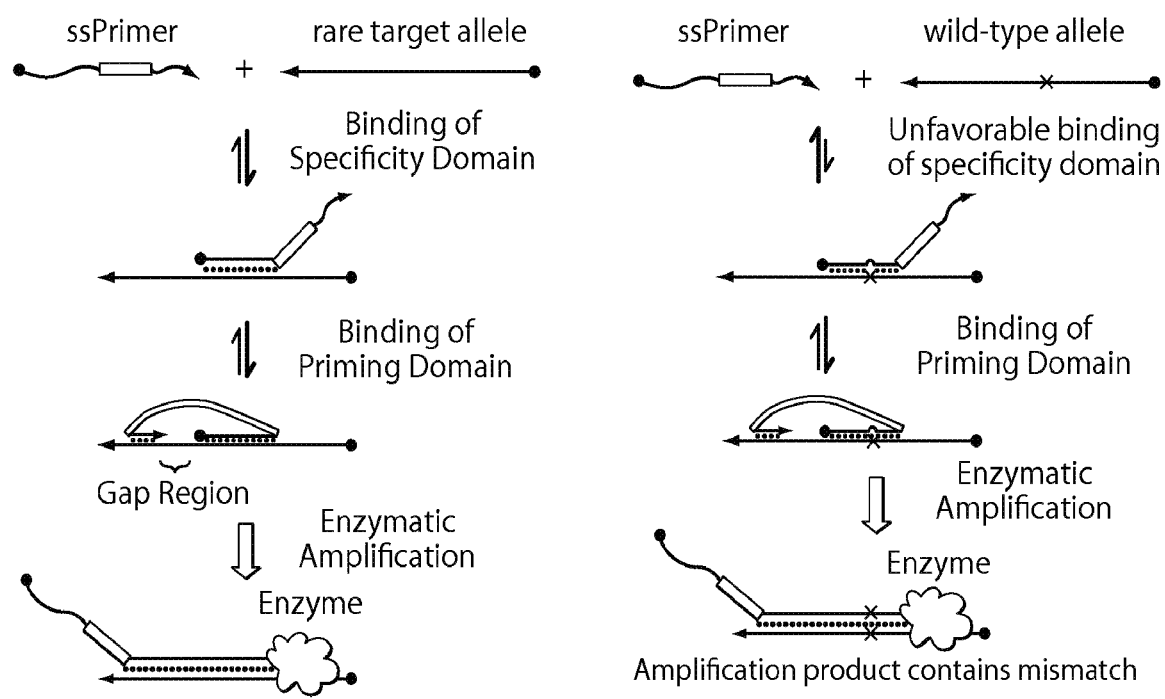
FIGS. 2A-2C depict schemes of polymerase chain reaction (PCR)-based allele-enrichment using ssPrimers as forward primers.
Figure 2B:
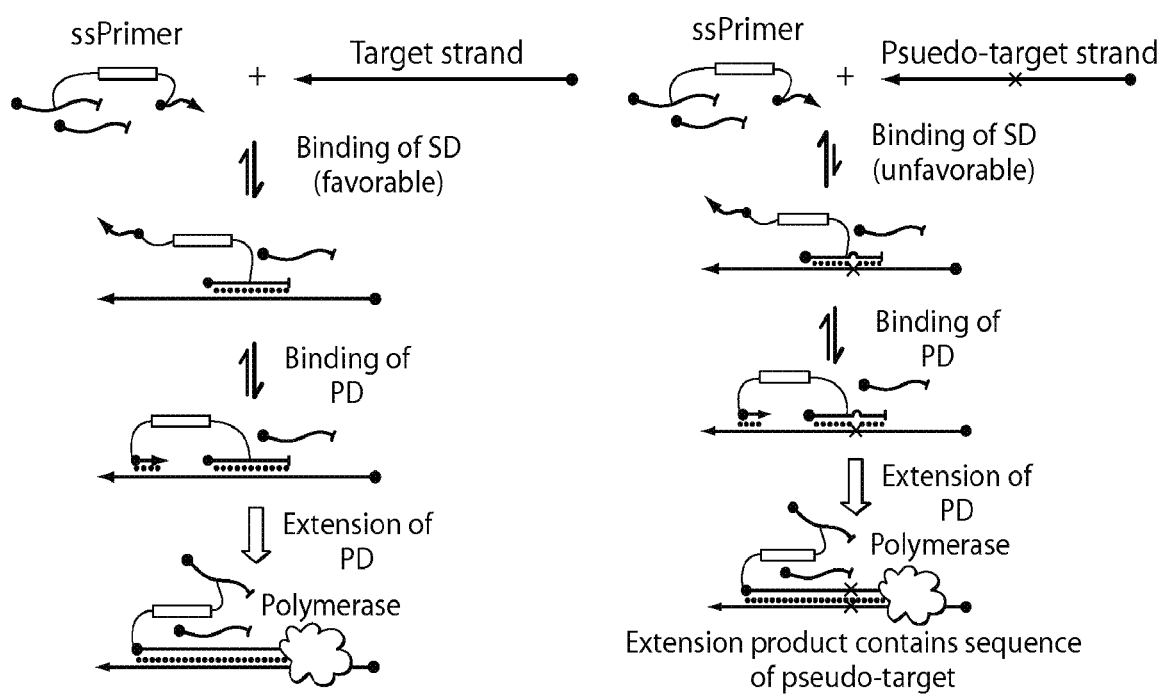

The amplification reactions of the invention, which in some embodiments use the ssPrimer, selectively amplify a rare target allele of interest while suppressing amplification of pseudo-target alleles, which is some instances may be wild-type alleles (FIG. 2). The SD of the ssPrimer contains, for example, a polymorphism complementary to a polymorphism of interest in a strand of a rare target allele and thus "checks" for the complementary polymorphism in a nucleic acid strand and preferentially binds to the region of the strand of the rare target allele containing the complementary polymorphism. The PD also binds to the strand of the rare target allele downstream of the SD binding site, and when the PD is extended, the extended region contains the polymorphic region present in the rare target allele (FIG. 2A, left). On occasions when the SD domain binds to a wild-type strand, the extension product will contain the sequence of the wild-type allele rather than the version of the polymorphism present in the target allele (FIG. 2A, right). This feature helps ensure that the incorrectly amplified wild-type allele is unfavorably amplified (e.g., in every cycle of a multiple-cycle amplification reaction such as PCR and some isothermal amplification reactions (Craw and Balachandran. *Lab Chip.*, 12(14):2469-86)), resulting in compounded selectivity.

The present disclosure contemplates the use of essentially any sequence-specific DNA/RNA binding molecule as a component of the domains as provided herein (e.g., the SD, CD, IT, BT and BM). For example, the SD may comprise deoxyribonucleic acid (DNA), ribonucleic acid (RNA), modified RNA, peptide nucleic acid (PNA) (Nielsen, P. E. et al. *Science* 254 (5037): 1497-50, 1991), locked nucleic acid (LNA) (Satoshi, O., et al. *Tetrahedron Lett*. 38 (50): 8735-8, 1997; Koshkin, A. A., et al. *Tetrahedron* 54 (14): 3607-30, 1998, incorporated herein by reference), DNA/RNA-binding protein, DNA/RNA-binding ribonucleoprotein, DNA/RNA-binding peptide, and/or morpholino (Summerton, J., et al. *Antisense & Nucleic Acid Drug Development* 7 (3): 187-95, 1997, incorporated herein by reference).

In some embodiments, the SD and CD may be engineered to form a hairpin or a partially double-stranded probe (Zhang, D. Y. et al. *Nat. Chem.*, 4(3):208-14, March 2012, incorporated herein by reference).

The specificity domain (SD) of the ssPrimer is typically longer than the priming domain (PD). In some embodiments, the length of the SD is about 10 to about 50 nucleotides, or longer. For example, the length of the SD may be 10 to 15, 10 to 20, 10 to 30, 10 to 40, 10 to 50, 15 to 20, 15 to 30, 15 to 40, 20 to 30, 20 to 40, 20 to 50, 30 to 40, or 40 to 50 nucleotides. In some embodiments, the length of the SD may be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides, or longer. In some embodiments, the length of the PD is about 5 to about 20 nucleotides, or longer. For example, the length of the PD may be 5 to 10, 5 to 15, 10 to 15, or 15 to 20 nucleotides. In some embodiments, the length of the PD may be 5, 6, 7, 8, 9, 10, 11, 12, 13, 14, 15, 16, 17, 18, 19 or 20 nucleotides, or longer. In some embodiments, the length of the SD and PD are such that binding of a primer (e.g., ssPrimer) to a nucleic acid will be controlled more by the accurate binding of the SD rather than the PD.

It is to be understood that in the context of ssPrimer domain length (e.g., SD, PD, CD and/or linker), the term "nucleotide" encompasses any monomer of a DNA-binding molecule such as, for example, DNA, RNA, modified RNA, nucleotide analogues, LNA, PNA and/or morpholino. Thus, a ssPrimer domain having a length of "X" nucleotides may refer to a primer length that is approximately equivalent to "X" nucleotides (e.g., it may include at least one non-naturally occurring nucleotide/moiety).

A linker, connecting the SD to the PD, in some embodiments, may have a length equivalent to 1 to about 15 nucleotides, or longer. For example, in some embodiments, the linker may have a length equivalent to 1 to 5, 1 to 10, 5 to 10, 5 to 15, or 10 to 15 nucleotides, or longer. In some embodiments, the linker may have a length equivalent to 1, 2, 3, 4, 5, 6, 7, 8, 9, 10, 11, 12, 13, 14 or 15 nucleotides.

Without being bound by theory, it is thought that the priming domain (PD) of the ssPrimer binds template nucleic acid more readily when it is recruited by the specificity domain (SD) in comparison to without the SD domain. When a ssPrimer of the invention is bound to a template nucleic acid via the SD, the binding of the PD to the template is a unimolecular process. By contrast, without a contribution from the SD, the binding of the PD to the template is a bimolecular process. Thus, when the SD is bound to the template, the local concentration of the PD is substantially higher than the global concentration of the PD (which equals the concentration of the ssPrimer).

An order-of-magnitude estimation of the local concentration of the PD may be obtained by comparing the unimolecular process to hairpin formation. For example, at a given temperature T, the free energy change of hairpin formation ($\Delta G°$) is governed by several entropic and enthalpic factors in the following way:

$$\Delta G° = \Delta H°_{base\ stacking} - T(\Delta S°_{base\ stacking} + \Delta S°_{loop\ formation}) \quad (1)$$

For the purpose of comparison, hybridization may be considered a pseudo-unimolecular reaction in which one strand is followed and the concentration of other strand is treated as an environmental factor. The free energy change of hybridization can be calculated using the following equation:

$$\Delta G° = \Delta H°_{base\ stacking} - T(\Delta S°_{base\ stacking} + \Delta S°_{initiation} + R\ \ln([\text{complementary strand}]/1\ M)) \quad (2)$$

where R is gas constant and has the value of 0.0019858775 kcal/mol/K.

Comparing the temperature dependent factors of equations (1) and (2) shows that $\Delta S°_{loop\ formation}$ is equivalent to:
$\Delta S°_{initiation} + R\ \ln([\text{complementary strand}]/1\ M)$ Therefore, to one arm of a hairpin, the local concentration of the other arm (the complementary strand) can be calculated as following:

$$\text{local concentration} = e^{\wedge}(\Delta S°_{loop\ formation} - \Delta S°_{initiation}/R) \quad (3)$$

Hairpin loop of 10-nt, 20-nt and 30-nt have $\Delta S_{loop\ formation}$ of −14.8, −18.7 and −20.3 e.u., respectively. $\Delta S_{initiation}$ equals −5.7 e.u. Using equation (3), the local concentration of the other arm in a hairpin with loop length of 10-nt, 20-nt and 30-nt is estimated to be 10 mM, 1.5 mM, and 0.65 mM, respectively.

With a ~15-nt PD and a ~15-nt gap between the SD-binding site and PD-binding site, the local concentration of the PD in a unimolecular event should be similar to or a bit lower than the local concentration of the complementary arm in a 30-nt hairpin loop. That is, the local concentration of the PD in a unimolecular event should be at middle to high micro-molar level. By contrast, the global concentration of the PD is only at middle nano-molar level. Therefore, it is likely that the local PD concentration is ~100- to ~1000-fold higher than the global PD concentration.

Function and Design of Competitive Domain

As with many nucleic acid hybridization reactions, when present alone, a specificity (SD) domain binds to a specificity domain binding site (SBS) with sufficient sequence specificity (e.g., the SD binds the SBS more strongly than the equivalent site on the pseudo-target, referred to as the pSBS) under a narrow range of conditions. In some embodiments (e.g., if the reaction temperature is substantially lower than the melting temperature of a SD:pSBS duplex), a specificity domain binds a specificity domain binding site on a rare target allele and a comparable region on a pseudo-target allele equally well. In such embodiments, both the target nucleic acid and the pseudo-target nucleic acid are amplified efficiently, and the target is insufficiently enriched. In some embodiments (e.g., if the reaction temperature is substantially higher than the melting temperature of the SD:SBS duplex), the specificity domain binds a specificity domain binding site on a rare target allele and a comparable region on a pseudo-target allele nearly equally poorly. In such embodiments, neither the target nucleic acid nor the pseudo-target nucleic acid is amplified efficiently, and the target nucleic acid is insufficiently enriched. A competitive domain (CD) of a ssPrimer, as provided herein, expands the range of conditions under which the specificity domain distinguishes a target allele and a pseudo-target allele (e.g., preferentially binds to a target allele) by "canceling" some of the entropy change in binding reactions.

Figure 2C:
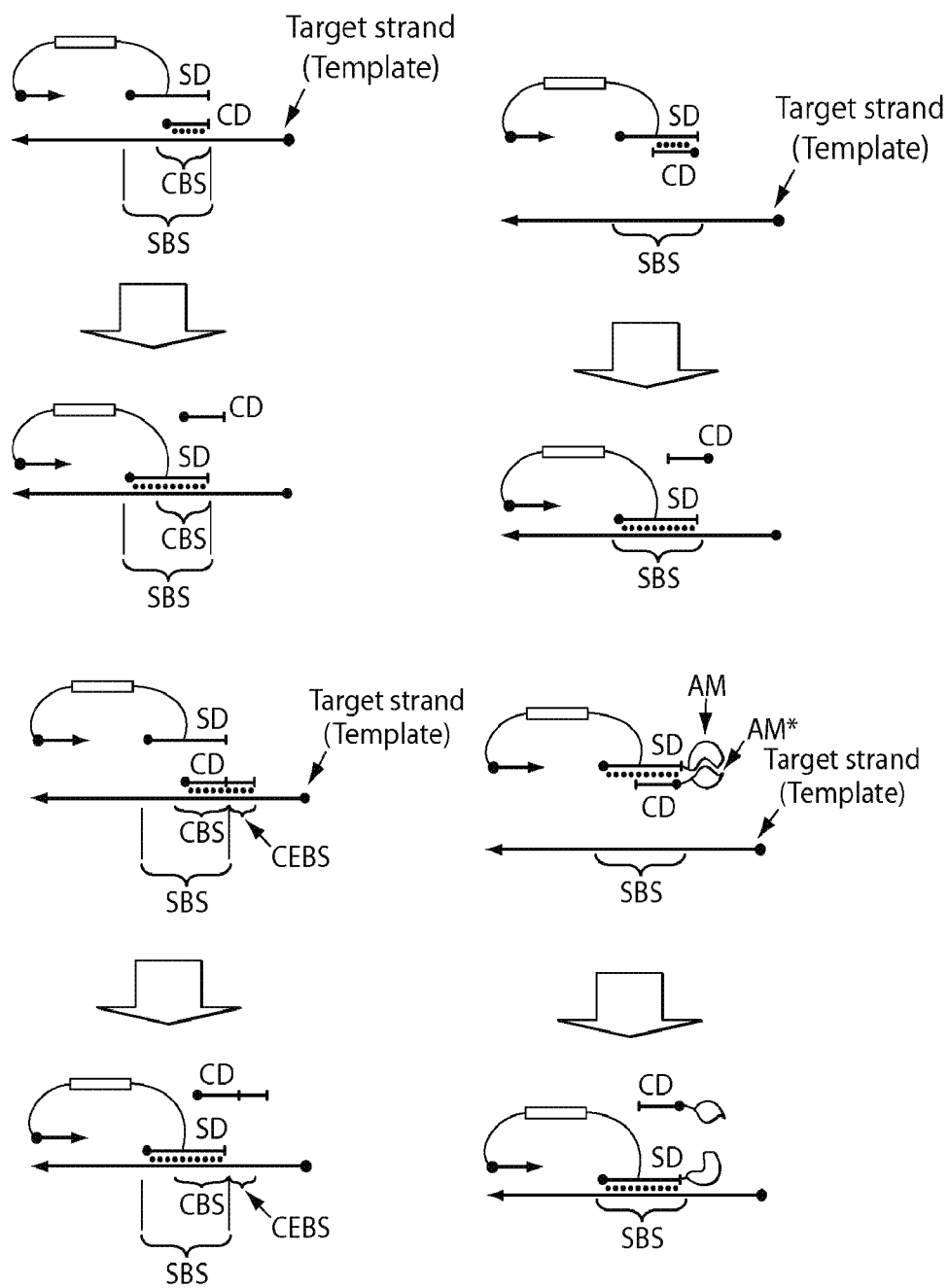

FIG. 2C shows ssPrimers configured with a competitive domain (CD). FIG. 2C, top left, depicts a CD that comprises a sequence identical to or similar to a portion of the specificity domain (SD). Thus, the CD is complementary to, or partially complementary to, the specificity domain binding site. The region on the target and/or the pseudo-target strand to which the CD binds is referred to as the "CD-binding site" or "CBS." FIG. 2C, bottom left, depicts a CD strand that comprises an additional domain that is complementary to, or partially complementary to, a region on the target and pseudo-target strands flanking a specificity domain binding site (SBS) (or a pseudo SBS (pSBS), located on a pseudo target allele). This region on the target and/or the pseudo-target strand is referred to as a "CD extension-binding site" or "CEBS."

In some embodiments, the SD and the CD are engineered such that the genetic (e.g., nucleotide) difference between the target and the pseudo-target (e.g., the mutation) resides within the CBS. In such embodiments, the CD may be designed to be complementary to the pseudo-target strand but not complementary to the target strand. In some embodiments, a CD can improve the sequence selectivity of the SD because interaction between the CD and the pseudo-target allele is stronger than interaction between the CD and the target allele.

In some embodiments, the SD and the CD are engineered such that the genetic (e.g., nucleotide) difference between the target and the pseudo-target (e.g., the mutation) resides within the SBS but outside the CBS. In some embodiments, a CD binds the target strand and the pseudo-target strand equally well. Thus, a CD does not improve the sequence selectivity of the SD but may widen the range of temperature in which the SD exhibits satisfactory sequence specificity for the target allele by entropy cancellation.

In some embodiments, a SD and a CD are engineered such that the sequence (e.g., nucleotide) difference between the target and the pseudo-target (e.g., the mutation) resides outside the SBS but within the CEBS. In some embodiments, a CD may be designed to be complementary to the pseudo-target allele but not complementary to the target allele. In such embodiments, the SD does not distinguish between the target allele and the pseudo-target allele per se. However, because binding of the CD to the pseudo-target allele is stronger than binding of the CD to the target allele, the SD, in some embodiments, preferentially binds the target strand over the pseudo-target strand.

FIG. 2C, top right, depicts a CD that is complementary to, or partially complementary to, the SD. In some embodiments, the SD may be linked, through covalent or non-covalent interactions, to an additional moiety (referred to in the figure as "AM") that is not related to the sequence of the target or the pseudo-target. In some embodiments, the CD may be linked to a moiety (referred to in the Figure as AM*) that can interact with the AM (FIG. 2C, bottom right). In some embodiments, the AM and the AM* are complementary nucleic acids.

In some embodiments, the length of the CD is about 10 to about 50 nucleotides, or longer. For example, the length of the CD may be 10 to 15, 10 to 20, 10 to 30, 10 to 40, 10 to 50, 15 to 20, 15 to 30, 15 to 40, 20 to 30, 20 to 40, 20 to 50, 30 to 40, or 40 to 50 nucleotides. In some embodiments, the length of the CD may be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides, or longer.

Linkage Between the Specificity Domain and the Priming Domain

In some embodiments, a ssPrimer comprises a nucleic acid containing a specificity domain (SD) linked to a nucleic acid containing a priming domain (PD). In some embodiments, the two nucleic acids interact with each other (FIG. 4B(i)), with a common molecule (FIG. 4B(iii)), with a common molecular complex (FIG. 4B(iv)), or with a combination of the foregoing interaction modes (e.g., FIG. 4B(ii), FIG. 4B(v)). The two nucleic acids may interact via non-covalent interactions such as DNA hybridization (FIG. 4B(vi) to 4B(x)), protein-protein interaction, protein-small molecule interaction, magnetic interaction, electronic charge interaction, and the like. In some embodiments, the nucleic acid containing the PD contains at least one chemical modification so that when the extension product of a ssPrimer serves as the template in later cycles of amplification, the DNA polymerase cannot read past the modification. Examples of such modification include, without limitation polyethylene glycol, an alkyl spacer, a PNA or a LNA.

In some embodiments, a ssPrimer comprises a single nucleic acid containing both a SD and a PD and contains at least one chemical modification so that when the extension product of a ssPrimer serves as the template in later cycles of amplification, the DNA polymerase cannot read past the modification.

Figure 4A:
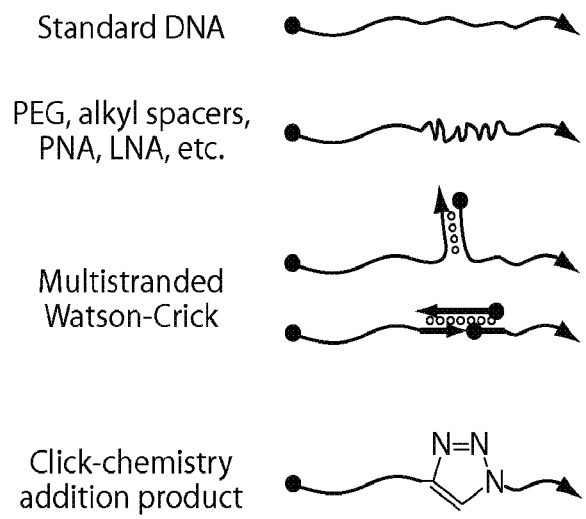
FIGS. 4A-4C depict several examples of a ssPrimer of the present disclosure having one of a variety of linkers between the priming domain and the specificity domain.
Figure 4C:
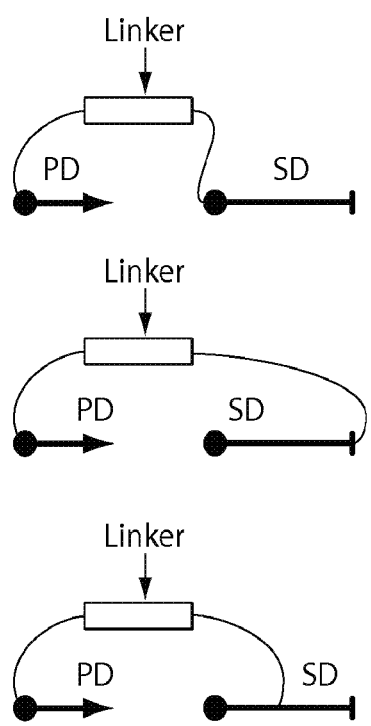
Figure 5:
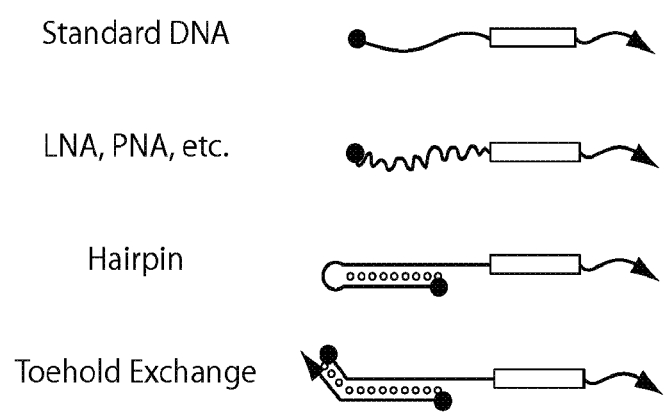
FIG. 5 depicts several embodiments of a ssPrimer of the invention having one of a variety of specificity domains, including a "toehold exchange" domain, which includes a competitive domain.

A linker that links a SD to a PD may be a chemical moiety, which may or may not be a continuous, covalently linked moiety. In some embodiments, a linker is attached to the 5' end of the SD if the SD is an oligonucleotide or a part of an oligonucleotide (FIG. 4C, top). In some embodiments, a linker is attached to the 3' end of the SD if the SD is an oligonucleotide or a part of an oligonucleotide (FIG. 4C, middle). In some embodiments, a linker is attached to a mid-region (e.g., through a nucleobase that is modified with a conjugation handle, such as a biotin-dT) of a SD (FIG. 4C, bottom). In some embodiments, a linker is attached to an additional, functional or non-functional, moiety, which is in turn attached to the 5' end, the 3' end, or to a mid-region of a SD. Similar variations with regard to the site of attachment on the SD are contemplated when a SD comprises other types of nucleobase-recognizing moieties (e.g., PNA and morpholino) (FIG. 5).

Figure 3:
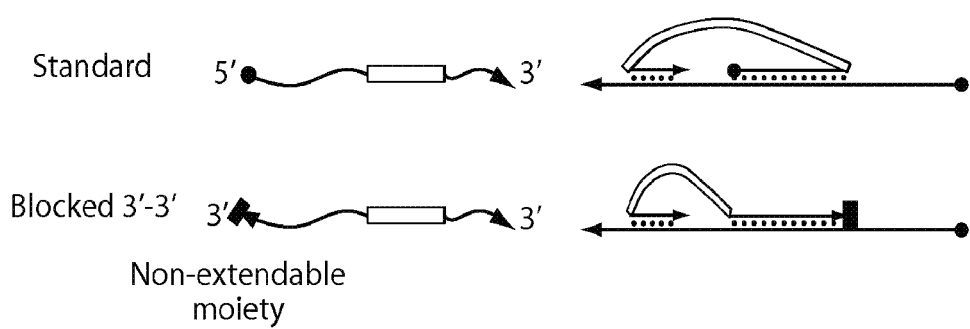
FIG. 3 depicts one example of a ssPrimer of the present disclosure having a non-extendable moiety at its 3' end.

In some embodiments, the SD is linked to the PD through a 5' to 3' linkage (FIG. 3, top), and in other embodiments, the SD is linked to the PD through a 5' to 5' linkage (FIG. 3, bottom). In some embodiments (e.g., with a 5' to 5' linkage), the 3' end of a SD and/or a CD is blocked (e.g., chemically to prevent extension) so that the 3' end cannot be extended by a DNA polymerase and/or degraded by an exonuclease. In some embodiments, the 3' end comprises a non-extendable nucleotide. In some embodiments, the non-extendable nucleotide may be a non-naturally occurring nucleotide or a dideoxy nucleotide. Examples of non-extendable nucleotides include, without limitation, isoC, isoG, deoxyuridine, dP, dZ, 3'-deoxyadenosine, 3'-deoxythymidine, 3'-deoxyguanosine, 3'-deoxycytidine, or otherwise naturally occurring nucleotide inserted in an inverted orientation (such as inverted dT), as well as nucleotides modified with at least one non-nucleotide moiety such as, for example, morpholinos, threose nucleic acids, phosphates, multi-carbon linkers, amino groups, thiol groups, azide groups and/or alkyne groups.

The nature of the linker may vary. For example, in some embodiments, the SD may be linked to the PD through a simple oligonucleotide. In such cases, the ssPrimer is a continuous oligonucleotide and a non-extendable nucleotide (e.g., non-naturally occurring nucleotide or nucleotide analogue such as isoC, IsoG and/or deoxyuridine) may be used to prevent polymerase read-through (FIG. 4A). Other nucleic acid analogues that may be used in accordance with the invention are described elsewhere herein.

In some embodiments, the linker is a chemical linker. For example, the linker may be, or may comprise, polyethylene glycol (PEG), an alkyl spacer, a peptide nucleic acid (PNA), or a locked nucleic acid (LNA) (FIG. 4A).

In some embodiments, the SD is linked to the PD using a chemical conjugation reaction (e.g., "click chemistry"). For example, the two domains may be linked to each other using an azide alkyne Huisgen cycloaddition reaction (FIG. 4) (Rostovstev, V. V., et al. *Angewandte Chemie International Edition* 41 (14): 2596-2599, 2002; Tornoe, C. W. et al. *Journal of Organic Chemistry* 67 (9): 3057-3064, 2002). In some embodiments, the SD and the PD may be linked to each other using other conjugation reactions involving amine, carboxyl, sulfhydryl, or carbonyl groups, or a combination of any of the foregoing reactions.

Figure 4B:
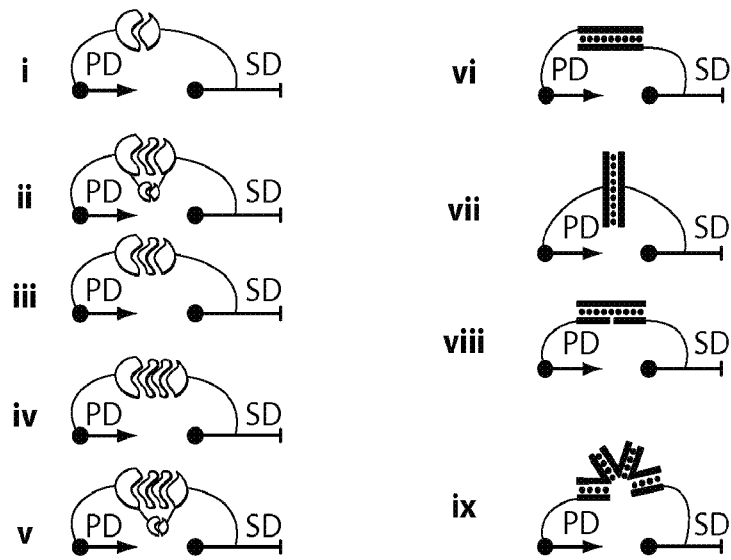

In some embodiments, a nucleic acid containing a SD and a nucleic acid containing a PD are linked to each other by hybridization to a single-stranded oligonucleotide or by hybridization to each other, or to a common group of oligonucleotides (FIG. 4B(vi)-4B(x)). Such configurations, in some embodiments, may be advantageous. For example, they may reduce the time and/or cost for optimization. When multiple (e.g. a number m) versions of SD and multiple (e.g. a number n) versions PD need to be tested in a combinatorial manner, the m versions of SD strands and n version of PD strands can be synthesized and, if necessary, purified separately. Then, they can be tested in a combinatorial manner. Thus, only m+n molecules are synthesized (and purified) and m×n combinations can be tested. This is in contrast with some linker designs that require all m×n combinations to be synthesized (and purified).

dsBlocker and dsBlocker Nucleic Acid Amplification

In other aspects of the invention, the problem of false-positive results is addressed by using a partially double-stranded primer and method of amplification.

In some embodiments, the problem of false-positive results is addressed by suppressing the amplification of the pseudo-target. One advantage of this approach is that the target nucleic acid may be enriched even when the exact sequence of the target is not fully known. For example, a target nucleic acid may have one of many possible mutations in a particular region of a gene and the mutant allele may be present as a rare allele in the presence of an excess of wild-type allele. In some embodiments, the length of the particular region may be 1 to 100 bases or base pairs. If a reagent can suppress the amplification of the wild-type sequence and allows all nucleic acid that differ from the wild-type sequence by as little as 1 nucleotide to be amplified, the amplification product can be subject to further analysis (e.g., sequencing) to identify the presence and the sequence of the mutant allele. It is ideal that this reagent has satisfactory performance in a wide range of experimental conditions. For example, for a given buffer condition, it is ideal that this reagent has satisfactory performance in a wide range of temperature (e.g., more than 5° C.). using a partially double-stranded primer and method of amplification.

Figure 6A:
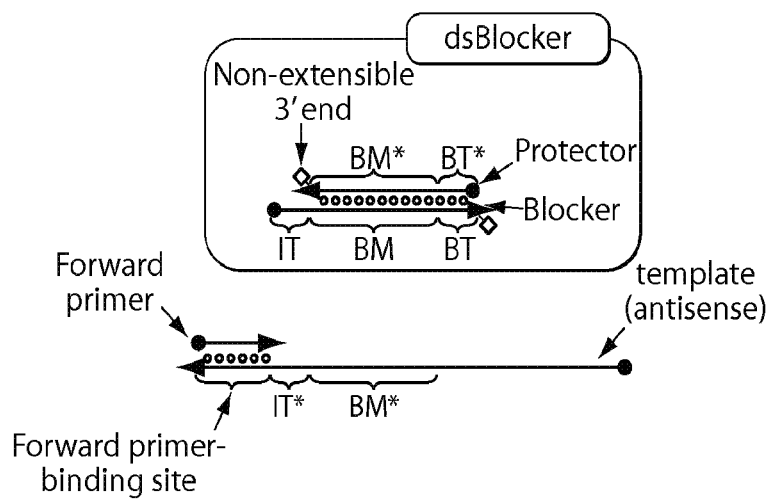
FIGS. 6A and 6B depict examples of dsBlockers of the present disclosure.

As used herein, a "dsBlocker" of the invention refers to an engineered partially double-stranded nucleic acid that comprises first ("blocker") and second ("protector") nucleic acid strands arranged into (i) one double-stranded pseudo-target non-specific domain (e.g., "BT"/"BT*"), (ii) one double-stranded pseudo-target specific domain (e.g., "BM"/"BM*"), and (ii) one single-stranded pseudo-target specific domain ("IT)" contributed to by the first nucleic acid strand, wherein the double-stranded pseudo-target non-specific domain has a standard free energy (ΔG) approximately equal to the standard free energy for the single-stranded pseudo-target specific domain bound to a rare target nucleic acid, and wherein the 3' end of the first nucleic acid strand and the 3' of the second nucleic acid strand are non-extendable (FIG. 6A).

Figure 6B:
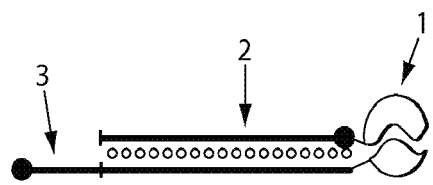

FIGS. 6A and 6B show examples of dsBlockers having blocker and protector strands that are contiguous nucleic acids. The blocker strand may be divided into three domains (ordered 5' to 3'): the initial toehold domain ("IT"), the branch-migration domain ("BM"), and the balancing toehold domain ("BT"). The protector strand may be divided into two domains (ordered 5' to 3'): the balancing toehold domain ("BT*"), which is complementary to the balancing toehold domain ("BT") of the blocker strand, and the branch migration domain ("BM*"), which is complementary to the branch migration domain ("BM") of the blocker strand. In some embodiments, the blocker strand is a contiguous nucleic acid. In some embodiments, the protector strand is a contiguous nucleic acid.

In some embodiments, the position of the initial toehold domain and the balancing toehold domain can be interchanged such that the initial toehold domain is located at the 3' end of the blocker strand and the balancing toehold domain is located at the 5' end of the blocker strand. In such embodiments, the BT* domain is located at the 3' end of the protector strand.

Figure 7:
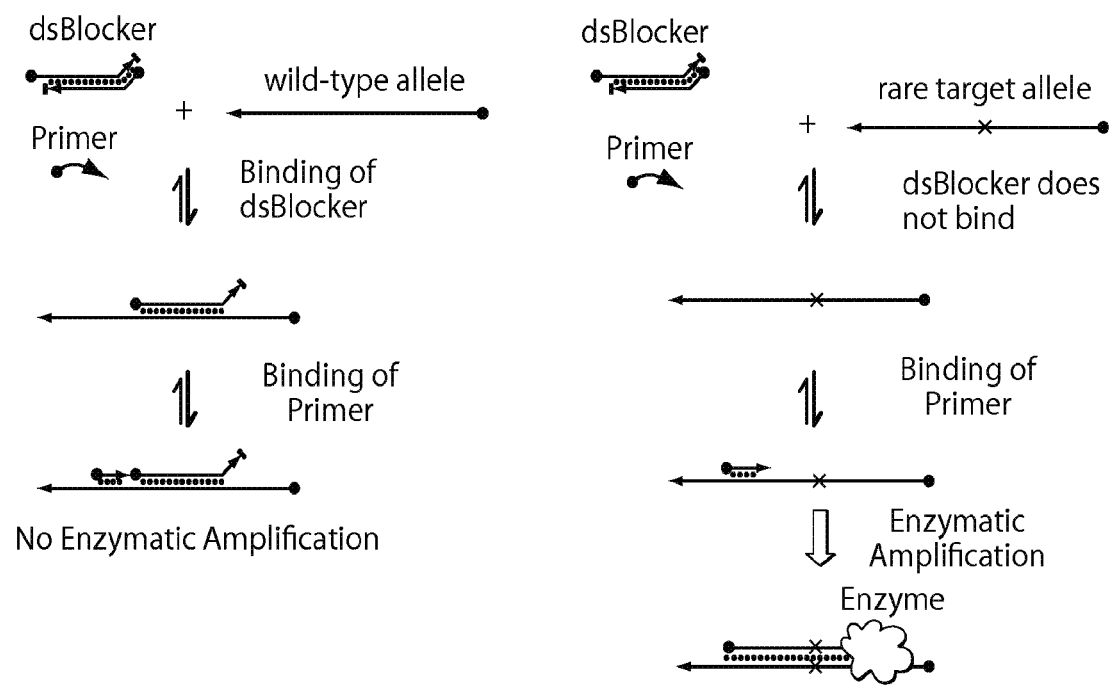
FIG. 7 depicts PCR amplification using a dsBlocker of the invention.

As shown in FIG. 7, when a dsBlocker designed to bind to a wild-type allele contacts a wild-type allele, the two strands of the dsBlocker dissociate as the strand that is complementary to the wild-type allele binds to a strand of the wild-type allele. By contrast, when the dsBlocker contacts a rare target allele, dissociation of the two strands of the dsBlocker is not favored, and the dsBlocker does not bind to the rare target allele. Thus, a nondiscriminatory primer binds to and is extended along the length of a strand of the rare target allele, resulting in preferential amplification of the rare target allele.

In some embodiments, dsBlocker nucleic acid amplification (nucleic acid synthesis/amplification using a dsBlocker) may be used to amplify a rare target allele. This is achieved by blocking amplification of the wild-type allele. In such embodiments, the IT-BM domains of the blocker strand may be engineered to be complementary to the wild-type allele (FIG. 7). The sequence of the BT domain may be designed according to several parameters to avoid unwanted hybridization. For example, the dsBlocker can be designed in the following processes.

Step 1. Choose the annealing temperature of the reaction. The annealing temperature should be high enough so that the pseudo-target strand does not form extensive secondary structure, but low enough so that typical primers have sufficient affinity to the primer-binding sites on the template. The annealing temperature is typically in the range of 55 to 70° C.

Step 2. Design IT and BM so that (a) the region on the pseudo-target strand that binds IT or BM encompasses the polymorphism site; (b) IT binds the pseudo-target strand weakly at the annealing temperature; (c) the IT-BM region of the blocker strand binds the pseudo-target strand stably 5° C. above the annealing temperature; (d) BM binds the pseudo-target strand weakly 10° C. above the annealing temperature.

Step 3. Generate a random sequence as candidate of BT so that the candidate BT binds its complementary strand with similar affinity as IT binds its complementary strand. For example, BT may have similar length and GC content as IT.

Step 4. Examine in silico whether BT erroneously binds the pseudo-target strand or the IT-BM region of the blocker strand. If so, repeat from Step 3. If not, use the candidate BT sequence.

The performance of dsBlocker can be further optimized by adjusting the length and/or GC content of the BT and/or BT* domains.

It is contemplated herein that the interaction between BT and BT* may be replaced by other forms of pseudo-target non-specific interactions, including indirect hybridization, a mixture of direct and indirect hybridization, protein-protein interaction, protein-small molecule interaction, magnetic interaction, electronic charge interaction, and the like.

In some embodiments, the free energy (ΔG) of binding between the BT domain and the BT* domain may be ~2 kcal/mole, or ~1 kcal/mole, higher than the ΔG of binding between the IT domain to pseudo-target allele (e.g., wild-type allele) at annealing temperature (i.e., IT domain: pseudo-target allele binding is stronger than BT domain: BT* domain binding). As a result, the ΔG of the blocker strand binding to the protector strand is ~2 kcal/mole, or ~1 kcal/mole, higher than the ΔG of the blocker strand binding to the pseudo-target allele (i.e., the blocker: pseudo-target allele binding is stronger than the blocker:protector binding). A single-nucleotide change (e.g., mutation, insertion or deletion) in the rare target allele may destabilize the blocker: target strand duplex by ~2 kcal/mole. Thus, when the dsBlocker of the present disclosure contacts pseudo-target allele, the pseudo-target allele (e.g., more than 50% of the pseudo-target allele) displaces the protector strand and binds to the blocker strand (e.g., at equilibrium). By comparison, when the dsBlocker contacts the rare target allele, which contains a mutation in the region complementary to the IT-BM domains of the blocker strand, only a small fraction of the rare target allele (e.g., less than 50% of the rare target allele) binds to the blocker strand because the target allele strand binds the Blocker strand less well than the blocker strand binding to the protector strand (e.g., displaces the protector strand and binds to the blocker strand). The single-nucleotide change (e.g., mutation, insertion or deletion) in the rare target allele typically destabilizes the blocker:rare target allele duplex by ~1 to ~4 kcal/mole. Thus, complementary binding between the blocker strand and the protector strand may be preferred over binding between the blocker strand and the rare target allele, where there is at least one nucleotide difference.

In some embodiments, the blocker and/or the protector strand comprises a non-extendable nucleotide at its 3' end. In some embodiments, the blocker and/or the protector strand comprises a nucleotide that blocks the addition of more nucleotides to the 3' end. In some embodiments, the blocker and/or the protector strand comprises a nucleotide that blocks the degradation of the 3' end. In some embodiments, the non-extendable nucleotide is a non-naturally occurring nucleotide or a dideoxy nucleotide. In some embodiments, the non-naturally occurring nucleotide is isoC, isoG or deoxyuridine, 3'-deoxyadenosine, 3'-deoxythymidine, 3'-deoxyguanosine, 3'-deoxycytidine and the like, or otherwise naturally occurring nucleotide inserted in an inverted orientation.

In some embodiments, methods of the present disclosure comprise contacting a pool of target and pseudo-target alleles, such as wild-type alleles, with (a) single-stranded primer, which is engineered to be complementary to a rare target allele of interest and, in some embodiments, to a pseudo-target allele, and (b) a dsBlocker, and extending the engineered single-stranded primer at its 3' end in a target-complementary manner in the presence of a polymerase. The blocker strand of the dsBlocker, which is engineered to be complementary to the wild-type allele, preferentially binds to the wild-type allele, thereby blocking extension of the single-stranded primer. In the same reaction, the single-stranded primer binds to the rare target allele and, without being blocked by the blocker strand, is extended. Thus, the rare target allele is preferentially amplified.

As discussed above, the blocker strand of the dsBlocker of the invention comprise at least three domains, including an initial toehold (IT) domain, a branch-migration (BM) domain, and a balancing toehold (BT) domain. The initial toehold domain and the branch migration domain have nucleic acid sequences that are complementary to nucleic acid sequences of the pseudo-target nucleic acid. The initial toehold domain and the branch migration domain are therefore able to base-pair with and thus form a complex with a sequence of a pseudo-target nucleic acid when the dsBlocker is contacted with a pseudo-target nucleic acid under appropriate hybridization conditions. The balancing toehold domain is rationally designed, and thus, the sequence of the balancing toehold domain is not designed to be complementary to a sequence in the pseudo-target nucleic acid sequence.

An initial toehold domain is complementary to (and thus hybridizes to) a sequence in the pseudo-target nucleic acid; however, an initial toehold domain does not hybridize to a protector strand. Thus, when the blocker strand is hybridized to the protector strand, the initial toehold domain may also hybridize to the target nucleic acid and/or the pseudo-target nucleic acid. An initial toehold domain may be positioned at the 3' end or the 5' end of the blocker strand (e.g., is an extension of the 3' end or 5' end of the blocker strand).

In some embodiments, such as in PCR, the primer is engineered so that, when the extension is stopped by the blocker strand, the partial extension product binds the pseudo-target template with a melting temperature at least 0.1° C. lower than the melting temperature of the complex formed by the pseudo-target strand and the blocker strand, so that during a process that the temperature is raised to a higher temperature (e.g., extension temperature and denaturing temperature), the partial extension product dissociates earlier than the blocker strand. It is to be understood that a DNA polymerase may extend a primer on a template at a temperature below the designated extension temperature, such as the annealing temperature.

In some embodiments, there is no gap on the template between the primer-binding site and the blocker strand-binding site. In such embodiments, the primer itself can be considered the partial extension product.

In some embodiments, the polymerase is a DNA polymerase with weak or no strand-displacement activity and no 5'-to-3' exonuclease activity (e.g., Pfu and PHUSION).

In some embodiments, the polymerase is a DNA polymerase with reported strand-displacement activity or reported 5'-to-3' exonuclease activity. In such embodiments, the enrichment may still be achieved if the polymerase does not completely displace or degrade the blocker strand during each step of PCR.

In some embodiments, the polymerase is a DNA polymerase with 3'-to-5' exonuclease activity (also known as the proofreading activity). In some embodiments, the polymerase is a high-fidelity DNA polymerase.

In some embodiments, an initial toehold domain is about 4 nucleotides to about 20 nucleotides in length, about 4 nucleotides to about 15 nucleotides in length, or about 4 nucleotides to about 10 nucleotides in length. In some embodiments, an initial toehold domain is 4, 5, 6, 7, 8, 9, 10, 11, 12, 13, 14, 15, 16, 17, 18, 19 or 20 nucleotides in length. In some embodiments, an initial toehold domain is greater than 20 nucleotides in length, including for example less than or about 25, 30, 35, 40, 45, 50, 55, 60, 65, 70, 75, 80, 85, 90, 95 100 or more nucleotides.

The branch migration domain is complementary to a sequence in the pseudo-target nucleic acid and to a sequence in the protector strand. Thus, when the blocker strand hybridizes to a pseudo-target nucleic acid, the branch migration domain hybridizes to the pseudo-target nucleic acid. When the blocker strand hybridizes to its protector strand, the blocker branch migration (BM) domain hybridizes to the protector branch migration (BM*) domain.

In some embodiments, a branch migration domain is no more than 200, 100, 75, 50, 40, 30, 25 or 20 nucleotides in length. In some embodiments, a branch migration domain is about 10 nucleotides to about 200 nucleotides in length. In some embodiments, a branch migration domain is about 10 nucleotides to about 150 nucleotides, about 10 nucleotides to about 100 nucleotides, or about 10 nucleotides to about 50 nucleotides in length. In some embodiments, a branch migration domain is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 or 200 nucleotides in length. In some embodiments, a branch migration domain may be more than 200 nucleotides in length, depending on the pseudo-target nucleic acid.

The balancing toehold domain of a blocker strand and a protector strand are complementary to each other (i.e., form a double-stranded nucleic acid) but are non-complementary to the pseudo-target nucleic acid (i.e., neither forms a double-stranded nucleic acid with the pseudo-target). Thus, when a blocker strand hybridizes to a pseudo-target nucleic acid, the blocker balancing toehold domain does not hybridize to the pseudo-target nucleic acid. When the blocker strand hybridizes to its protector strand, the blocker balancing toehold (BT) domain hybridizes to the protector balancing toehold domain (BT*).

The design of the balancing toehold domain is dependent on the design of the initial toehold domain. In some embodiments, the balancing toehold domain is designed such that the thermodynamic profile of the balancing toehold domain is comparable to that of the initial toehold domain. In some embodiments, the thermodynamic profile is based on a theoretic model, using for example, Mfold software available at the bioinfo website of Rensselaer Polytechnic Institute (RPI). The number and/or nature of nucleotides within a balancing toehold domain is comparable to that of the initial toehold domain. For example, if an initial toehold domain is comprised of about 40% A and T nucleotides and 60% G and C nucleotides, then the balancing toehold domain should also be comprised of about 40% A and T nucleotides and 60% G and C nucleotides. In some embodiments, the balancing toehold domain is designed such that no more than three consecutive nucleotides are complementary to a sequence on the pseudo-target nucleic acid to avoid binding of the balancing toehold domain to the pseudo-target nucleic acid.

In some embodiments, the length of a balancing toehold domain is short enough so that the blocker and protector spontaneously dissociate from each other. In some embodiments, a balancing toehold domain is about 4 nucleotides to about 20 nucleotides in length, about 4 nucleotides to about 15 nucleotides in length, or about 4 nucleotides to about 10 nucleotides in length. In some embodiments, a balancing toehold domain is 4, 5, 6, 7, 8, 9, 10, 11, 12, 13, 14, 15, 16, 17, 18, 19 or 20 nucleotides in length. In some embodiments, a balancing toehold domain is greater than 20 nucleotides, including for example less than about 25, 30, 35, 40, 45, 50, 55, 60, 65, 70, 75, 80, 85, 90, 95, 100 or more nucleotides. In some embodiments, the number of consecutive nucleotides that are complementary to a nucleotide sequence within the pseudo-target nucleic acid may be greater than three provided that the balancing toehold domain does not bind to the pseudo-target nucleic acid.

In some embodiments, the design of a balancing toehold domain does not depend on the concentration of the dsBlocker or the temperature at which the dsBlocker is formed/used. In some embodiments, a balancing toehold domain is designed such that the standard free energy for the reaction in which the protector strand is displaced from the blocker strand by the pseudo-target nucleic acid is close to zero kcal/mol. As used herein, "close to zero" means the standard free energy for the reaction is within 3.5 kcal/mol from 0 kcal/mol. In some embodiments, the standard free energy of this displacement reaction is within 3.5, 3.0, 2.5, 2.0, 0.9, 0.8, 0.7, 0.6, 0.5, 0.4, 0.3, 0.2, or 0.1 kcal/mol of zero kcal/mol.

In some embodiments, the design of a balancing toehold domain will be dependent on the dsBlocker concentration as well as reaction temperature. In such embodiments, a balancing toehold domain is designed so that the standard free energy for the reaction in which the protector strand is displaced from the blocker strand by the pseudo-target nucleic acid plus RT ln(c) is close to zero kcal/mol, where R is the universal gas constant (0.0019858775(34) kcal/mol·K), T is the temperature at which the dsBlocker is used, and c is the concentration at which dsBlocker is used. In some embodiments, the temperature at which the dsBlocker is used is about 273 K (0° C.), 277 K, 283 K, 288 K, 293K, 298 K, 303 K, 308 K, 313 K, 318 K, 323 K, 328 K, 333 K, 338 K, 343 K, 348 K, 353 K, 358 K or 363 K (90° C.). In some embodiments, the concentration (c) at which the dsBlocker is used is about 1 nM, 2 nM, 3 nM, 4 nM, 5 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, 100 nM, 125 nM, 150 nM, 175 nM, 200 nM, 225 nM, 250 nM, 300 nM, 350 nM, 400 nM, 450 nM, 500 nM, 600 nM, 700 nM, 800 nM, 900 nM or 1 µM. In some embodiments, the standard free energy of this displacement reaction plus RT ln(c) is within 3.5, 3.0, 2.5, 2.0, 0.9, 0.8, 0.7, 0.6, 0.5, 0.4, 0.3, 0.2 or 0.1 kcal/mol of zero kcal/mol.

In some embodiments, a dsBlocker may include one or more hairpin domains that connect the blocker strand to the protector strand. In some embodiments, the hairpin domain of a dsBlocker can be of any length. In some embodiments, the hairpin domain is more than 30, 25, 20, 19, 18, 17, 16, 15, 14, 13, 12, 11, 10, 9, 8, 7, 6, 5, 4 or 3 nucleotides in length. In some embodiments, the sequence of the hairpin is not complementary to a sequence of the pseudo-target nucleic acid.

In some embodiments, the hairpin domain has a poly-mononucleotide sequence, such as a poly-adenosine sequence, poly-deoxyadenosine sequence, a poly-5'-methyluridine sequence, a poly-thymidine sequence, a poly-guanosine sequence, a poly-deoxyguanosine sequence, a poly-cytidine sequence, a poly-deoxycytidine sequence, a poly-uridine sequence or a poly-deoxyuridine sequence. In some embodiments, the hairpin loop is or contains a chemical linker. In some embodiments, the chemical linker is polyethylene glycol, an alkyl spacer, a PNA or a LNA.

A dsBlocker of the invention may be one of at least two orientations. For example, in one orientation, the initial toehold domain is located at the 5' end, immediately adjacent to the blocker branch migration domain (i.e., no intervening nucleotides between the two domains), and the blocker balancing toehold domain is located at the 3' end, immediately adjacent to the blocker branch migration domain. In this orientation, the protector balancing toehold domain is at the 5' end of the protector strand, immediately adjacent to the protector branch migration domain. A nucleic acid sequence, domain or region is "immediately adjacent to," "immediately 5" or "immediately 3" to another sequence if the two sequences are part of the same nucleic acid and if no bases separate the two sequences. In another orientation, the initial toehold domain is located at the 3' end, immediately adjacent to the blocker branch migration domain, and the blocker toehold balancing domain is located at the 5' end, immediately adjacent to the blocker branch migration domain. In this orientation, the protector balancing toehold domain is at the 3' end of the protector strand, immediately adjacent to the protector branch migration domain.

In some embodiments, a dsBlocker comprises a blocker strand longer than the protector strand, the difference in length being dependent on the length of the initial toehold domain of the blocker strand. The lengths of the primers are designed such that hybridization of the blocker strand to the pseudo-target nucleic acid has a standard free energy ($\Delta G°$) close to zero. Release of the protector strand (from the dsBlocker) ensures that this hybridization reaction is entropically near-neutral and robust to concentration. As a result, in some embodiments, this reaction at room temperature (e.g., about 25° C. or about 298 K) parallels the specificity of hybridization achieved at near melting temperature across many conditions.

As intended herein, a $\Delta G°$ (change in standard free energy) "close to zero" refers to an absolute value (amount) less than or about 1 kcal/mol, less than or about 2 kcal/mol, less than or about 3 kcal/mol, or less than or about 3.5 kcal/mol. In some embodiments, the standard free energy of a balancing toehold domain or initial toehold domain is $>-1$ kcal/mol to $<1$ kcal/mol $>-3$ kcal/mol to $<3$ kcal/mol or $>-3.5$ kcal/mol to $<3.5$ kcal/mol.

dsBlockers of the invention may be prepared at a ratio of protector strand to blocker strand of about 2:1 to about 5:1, or 1:1 to about 5:1. In some embodiments, the ratio of protector strand to blocker strand is about 1:1, about 2:1, about 3:1, about 4:1, or about 5:1. In some embodiments, the ratio of protector strand to blocker strand is 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.2:1, 4.3:1, 4.4:1, 4.5:1, 4.6:1, 4.7:1, 4.8:1, 4.9:1, or 5:1. The dsBlockers may also be used together with excess protector strand in any of the assays or reactions described herein. The protector strand may be in about equal to or more than 1.01-, 2-, 5-, 10-, 20-, 50-, 100-, or 500-fold molar excess relative to the primer (e.g., blocker strand).

Simulating Rare Allele Enrichment Using dsBlocker in PCR

Methods of predicting thermodynamics of nucleic hybridization, and dynamic programming algorithms for computing minimum free energy (MFE) structure and partition function, are well developed (SantaLucia, J., et al. *Annu Rev Biophys Biomol Struct,* 33:415-440, 2004; Dirks, R. M., et al. *SIAM Rev,* 49(1):65-88, 2007). For a given hybridization reaction, the standard Gibson free energy change at a given temperature can be calculated using the equation $\Delta G°=\Delta H°-T\cdot\Delta S°$. With this knowledge, several publicly available software programs (e.g., HyTher, Mfold, UNAfold and NUPACK) can be used to predict the $\Delta G°$ and equilibrium concentration of each nucleic acid strand among a plurality (e.g., mixture/combination) of nucleic acids.

In the embodiments where the pseudo-target non-specific interaction pair is a pair of complementary oligonucleotides (FIG. 6A), the performance of the dsBlocker can be estimated using the following procedure. Without being bound by theory, given the buffer condition and the reaction temperature, the equilibrium concentrations of all possible hybridization products and intermediates for a nucleic acid hybridization reactions that involve the dsBlocker can be calculated using the predicted $\Delta G°$ values for all interactions. For example, for hybridization between a pseudo-target template nucleic acid and the blocker strand, at equilibrium:

$$\frac{[\text{template:blocker strand}](1M)}{[\text{template}][\text{blocker strand}]} = e^{-\Delta G°/RT} \qquad (4)$$

where [template:blocker strand], [template] and [blocker strand] are equilibrium concentrations; T is the annealing temperature (Kelvin temperature), and $\Delta G°$ is the standard free energy change of the hybridization reaction.

For a reaction mixture containing multiple strands, the $\Delta G°$ value for each pair of partially or fully complementary strands can be predicted, thus an equation that governs the ratios among equilibrium concentration, such as equation (4), can be established. This set of equations plus the equations that reflect conservation of material establish an equation set that has a unique solution. The solution can be computed either analytically or numerically.

At the exponential phase of a nucleic acid amplification reaction (e.g., polymerase chain reaction (PCR)), the concentration of template (either target or pseudo-target) is very low (<5% of the concentration of the blocker strand, or <1% of the concentration of the blocker strand). The ratio of [template]/[template:blocker] is independent of the template concentration and is consistent in each thermocycle of a nucleic acid amplification reaction. Additionally, when a primer is designed to bind to the region on the template downstream of the region on the template that the blocker strand binds, the primer cannot be fully extended if the blocker strand of the dsBlocker is bound to the template. Thus, the template strands that are not bound by the blocker strand of the dsBlocker are assumed to be copied into the complementary strand by the primer and the polymerase; whereas the template strands that are bound by the blocker strand of the dsBlocker are assumed to be not copied into the complementary strand by the primer and the polymerase. The extension efficiency (EE) of an amplification cycle, defined as the fraction of a template that is copied by a primer in the cycle of the exponential amplification reaction, can be calculated using the following equation:

$$EE = [\text{template}]/([\text{template}] + [\text{template:blocker strand}]) = \quad (5)$$

$$\frac{[\text{template}]/[\text{template:blocker strand}]}{[\text{template}]/[\text{template:blocker strand}] + 1}$$

When the component of a dsBlocker nucleic acid amplification reaction, the sequence and concentration of each component, the salinity and the annealing temperature are specified, the EE value (which is constant for each round of exponential amplification) can be calculated.

The single-stranded primer that primes the pseudo-target template strand may be referred to a forward primer, and this forward primer is blocked when the pseudo-target template strand is bound by the blocker strand of a dsBlocker. The pseudo-target template strand that binds the blocker strand of the dsBlocker may be referred to as the antisense strand. The primer that binds the antisense strand may be referred to a forward primer, and this forward primer is blocked when the antisense strand is bound by the blocker strand of a dsBlocker. The pseudo-target template strand that is complementary the antisense strand may be referred to as the sense strand. A primer that is extended on the sense strand may be referred to as a reverse primer. Even though the protector strand of a dsBlocker can hybridize to the sense strand of the pseudo-target template, this hybridization is designed to be unstable at the annealing or extension temperature.

The following definitions apply:

(1) S(0) and AS(0) are the initial concentrations of the sense strand and the antisense strand of the pseudo-target template, respectively;

(2) S(n) and AS(n) (n∈N$^+$) are the concentration of the sense strand and the antisense strand after the nth cycle.

Thus:

$$S(n)=S(n-1)+AS(n-1)\cdot EE \quad (6a)$$

$$AS(n)=AS(n-1)+S(n-1)\cdot 1 \quad (6b)$$

'Fold-amplification' after n cycles is defined as [S(n)+AS(n)]/[S(0)+AS(0)].

The above theories may be used to compare the potential performance of dsBlocker nucleic acid amplification of the invention and traditional wild type-blocking PCR (Dominguez, P. L. et al. *Oncogene*, 24(45): 6830-4, 2005). The following set of sequences is used as an example:

The antisense strand of pseudo-target template comprises a sequence of 5'-ttcatcagtgatcaccgcccATCCGACGCTATTTGTGCCG[A]TATCTAAGCctattgagtatttc-3' (SEQ ID NO:1). The antisense strand of rare target template comprises a sequence of 5'-ttcatcagtgatcaccgcccATCCGACGCTATTTGTGCCG[C]TATCTAAGCctattgagtatttc-3' (SEQ ID NO:2). For both sequences, the region that can hybridize to the blocker strand of the dsBlocker is shown in upper case letters, and the base that varies between the pseudo-target and target is enclosed by brackets.

Traditional Wild Type-Blocking PCR.

Figure 8:
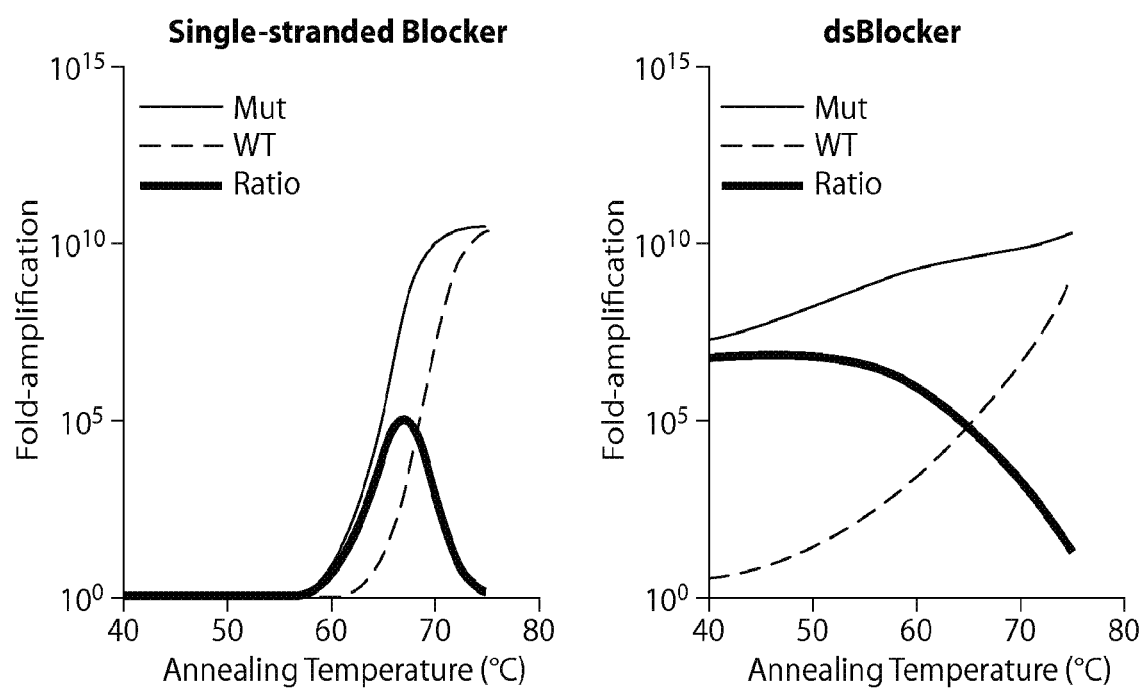
FIG. 8 shows graphs demonstrating a theoretical upper bound of the selectivity of wild type-blocking PCR (left) and dsBlocker PCR (right). Fold-amplification after 35 cycles was plotted as a function of annealing temperature for both mutated (thin continuous lines) and wild-type template (thin dashed lines). The selectivity of amplification versus annealing temperature is shown in thick lines.

A single-stranded oligonucleotide blocker (also known as 'clamp') was designed to hybridize to the antisense strand of pseudo-target template to block extension of the forward primer. The sequence of single-stranded oligonucleotide blocker is as follows: 5'-GCTTAGATA[T]CGGCACAAATAGCGTCGGAT-3' (SEQ ID NO:3), where the nucleotide that differentiates the pseudo-target and the target template is enclosed by brackets. The concentration of the single-stranded oligonucleotide blocker was set to be 100 nM. Using established thermodynamic parameters (SantaLucia, J., et al. 2004; Dirks, R. M., et al. 2007) at a salinity of 50 mM [Na$^+$], 5.7 mM [Mg$^{2+}$], the standard enthalpy and entropy change for the hybridization reactions between (a) pseudo-target strand and the single-stranded oligonucleotide (ΔH°=−238.90 kcal/mole, ΔS°=−660.72 e.u.) and (b) target strand and the single-stranded oligonucleotide (ΔH°=−222.40 kcal/mole, ΔS°=−618.90 e.u.) was calculated. Using the above equations, the fold-amplification after 35 cycles versus the annealing temperature for both pseudo-target (FIG. 8A, left, thin dashed line) and target template (FIG. 12A, thin solid line) was plotted. The ratio between 'fold-amplification after 35 cycles for target template' and 'fold-amplification after 35 cycles for pseudo-target template' for different annealing temperatures was also calculated (FIG. 8A, left, thick solid line). This ratio is defined as 'selectivity of amplification.' It is clear that significant discrimination (selectivity of ~10$^5$) is achieved only when the annealing temperature is near the melting temperature ($T_m$) of the template:oligo duplex. When the annealing temperature is below this $T_m$, both pseudo-target and target templates are blocked, and when the annealing temperature is above this $T_m$, neither pseudo-target nor target template is blocked. Either case results in poor selectivity. One consequence of such behavior of the single-stranded oligonucleotide blocker is that the blocker cannot to be very long (e.g., it cannot be longer than 15 to 25 bases, depending on the chemical nature and sequence of the blocker). For example, a $T_m$ of greater than about 80° C. would not result in efficient primer binding and polymerase extension. Thus, the "scope" of target/pseudo-target sequence is limited with wild type-blocking PCR.

dsBlocker Amplification.

The presence of the balancing toehold domains and the protector strand permits ultra-specific hybridization between the pseudo-target template and the blocker strand at temperature substantially lower than the $T_m$ of the template:blocker hybridization (Zhang, D. Y., et al. *Nat Chem*, 4(3):208-214, 2012). Thus, the blocker strand of a dsBlocker, in some embodiments, may be designed to be longer than the single-stranded oligonucleotide primer of a traditional wild type-blocking PCR. Further, the dsBlockers of the invention, in some embodiments, permit high selectivity of nucleic acid amplification across a wide range of temperatures. However, this phenomenon was only tested at temperatures below 37° C. which are not suitable for PCR. Moreover, it was not obvious how the sequence specificity in one binding step translates to the selectivity of an exponential amplification. To estimate the performance of dsBlocker amplification, a dsBlocker of the invention was designed to have the following sequence: 5'-GCTTAGATA[T]CG|GCACAAATAGCGT CGGAT(GGGCG)tcttcttca-3' (SEQ ID NO:4), where the balancing toehold (BT) domain is shown in lower case, and the initial toehold (IT) domain and the branch migration (BM) domain are shown in upper case on the left and right side of the symbol '|', respectively. The base that differentiates the pseudo-target and the target template is enclosed by brackets. The sequence in the parentheses was not present in the single-stranded oligonucleotide primer, described above, but is nevertheless derived from the target sequence and is part of the branch migration domain. Thus, mutations in this region of the target can be identified by the dsBlocker of the invention but not the traditional single-stranded oligonucleotide primer (i.e., the dsBlocker has a "broader scope" of target sequence).

The protector strand of the dsBlocker was designed to have the following sequence: 5'-tgaagaaga(CGCCC)ATCCGACGCTATTTGTGC-3' (SEQ ID NO:5), where the balancing toehold domain and the branch migration domain are shown in lower and upper cases, respectively. The sequence in parentheses is complementary to the sequence in parentheses of the blocker strand. The concentrations of the blocker strand and the protector strand were set to be 100 nM and 150 nM, respectively. Using the above equations, the fold-amplification after 35 rounds for the pseudo-target (FIG. 8, right, thin dashed line) and target (FIG. 8, right, thin solid line) template at different annealing temperature was calculated. The selectivity of amplification versus annealing temperature (FIG. 8, right, thick solid line) was also plotted. It is clear from this analysis that optimal selectivity can be achieved with the dsBlocker of the invention under a surprisingly wide range of annealing temperatures that are suitable for PCR, due to the effect of entropy cancellation.

Temperature Barcoded Hydrolysis Probe

Provided herein are methods and compositions for barcoding multiple ssPrimers by melting temperature and performing multiplexed amplification and/or detection reactions. For example, in the design shown in FIG. 13, two sets of nucleic acids are used to amplify two different targets. Both sets of nucleic acids comprise a ssPrimer. For each ssPrimer, the SD and PD are linked via hybridization of hybridization domains designated HD and HD*, respectively. The length of each hybridization domain may vary. In some embodiments, the length of each hybridization domain is 4 to 150 nucleotides (or nucleotide base pairs). In some embodiments, the length of each hybridization domain is 4 to 10, 4 to 20, 4 to 30, 4 to 40 or 4 to 50 nucleotides. In some embodiments, the length of each hybridization domain is 4, 5, 6, 7, 8, 9, 10, 11, 12, 13, 14, 15, 16, 17, 18, 19, 20, 21, 22, 23, 24, 25, 26, 27, 28, 29, 30 or more nucleotides. The nucleic acid strand containing the SD is labeled with a signal-generating moiety (e.g., a fluorophore ("F")) and a first signal-modulating moiety (e.g., fluorescence quencher ("Q1")). The signal-generating moiety is attached in non-SD region (region of the nucleic acid strand that is not the SD), and the first signal-modulating moiety is attached in the SD. There is an additional signal-modulating moiety (e.g., fluorescence quencher ("Q2")) attached to the HD* of the PD strand. When such a ssPrimer is used in PCR with a DNA polymerase that has 5'-to-3' exonuclease activity (e.g., Taq), the 5' end of SD will be degraded as the PD is extended to copy the template. Therefore, the first signal-modulating moiety (e.g., Q1) attached to the SD is physically separated from the signal-generating moiety (e.g., F). This separation results in increased signal (e.g., fluorescence signal) when the signal of the reaction mixture is measured at the temperature about or above the melting temperature of the duplex formed by HD and HD*, allowing the amplification progress to be monitored during an amplification (e.g., PCR) reaction (e.g., using real-time PCR).

Figure 13:
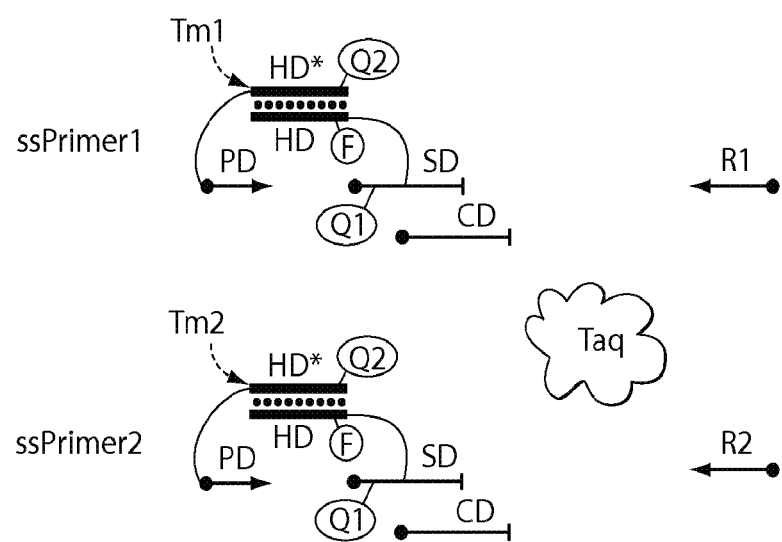
FIG. 13 depicts an example of a temperature-barcoded, signal-generating ssPrimer.

In some embodiments, an amplification (e.g., PCR) product is subjected to melting analysis. For example, if a target nucleic acid is amplified, a melting curve (fluorescence versus temperature) that reflects the hybridization of the HD and HD* of the ssPrimer designed to amplify the target should be observed because the HD* carries the signal-modulating moiety (e.g., Q2). The peak in the derivative of the melting curve would reflect the melting temperature of the duplex formed by HD and HD*. Because the sequence of the HD and HD* domains can be designed arbitrarily, the two HD domains of the two ssPrimers can be designed to have different melting temperatures (e.g., Tm1 and Tm2 as shown in FIG. 13). In this way, for example, the successful amplification of a target would result in the presence of a signature peak or valley in the derivative of the melting curve. Thus, more than one target can be distinguished using signal-generating moiety(ies) (e.g., fluorophore(s)) of only one color. Similarly, more than two ssPrimers with distinctive melting curves for HD and HD* can be used in one PCR reaction. In some embodiments, ssPrimers labeled with signal-generating moieties (e.g., fluorophores) of different colors are used in a single PCR reaction.

Figure 14A:
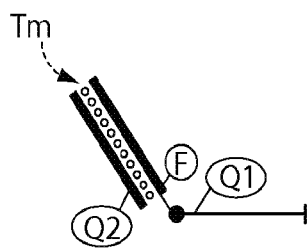
FIGS. 14A-14C depict an example of temperature-barcoded hydrolysis probe (TBHP).
Figure 14B:
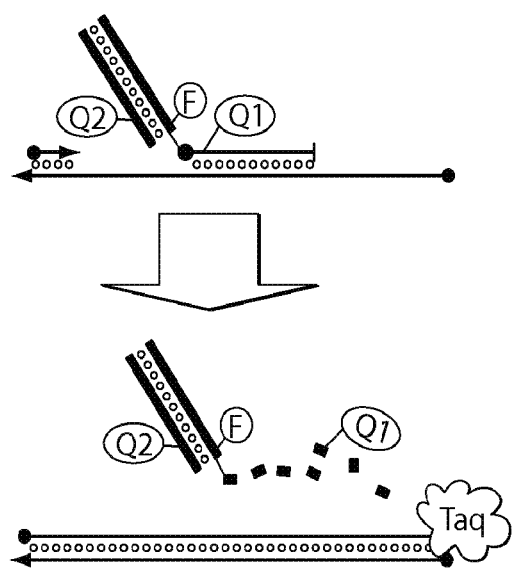
Figure 14C:
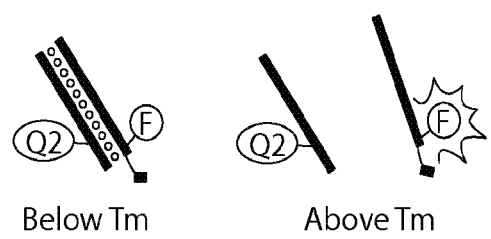

Barcoding with melting temperature, as provided herein, can be applied, in some embodiments, to designs of hydrolysis probes in general. FIGS. 14A-14C show an example of the Temperature Barcoded Hydrolysis Probe (TBHP). This TBHP comprises a Probe Strand and a Free Quencher Strand. The Probe Strand contains (1) a first domain having a length of 5 to 60 nucleotides (e.g., 5, 6, 7, 8, 9, 10, 15, 20, 25, 30, 35, 40, 45, 50, 55 or 60 nucleotides), having a sequence that is arbitrarily designed (e.g., analogous to the HD described above) and is attached to a fluorophore ("F"), and (2) a second domain having a length of 5 to 60 nucleotides (e.g., 5, 6, 7, 8, 9, 10, 15, 20, 25, 30, 35, 40, 45, 50, 55 or 60 nucleotides), having a sequence complementary or partially complementary to a portion of a target strand (analogous to the SD described above), and is linked to a first quencher ("Q1" in FIG. 14A). In some embodiments, a Free Quencher Strand comprises a domain complementary or partially complementary to the first domain of a Probe Strand and is attached to a second quencher ("Q2" in FIG. 13A). In some embodiments, a plurality of TBHPs may be used to detect a plurality of nucleic acid targets if the Probe Strands and the corresponding Free Quencher Strands have different melting profiles.

A method of using a plurality of TBHPs to detect a plurality of nucleic acid targets may comprise contacting the TBHPs and the targets in the presence of at least one enzyme that has base pairing-dependent nuclease activity. The nuclease activity is used to separate the first quencher from the fluorophore.

In some embodiments, the base pairing-dependent nuclease activity is endonuclease activity. In some embodiments, the endonuclease activity is RNaseH activity.

In some embodiments, the base pairing-dependent nuclease activity is exonuclease activity. In some embodiments, the exonuclease activity is double strand-specific 5'-to-3' exonuclease activity. In some embodiments, the exonuclease activity is double strand-specific 3'-to-5' exonuclease activity.

In some embodiments, the enzyme that has base pairing-dependent nuclease activity is a DNA polymerase. For example, many DNA polymerases (such as Taq) exhibit double strand-specific 5'-to-3' exonuclease activity, and many DNA polymerases (such as Pfu, Phusion and KOD) exhibit double strand-specific 3'-to-5' exonuclease activity, which is also known as proofreading activity.

In some embodiments, a composition comprising at least one (e.g., 1, 2, 5, 10, 15, 20, 30, 40, 50 or more) TBHP supports both amplification and detection of at least one nucleic acid target (e.g., 1, 2, 5, 10, 15, 20, 30, 40, 50 or more). For example, a TBHP may be used in PCR or real-time PCR in the same manner as conventional hydrolysis probe (e.g., a TaqMan probe) is used. In some embodiments, TBHP is used in a PCR mixture that also contains a set of primers and a DNA polymerase with 5'-to-3' exonuclease activity such as Taq, which can partially or complete degrade the Q1-bearing domain as a primer is extended (FIG. 14B). Multiple TBHPs, wherein the Probe Strands and their corresponding Free Quencher Strands have distinct melting temperatures, can be used, for example, in a multiplex PCR to identify the presence of multiple targets.

In some embodiments, after contacting TBHPs and the nucleic acid targets in the presence of at least one enzyme with base pairing-dependent nuclease activity (e.g., wherein the contacting may comprise a single-temperature incubation and/or 5 to 100 cycles of PCR amplification in an appropriate buffer with an appropriate incubation and/or thermo-cycling program), the reaction product can be subjected to melting analysis, where the temperature is changed from a high temperature (e.g., 80° C. to 100° C., such as 90° C.) to a lower temperature (e.g., 20° C. to 40° C., such as 30° C.) while the fluorescence signal of the reaction is measured at multiple temperatures (FIG. 8C). In some embodiments, the first derivative of the fluorescence signal over temperature (dF/dT or −dF/dT, where dT is an increment of temperature and dF is the change of fluorescent signal over the said increment of temperature) versus temperature (also known as the derivative of melting curve) can be plotted in a figure, wherein the temperature at which a peak or valley of the plot is observed reflects the melting temperature of a duplex comprising a Probe Strand and the corresponding Free Quencher Strand. If a particular target is present, a signature peak or valley in the said figure corresponding to the TBHP designed to detect the target is observed, wherein the temperature at which the peak or valley is observed reflects the melting temperature of the duplex formed by the Probe Strand and the Free Quencher Strand of the said TBHP.

In some embodiments, a Probe Strand is a continuous oligonucleotide. In some embodiments, a Probe Strand comprises at least one non-nucleotide moiety. In some embodiments, a Probe Strand is formed by multiple molecules that interact with non-covalent interactions.

In some embodiments, a Probe Strand and a Free Quencher Strand can be covalently linked to form one continuous molecule. In some embodiments, a continuous molecule is a continuous nucleic acid.

A TBHP refers, in some embodiments, to a set of oligonucleotides that comprises (1) a first domain having a sequence that is not restricted by the target sequence and is attached to a signal-generating moiety, (2) a second domain that is complementary or partially complementary to a portion of a target strand and is attached to a first signal-modulating moiety that can affect the signal generated by the said signal-generating moiety, and (3) a third domain that is complementary or partially complementary to the first domain and is attached to a second signal-modulating moiety that can affect the signal generated by the said signal-generating moiety, wherein the signal-generating moiety and the first signal-modulating moiety are separated by at least one phosphodiester bond. When a TBHP is used with at least one enzyme with base pairing-dependent nuclease activity, the binding of the second domain to the target strand can cause the phosphodiester bond to be hydrolyzed by the enzyme, resulting in separation of the signal-generating moiety and the first signal-modulating moiety. Any two of the three domains described above may be linked by a variety of covalent and non-covalent bonds or interactions. In some embodiments, the third domain may interact with the first domain solely via their complementarity and no other interactions. The signal-modulating moiety and signal-modulating moieties, in some embodiments, can be attached to the corresponding domains via a variety of covalent and non-covalent bonds or interactions.

A "signal-generating moiety" refers to any moiety that generates a signal. Examples of signal-generating moieties include fluorophores and other moieties that can re-emit light upon light excitation. Examples of fluorophores for use in accordance with the present disclosure include, without limitation, xanthene derivatives (e.g., fluorescein, rhodamine, Oregon green, eosin, and Texas red), cyanine derivatives (e.g., cyanine, indocarbocyanine, oxacarbocyanine, thiacarbocyanine, and merocyanine), naphthalene derivatives (e.g., dansyl and prodan derivatives), coumarin derivatives, oxadiazole derivatives (e.g., pyridyloxazole, nitrobenzoxadiazole and benzoxadiazole), anthracene derivatives (e.g., anthraquinones, including DRAQ5, DRAQ7 and CyTRAK Orange), pyrene derivatives (e.g., cascade blue), oxazine derivatives (e.g., Nile red, Nile blue, cresyl violet and oxazine 170), acridine derivatives (e.g., proflavin, acridine orange and acridine yellow), arylmethine derivatives (e.g., auramine, crystal violet and malachite green), and tetrapyrrole derivatives (e.g., porphin, phthalocyanine and bilirubin). Other signal-generating moieties are contemplated herein.

A "signal-modulating moiety" refers to any moiety that modulates (e.g., quenches) a signal generated by a signal-generating moiety. In some embodiments, a signal-modulating moiety decreases fluorescence signal intensity. Examples of quenchers include, without limitation, dark quenchers (e.g., dyes with no native fluorescence such as dabsyl, dark hole quenchers, Qx1 quenchers, Iowa black FQ, Iowa Black RQ, IRDye QC-1), molecular oxygen, iodide ions, chloride ions, acrylamide. Other signal-modulating moieties are contemplated herein.

Nucleic Acid Amplification Conditions

The methods of the invention are directed generally to synthesizing, and thereby amplifying, nucleic acids (e.g., rare target nucleic acids). In some embodiments, the temperature of the reaction solutions may be sequentially cycled between a denaturing state, an annealing state, and an extension state for a predetermined number of cycles. The actual times and temperatures can be enzyme, primer (e.g., ssPrimer, dsBlocker), and target/pseudo-target dependent.

For any given reaction, denaturing states may range from about 75° C. to about 100° C. The annealing temperature and time can influence the specificity and efficiency of primer and other molecules (e.g., ssPrimer, dsBlocker) binding to a particular locus within a target or pseudo-target nucleic acid and may be important for particular synthesis reactions.

For any given reaction, annealing states may range from about 20° C. to about 75° C., or about 20° C. to about 85° C. In some embodiments, the annealing state may be performed at about 20° C. to about 25° C., about 25° C. to about 30° C., about 30° C. to about 35° C., or about 35° C. to about 40° C., about 40° C. to about 45° C., about 45° C. to about 50° C., about 50° C. to about 55° C., about 55° C. to about 60° C., about 60° C. to about 65° C., about 65° C. to about 70° C., about 70° C. to about 75° C., about 75° C. to about 80° C., about 80° C. to about 85° C. In some embodiments, the annealing state may be performed at room temperature (e.g., 20° C. or 25° C.). In some embodiments, the annealing state may be performed at a temperature of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C. or 50° C.

Extension temperature and time may impact the allele product yield and are understood to be an inherent property of the enzyme used. For a given enzyme, extension states may range from about 60° C. to about 75° C. It is to be understood that the polymerase may be able to extend the primer in states other than the extension state of PCR.

In some embodiments, the polymerase used may have strand displacement activity. Examples include Vent polymerase, Bsm polymerase, Bst polymerase, Csa polymerase and 96-7 polymerase. In any of the embodiments relating to the dsBlocker and dsBlocker nucleic acid amplification methods, any DNA or RNA polymerase (enzyme that catalyzes polymerization of nucleotides into a nucleic acid strand) may be used, including thermostable polymerases and reverse transcriptases (RTases). Examples include *Bacillus stearothermophilus* pol I, *Therms aquaticus* (Taq) pol I, *Pyrccocus furiosus* (Pfu), *Pyrococcus woesei* (Pwo), *Thermus flavus* (Tfl), *Therms thermophilus* (Tth), *Thermus litoris* (Tli) and *Thermotoga maritime* (Tma). These enzymes, modified versions of these enzymes, and combination of enzymes, are commercially available from vendors including Roche, Invitrogen, Qiagen, Stratagene, and Applied Biosystems. Representative enzymes include PHUSION® (New England Biolabs, Ipswich, Mass.), Hot MasterTaq™ (Eppendorf), PHUSION® Mpx (Finnzymes), PyroStart® (Fermentas), KOD (EMD Biosciences), Z-Taq (TAKARA), and CS3AC/LA (KlenTaq, University City, Mo.).

Salts and buffers include those familiar to those skilled in the art, including those comprising $MgCl_2$, and Tris-HCl and KCl, respectively. Buffers may contain additives such as surfactants, dimethyl sulfoxide (DMSO), glycerol, bovine serum albumin (BSA) and polyethylene glycol (PEG), as well as others familiar to those skilled in the art. Nucleotides are generally deoxyribonucleoside triphosphates, such as deoxyadenosine triphosphate (dATP), deoxycytidine triphosphate (dCTP), deoxyguanosine triphosphate (dGTP), and deoxythymidine triphosphate (dTTP), and are also added to a reaction adequate amount for amplification of the target nucleic acid.

Target and Pseudo-Target Nucleic Acid Molecules

A "target" and/or "pseudo-target" may be a single-stranded (ss) or double-stranded (ss) nucleic acid. A single-stranded target/pseudo-target, the strand of a double-stranded target/pseudo-target that binds to the SD/PD of the ssPrimer or the IT/BM domain of the dsBlocker, or the strand of the double-stranded amplification product that binds to the SD/PD of the ssPrimer or the IT/BM domain of the dsBlocker are referred to as the target/pseudo-target strand. In some embodiments, a target nucleic acid is a rare allele. An "allele" is one of a number of alternative forms of the same gene or same genetic locus. Alleles may differ from each other by a single nucleotide in the form of alteration, insertion or deletion. A "wild-type allele," as used herein, may refer to the major (more or most common) allele in a given plurality of nucleic acids. Conversely, a "rare allele," may refer to the minor (less or least common) allele in the same plurality of nucleic acids. For example, in some embodiments, a plurality of nucleic acids encoding gene X may contain 10- to 1,000,000-fold, or 100- to 1,000,000-fold, more of allele $X_A$ than allele $X_B$, where allele $X_A$ and allele $X_B$ differ by a single nucleotide. Allele $X_A$ is considered to be the "wild-type allele," while allele $X_B$ is considered to be the "rare allele." A "pseudo-target" has a sequence that is similar to a target sequence, differing by one, two, three, four or five nucleotides. Thus, a "wild-type allele" and a "pseudo-target allele" may be used interchangeably, in some embodiments. While a target nucleic acid is often referred to herein in terms of gene/allele identification, the invention is not limited to the detection of genes/alleles. Other nucleic acids may be detected/amplified in accordance with the various aspects and embodiments of the invention.

Target and/or pseudo-target nucleic acids may be, for example, DNA, RNA, or the DNA product of RNA subjected to reverse transcription. In some embodiments, a target and/or pseudo-target may be a mixture (chimera) of DNA and RNA. In some embodiments, a target and/or pseudo-target may comprise artificial nucleic acid analogs, for example, peptide nucleic acids (Nielsen et al. *Science* 254(5037): 1497-500 (1991)) or locked nucleic acids (Alexei et al. *Tetrahedron* 54(14): 3607-30 (1998)). In some embodiments, a target and/or pseudo-target may be naturally occurring (e.g., genomic DNA) or it may be synthetic (e.g., from a genomic library). As used herein, a "naturally occurring" nucleic acid sequence is a sequence that is present in nucleic acid molecules of organisms or viruses that exist in nature in the absence of human intervention. In some embodiments, a target and/or pseudo-target is genomic DNA, messenger RNA, ribosomal RNA, micro-RNA, pre-micro-RNA, pri-micro-RNA, viral DNA, viral RNA or piwi-RNA. In some embodiments, a target and/or pseudo-target nucleic acid is a nucleic acid that naturally occurs in an organism or virus. In some embodiments, a target and/or pseudo-target nucleic acid is the nucleic acid of a pathogenic organism or virus. In some embodiments, the presence or absence of a target and/or pseudo-target nucleic acid in a subject is indicative that the subject has a disease or disorder or is predisposed to acquire a disease or disorder. In some embodiments, the presence or absence of a target nucleic acid in a subject is indicative that the subject will respond well or poorly to a treatment, such as a drug, to treat a disease or disorder.

The term nucleic acid refers to a polymeric form of nucleotides of any length, either deoxyribonucleotides or ribonucleotides, or analogs thereof. Nucleic acids may have any three-dimensional structure, and may perform any function. The following are non-limiting examples of nucleic acids: coding or non-coding regions of a gene or gene fragment, loci (locus) defined from linkage analysis, exons, introns, messenger RNA (mRNA), transfer RNA, ribosomal RNA, ribozymes, cDNA, recombinant nucleic acids, branched nucleic acids, plasmids, vectors, isolated DNA of any sequence, isolated RNA of any sequence, nucleic acid probes, and primers. A nucleic acid may comprise modified nucleotides, such as methylated nucleotides and nucleotide analogs. If present, modifications to the nucleotide structure may be imparted before or after assembly of the polymer. A nucleic acid may be further modified, such as by conjugation with a labeling component.

Engineered nucleic acids are non-naturally occurring nucleic acids and include recombinant nucleic acids and synthetic nucleic acids. "Recombinant nucleic acids" may refer to molecules that are constructed by joining nucleic acid molecules and, in some embodiments, can replicate in a living cell. "Synthetic nucleic acids" may refer to molecules that are chemically or by other means synthesized or amplified, including those that are chemically or otherwise modified but can base pair with naturally occurring nucleic acid molecules. Recombinant and synthetic nucleic acids also include those molecules that result from the replication of either of the foregoing. "Isolated nucleic acids" may refer to nucleic acids of natural, recombinant or synthetic origin, or some combination thereof, which (1) is not associated with the cell in which the "isolated nucleic acid" is found in nature, and/or (2) is operably linked to a nucleic acid to which it is not linked in nature.

A nucleic acid may also encompass single- and double-stranded DNA and RNA, as well as any and all forms of alternative nucleic acid containing modified bases, sugars, and backbones. The term "nucleic acid" thus will be understood to include, but not be limited to, single- or double-stranded DNA or RNA (and forms thereof that can be partially single-stranded or partially double-stranded), cDNA, aptamers, peptide nucleic acids ("PNA"), 2'-5' DNA (a synthetic material with a shortened backbone that has a base-spacing that matches the A conformation of DNA; 2'-5' DNA will not normally hybridize with DNA in the B form, but it will hybridize readily with RNA), and locked nucleic acids ("LNA"). An "oligonucleotide" refers to a short, single-stranded nucleic acid. In some embodiments, an oligonucleotide has a length of less than 200 nucleotides, less than 100 nucleotides, or less than 50 nucleotides. Nucleic acid analogues include known analogues of natural nucleotides that have similar or improved binding, hybridization of base-pairing properties. "Analogous" forms of purines and pyrimidines are well known in the art, and include, but are not limited to aziridinylcytosine, 4-acetylcytosine, 5-fluorouracil, 5-bromouracil, 5-carboxymethylaminomethyl-2-thiouracil, 5-carboxymethylaminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyluracil, 5-methoxyaminomethyl-2-thiouracil, beta-D-mannosylqueosine, 5-methoxyuracil, 2-methylthio-N6-isopentenyladenine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, and 2,6-diaminopurine. DNA backbone analogues provided herein include phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs), methylphosphonate linkages or alternating methylphosphonate and phosphodiester linkages (Strauss-Soukup, 1997, Biochemistry 36:8692-8698), and benzylphosphonate linkages, as discussed in U.S. Pat. No. 6,664,057; see also OLIGONUCLEOTIDES AND ANALOGUES, A PRACTICAL APPROACH, edited by F. Eckstein, IRL Press at Oxford University Press (1991); Antisense Strategies, Annals of the New York Academy of Sciences, Volume 600, Eds. Baserga and Denhardt (NYAS 1992); Milligan, 1993, *J. Med. Chem.* 36:1923-1937; Antisense Research and Applications (1993, CRC Press). The nucleic acids herein can be extracted from cells or synthetically prepared according to any means known to those skilled in the art; for example, the nucleic acids can be chemically synthesized or transcribed or reverse transcribed from cDNA or mRNA, among other sources.

As used herein, two nucleic acids or nucleic acid domains are "complementary" to one another if they base-pair with each other to form a double-stranded nucleic acid molecule. Two nucleic acids or nucleic acid domains are "perfectly complementary" to one another if every nucleotide of one nucleic acid can base-pair with every nucleotide of the other nucleic acid. For example, a domain having the sequence 5'-ATTGCTGACC-3' (SEQ ID NO: 54) is perfectly complementary to a domain having the sequence 5'-GGTCAGCAAT-3' (SEQ ID NO: 55). Herein, complementarity is presumed to be perfectly complementarity unless otherwise indicated. As used herein, two nucleic acids or nucleic acid domains are "partially complementary" to one another when the two domains are not fully complementary but can bind to each other to form an imperfect duplex when the two domains are used, alone or attached to other molecules or moieties. As used herein, an imperfect duplex is nucleic acid duplex disrupted by mismatches, bulges and/or internal loops. As used herein, two nucleic acids or nucleic acid domains have "similar" sequence when more than 74% (e.g., 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%) of the sequence are identical when properly aligned.

A target and/or pseudo-target nucleic acid utilized herein can be any nucleic acid, for example, human nucleic acids, bacterial nucleic acids, or viral nucleic acids. A target and/or pseudo-target nucleic acid sample can be, for example, a nucleic acid sample from one or more cells, tissues, or bodily fluids. Target samples can be derived from any source including, but not limited to, eukaryotes, plants, animals, vertebrates, fish, mammals, humans, non-humans, bacteria, microbes, viruses, biological sources, serum, plasma, blood, urine, semen, lymphatic fluid, cerebrospinal fluid, amniotic fluid, biopsies, needle aspiration biopsies, cancers, tumors, tissues, cells, cell lysates, crude cell lysates, tissue lysates, tissue culture cells, buccal swabs, mouthwashes, stool, mummified tissue, forensic sources, autopsies, archeological sources, infections, nosocomial infections, production sources, drug preparations, biological molecule productions, protein preparations, lipid preparations, carbohydrate preparations, inanimate objects, air, soil, sap, metal, fossils, excavated materials, and/or other terrestrial or extra-terrestrial materials and sources. The sample may also contain mixtures of material from one source or different sources. For example, nucleic acids of an infecting bacterium or virus can be amplified along with human nucleic acids when nucleic acids from such infected cells or tissues are amplified using the disclosed methods. Types of useful target samples include eukaryotic samples, plant samples, animal samples, vertebrate samples, fish samples, mammalian samples, human samples, non-human samples, bacterial samples, microbial samples, viral samples, biological samples, serum samples, plasma samples, blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, crude cell lysate samples, tissue lysate samples, tissue culture cell samples, buccal swab samples, mouthwash samples, stool samples, mummified tissue samples, autopsy samples, archeological samples, infection samples, nosocomial infection samples, production samples, drug preparation samples, biological molecule production samples, protein preparation samples, lipid preparation samples, carbohydrate preparation samples, inanimate object samples, air samples, soil samples, sap samples, metal samples, fossil samples, excavated material samples, and/or other terrestrial or extra-terrestrial samples.

In some embodiments, a target and/or pseudo-target nucleic acid utilized herein comprises repetitive sequence, secondary structure, and/or a high G/C content.

In some embodiments, a target and/or pseudo-target nucleic acid is about 100 to about 1,000,000 nucleotides (nt) or base pairs (bp) in length. In some embodiments, the target and/or pseudo-target nucleic acid is about 100 to about 1000, about 1000 to about 10,000, about 10,000 to about 100,000, or about 100,000 to about 1,000,000 nucleotides in length. In some embodiments, the target and/or pseudo-target nucleic acid is about 100, about 200, about 300, about 400, about 500, about 600, about 700, about 800, about 900, about 1,000, about 2,000, about 3,000, about 4,000, about 5,000, about 6,000, about 7,000, about 8,000, about 9000, about 10,000, about 20,000, about 30,000, about 40,000, about 50,000, about 60,000, about 70,000, about 80,000, about 90,000, about 100,000, about 200,000, about 300,000, about 400,000, about 500,000, about 600,000, about 700,000, about 800,000, about 900,000, or about 1,000,000 nucleotides in length. It is to be understood that the target and/or pseudo-target nucleic acid may be provided in the context of a longer nucleic acid (e.g., such as a coding sequence or gene within a chromosome or a chromosome fragment).

In some embodiments, a target and/or pseudo-target nucleic acid is linear, while in other embodiments, a target and/or pseudo-target nucleic acid is circular (e.g., plasmid DNA, mitochondrial DNA, or plastid DNA).

Applications

The present disclosure may be used, in some embodiments, to detect circulating tumor DNA (ctDNA), which is released from tumor cells (e.g., into circulating blood). Circulating tumor DNA may be distinguished from DNA of the same locus, which is released from normal cells, by the presence of tumor-specific mutations. Thus, in some embodiments, the invention provides methods of detecting circulating tumor DNA, the methods comprising (a) contacting a sample obtained from a subject with an engineered primer that contains a 5' specificity domain (SD) linked to a shorter 3' priming domain (PD), wherein the specificity domain binds to a SD binding site on a target ctDNA from the subject and the priming domain binds to a PD site on the target ctDNA that is upstream of the specificity binding site, and (b) extending the engineered primer at its 3' end in a target-complementary manner in the presence of a polymerase that displaces the specificity domain. In some embodiments, methods comprise amplifying the target nucleic acid bound by the engineered primer. In some embodiments, the target nucleic acid bound by the engineered primer is amplified by polymerase chain reaction.

In some embodiments, the invention provides methods of detecting circulating tumor DNA, the methods comprising (a) contacting a sample obtained from a subject with an engineered primer that contains a specificity domain (SD), a priming domain (PD), and a competitive domain (CD), wherein the SD is linked with PD covalently or non-covalently, and the SD binds to a SD binding site on a target ctDNA strand from the subject and the priming domain binds to a PD site on the target ctDNA strand that is downstream of the SD binding site, and (b) extending the engineered primer at the 3' end of the PD in a target-complementary manner in the presence of a polymerase. In some embodiments, methods comprise amplifying the target nucleic acid using the engineered primer. In some embodiments, the target nucleic acid is amplified by polymerase chain reaction. In some embodiments, the target nucleic acid bound by the engineered primer is amplified by an isothermal nucleic acid amplification reaction.

In some embodiments, the invention provides methods of detecting circulating tumor DNA (ctDNA), the methods comprising contacting a sample obtained from the subject with (a) nondiscriminatory primer that binds to a ctDNA and (b) an engineered partially double-stranded primer that comprises first and second nucleic acid strands arranged into (i) one double-stranded pseudo-target non-specific domain, (ii) one double-stranded pseudo-target specific domain, and (iii) one single-stranded pseudo-target specific domain contributed to by the first nucleic acid strand, wherein the double-stranded pseudo-target non-specific domain has a standard free energy approximately equal to the standard free energy for the single-stranded pseudo-target specific domain bound to a pseudo-target nucleic acid, and wherein the 3' end of the first nucleic acid strand and the 3' of the second nucleic acid strand are non-extendable, and extending the nondiscriminatory primer of (a) at its 3' end in a target-complementary manner in the presence of a polymerase. In some embodiments, the methods comprise amplifying the ctDNA bound by the engineered single-stranded primer of (a). In some embodiments, the ctDNA bound by the engineered single-stranded primer of (a) is amplified by polymerase chain reaction.

In some embodiments, the invention provides methods of detecting circulating tumor DNA (ctDNA), the methods comprising contacting a sample obtained from the subject with (a) nondiscriminatory primer that binds to a ctDNA and (b) an engineered molecular complex comprising one or more molecules arranged into (i) one pseudo-target non-specific interaction pair, (ii) one double-stranded pseudo-target specific duplex, and (iii) one single-stranded pseudo-target specific domain, wherein the pseudo-target non-specific interaction pair comprises two interacting moieties that, when not connected to the rest of the foregoing molecular complex, have a dissociation constant equal to or lower than 10 mM at the condition under which the molecular complex is to be used, and extending the nondiscriminatory primer of (a) at its 3' end in a target-complementary manner in the presence of a polymerase. In some embodiments, the methods comprise amplifying the ctDNA using the nondiscriminatory primer of (a) and engineered molecular complex of (b). In some embodiments, the ctDNA is amplified by polymerase chain reaction. In some embodiments, the ctDNA is amplified by an isothermal amplification reaction.

The invention may be used, in some embodiments, to detect DNA released from donor cells in an organ transplant recipient. Monitoring organ rejection after transplantation requires the detecting and quantification of DNA released from donor cells in an excess background of DNA released from recipient cells. Thus, in some embodiments, the invention provides methods of monitoring organ rejection in a recipient subject after organ transplantation from a donor subject, the methods comprising (a) contacting a sample obtained from the recipient subject with an engineered primer that comprises a 5' specificity domain linked to a shorter 3' priming domain, wherein the specificity domain binds to a specificity binding site on a target donor allele and the priming domain binds to a priming binding site on the target donor allele that is upstream of the specificity binding site, and (b) extending the engineered primer at its 3' end in a target-complementary manner in the presence of a polymerase that displaces the specificity domain. In some embodiments, methods comprise amplifying the target donor allele bound by the engineered primer. In some embodiments, the target donor allele bound by the engineered primer is amplified by polymerase chain reaction.

The invention may be used, in some embodiments, to detect DNA released from donor cells in an organ transplant recipient. Monitoring organ rejection after transplantation requires the detecting and quantification of DNA released from donor cells in an excess background of DNA released from recipient cells. Thus, in some embodiments, the invention provides methods of monitoring organ rejection in a recipient subject after organ transplantation from a donor subject, the methods comprising (a) contacting a sample obtained from the recipient subject with an engineered primer that comprises a specificity domain (SD), a priming domain (PD), and a competitive domain (CD), wherein the SD is linked with PD covalently or non-covalently, the SD binds to a SD site on a target donor allele strand, and the PD binds to a PD binding site on the target donor allele strand that is downstream of the PD binding site, and (b) extending the engineered primer at the 3' end of the PD in a target-complementary manner in the presence of a polymerase. In some embodiments, methods comprise amplifying the target donor allele using the engineered primer of (a). In some embodiments, the target donor allele is amplified by polymerase chain reaction. In some embodiments, the target donor allele is amplified by an isothermal amplification reaction.

In some embodiments, the invention provides methods of monitoring organ rejection in a recipient subject after organ transplantation from a donor subject, the methods comprising contacting a sample obtained from the recipient subject with (a) a nondiscriminatory primer that binds to a target donor allele, and (b) an engineered partially double-stranded primer that comprises first and second nucleic acid strands arranged into (i) one double-stranded recipient allele non-specific domain, (ii) one double-stranded recipient allele specific domain, and (iii) one single-stranded recipient allele specific domain contributed to by the first nucleic acid strand, wherein the double-stranded recipient allele non-specific domain has a standard free energy approximately equal to the standard free energy for the single-stranded recipient allele specific domain bound to a recipient allele nucleic acid, and wherein the 3' end of the first nucleic acid strand and the 3' of the second nucleic acid strand are non-extendable, and extending the engineered single-stranded primer of (a) at its 3' end in a target-complementary manner in the presence of a polymerase. In some embodiments, the methods comprise amplifying the target donor allele bound by the engineered single-stranded primer of (a). In some embodiments, the target donor allele bound by the engineered single-stranded primer of (a) is amplified by polymerase chain reaction.

In some embodiments, the invention provides methods of monitoring organ rejection in a recipient subject after organ transplantation from a donor subject, the methods comprising contacting a sample obtained from the recipient subject with (a) a nondiscriminatory primer that binds to a target donor allele, and (b) an engineered molecular complex comprising one or more molecules arranged into (i) one pseudo-target non-specific interaction pair, (ii) one double-stranded pseudo-target specific duplex, and (iii) one single-stranded pseudo-target specific domain, wherein the pseudo-target non-specific interaction pair comprises two interacting moieties that, when not connected to the rest of the foregoing molecular complex, have a dissociation constant equal to or lower than 10 mM at the condition under which the molecular complex is to be used, and extending the nondiscriminatory primer of (a) at its 3' end in a target-complementary manner in the presence of a polymerase. In some embodiments, the methods comprise amplifying the target donor using the nondiscriminatory primer of (a) and the engineered molecular complex of (b). In some embodiments, the target donor allele is amplified by polymerase chain reaction. In some embodiments, the target donor allele is amplified by an isothermal amplification reaction.

The invention may be used, in some embodiments, to detect the presence of drug-resistant microorganisms in a sample, which requires the detection and quantification of nucleic acids from drug-resistant microorganisms in an background of nucleic acids from drug-sensitive counterparts. Thus, in some embodiments, the invention provides methods of detecting nucleic acids from drug-resistant microorganisms, the methods comprising (a) contacting a sample of microorganisms with an engineered primer that comprises a 5' specificity domain linked to a shorter 3' priming domain, wherein the specificity domain binds to a specificity binding site on a target nucleic acid from a drug-resistant microorganism and the priming domain binds to a priming binding site on the target nucleic acid that is upstream of the specificity binding site, and (b) extending the engineered primer at its 3' end in a target-complementary manner in the presence of a polymerase that displaces the specificity domain. In some embodiments, methods comprise amplifying the nucleic acid bound by the engineered primer. In some embodiments, the target nucleic acid bound by the engineered primer is amplified by polymerase chain reaction.

The invention may be used, in some embodiments, to detect the presence of drug-resistant microorganisms in a sample, which requires the detection and quantification of nucleic acids from drug-resistant microorganisms in an background of nucleic acids from drug-sensitive counterparts. Thus, in some embodiments, the invention provides methods of detecting nucleic acids from drug-resistant microorganisms, the methods comprising (a) contacting a sample of microorganisms with an engineered primer that comprises a specificity domain (SD), a priming domain (PD), and a competitive domain (CD), wherein the SD is linked with PD covalently or non-covalently, the SD binds to a SD binding site on a target nucleic acid from a drug-resistant microorganism and the PD binds to a PD binding site on the target nucleic acid that is downstream of the SD binding site, and (b) extending the PD of the engineered primer at its 3' end in a target-complementary manner in the presence of a polymerase. In some embodiments, methods comprise amplifying the nucleic acid using the engineered primer. In some embodiments, the target nucleic acid is amplified by polymerase chain reaction. In some embodiments, the target nucleic acid is amplified by an isothermal amplification reaction.

In some embodiments, the invention provides methods of detecting nucleic acids from drug-resistant microorganisms, the methods comprising contacting a sample of microorganisms with (a) a nondiscriminatory primer that binds to a target nucleic acid from a drug-resistant microorganism, and (b) an engineered partially double-stranded primer that comprises first and second nucleic acid strands arranged into (i) one double-stranded drug-sensitive-target non-specific domain, (ii) one double-stranded drug-sensitive-target specific domain, and (iii) one single-stranded drug-sensitive-target specific domain contributed to by the first nucleic acid strand, wherein the double-stranded drug-sensitive-target non-specific domain has a standard free energy approximately equal to the standard free energy for the single-stranded drug-sensitive-target specific domain bound to a drug-sensitive-target nucleic acid, and wherein the 3' end of the first nucleic acid strand and the 3' of the second nucleic acid strand are non-extendable, and extending the engineered single-stranded primer of (a) at its 3' end in a target-complementary manner in the presence of a polymerase. In some embodiments, the methods comprise amplifying the target nucleic acid bound by the engineered single-stranded primer of (a). In some embodiments, the target nucleic acid bound by the engineered single-stranded primer of (a) is amplified by polymerase chain reaction.

In some embodiments, the invention provides methods of detecting nucleic acids from drug-resistant microorganisms, the methods comprising contacting a sample of microorganisms with (a) a nondiscriminatory primer that binds to a target nucleic acid from a drug-resistant microorganism, and (b) an engineered molecular complex comprising one or more molecules arranged into (i) one pseudo-target non-specific interaction pair, (ii) one double-stranded pseudo-target specific duplex, and (iii) one single-stranded pseudo-target specific domain, wherein the pseudo-target non-specific interaction pair comprises two interacting moieties that, when not connected to the rest of the foregoing molecular complex, have a dissociation constant equal to or lower than 10 mM at the condition under which the molecular complex is to be used, and extending the nondiscriminatory primer of (a) at its 3' end in a target-complementary manner in the presence of a polymerase. In some embodiments, the methods comprise amplifying the target nucleic acid using the nondiscriminatory primer of (a) and the engineered molecular complex of (b). In some embodiments, the target nucleic acid is amplified by polymerase chain reaction. In some embodiments, the target nucleic acid is amplified by an isothermal amplification reaction.

In some embodiments, the sample is a tissue sample or a biological fluid sample such as, for example, a blood (e.g., plasma or serum) sample, saliva sample, or a urine sample. Other biological samples may be used in accordance with the invention and are described elsewhere herein.

In some embodiments, the microorganisms are bacterial cells such as, for example, *Escherichia coli* cells.

Compositions

In various other aspects, the invention provides compositions comprising a ssPrimer and/or a dsBlocker. In some embodiments, the compositions comprise a ssPrimer and/or a dsBlocker, polymerase, dNTPs, buffers, salts, or a combination of any two or more of the foregoing.

In some embodiments, provided herein are compositions comprising a ssPrimer of the invention, a target nucleic acid and polymerase. In some embodiments, provided herein are compositions comprising a ssPrimer of the invention, a target nucleic acid and a pseudo-target nucleic acid. In some embodiments, provided herein are compositions comprising a ssPrimer of the invention, a target nucleic acid, a pseudo-target nucleic acid and polymerase.

In other embodiments, provided herein are compositions that comprise a dsBlocker of the invention, a target nucleic acid and polymerase. In some embodiments, provided herein are compositions comprising a dsBlocker of the invention, a target nucleic acid and a pseudo-target nucleic acid. In some embodiments, provided herein are compositions comprising a dsBlocker of the invention, a target nucleic acid, a pseudo-target nucleic acid and polymerase. In some embodiments, provided herein are compositions comprising a dsBlocker of the invention, a single-stranded primer that binds to a target nucleic acid, the target nucleic acid, and polymerase. In some embodiments, provided herein are compositions comprising a dsBlocker of the invention, a single-stranded primer that binds to a target nucleic acid, the target nucleic acid and a pseudo-target nucleic acid. In some embodiments, provided herein are compositions comprising a dsBlocker of the invention, a single-stranded primer that binds to a target nucleic acid, the target nucleic acid, a pseudo-target nucleic acid and polymerase.

In some embodiments, the compositions comprise a nucleic acid bound to an engineered single-stranded primer that comprises a 5' specificity domain linked to a 3' priming domain, wherein the specificity domain is bound to a specificity domain binding site on the target nucleic acid and the priming domain is bound to a priming domain binding site on the target nucleic acid that is upstream of the specificity binding site.

In some embodiments, the compositions comprise a nucleic acid bound to (a) a nondiscriminatory primer and (b) a blocker strand comprising an initial toehold domain, a branch migration domain and a balancing toehold domain, wherein or optionally wherein the 3' end of the blocker strand is non-extendable.

The invention also contemplates compositions that comprise any two or more of the reagents described herein.

Kits

In various other aspects, the invention provides kits comprising a ssPrimer and/or a dsBlocker. In some embodiments, the kits comprise a ssPrimer and/or a dsBlocker, polymerase, dNTPs (e.g., dATP, dTTP, dCTP, dGTP), buffers, salts, or a combination of any two or more of the foregoing.

The invention also contemplates kits that comprise any two or more of the reagents described herein, optionally packaged/wrapped in a container.

ssPrimers of the present disclosure include, in some embodiments, a competitive domain (CD) that is designed to cancel some of the entropy change of the reaction of target strand binding to SD. Such entropy cancellation surprisingly expands the acceptable range of reaction conditions. As a result, ssPrimer can effectively enrich a rare target allele even though the ssPrimer sans the CD fails to do so (see Example 2).

dsBlockers of the present disclosure include a protector strand that is designed to cancel some of the entropy change of the reaction of target strand binding to the blocker strand. Such entropy cancellation surprisingly expands the acceptable range of reaction conditions. As a result, dsBlocker that has a (IT-BM) domain of as long as 40 nt (see Example 6) can effectively enrich a rare target allele at the annealing temperature >10° C. lower than the annealing temperature of the target:IT-BM duplex.

Additional Embodiments

The embodiments described in the following numbered paragraphs are also contemplated herein:

1. Methods, comprising contacting a pool of target and pseudo-target nucleic acids with an engineered single-stranded primer that comprises a 5' specificity domain linked to a 3' priming domain, wherein the specificity domain binds to a specificity domain binding site on the target nucleic acid and the priming domain binds to a priming domain binding site on the target nucleic acid that is upstream of the specificity domain binding site, and extending the engineered single-stranded primer at its 3' end in a target-complementary manner in the presence of a polymerase that displaces the specificity domain of the engineered primer from the target nucleic acid.

2. The method of paragraph 2, wherein the polymerase is Vent polymerase, Bsm polymerase, Bst polymerase, Csa polymerase or 96-7 polymerase.

3. The method of paragraph 2 or 3, wherein the engineered single-stranded primer comprises a deoxyribonucleic acid (DNA), a ribonucleic acid (RNA), a locked nucleic acid (LNA), a peptide nucleic acid (PNA) and/or a morpholino.

4. The method of any one of paragraphs 1-3, wherein the specificity domain and the priming domain are linked to each other through a 5'-3' linkage.

5. The method of any one of paragraphs 1-3, wherein the specificity domain and the priming domain are linked to each other through a 5'-5' linkage.

6. The method of paragraph 5, wherein the 3' end of the specificity domain comprises a blocking moiety.

7. The method of any one of paragraphs 1-6, wherein the primer is a contiguous sequence with a non-extendable nucleotide located between the specificity domain and the priming domain.

8. The method of any one of paragraphs 1-7, wherein the non-extendable nucleotide is a non-naturally occurring nucleotide or a dideoxy nucleotide.
9. The method of any one of paragraphs 1-8, wherein the non-naturally occurring nucleotide is isoC, isoG or deoxyuridine.
10. The method of any one of paragraphs 1-9, wherein the specificity domain and the priming domain are linked through a chemical linker.
11. The method of paragraph 10, wherein the chemical linker is polyethylene glycol, an alkyl spacer, a PNA, or a LNA.
12. The method of any one of paragraphs 1-9, wherein the specificity domain and the priming domain are chemically conjugated to each other.
13. The method of paragraph 12, wherein the specificity domain and the priming domain are chemically conjugated to each other by azide-alkyne Huisgen cycloaddition.
14. The method of any one of paragraphs 1-9, wherein the specificity domain and the priming domain are linked to each other by hybridization to a single-stranded oligonucleotide or by hybridization to each other.
15. The method of any one of paragraphs 1-14, wherein the priming domain is shorter than the specificity domain.
16. The method of any one of paragraphs 1-15, wherein the specificity domain forms a hairpin structure.
17. The method of any one of paragraphs 1-16, wherein the specificity domain is partially double-stranded.
18. The method of any one of paragraphs 1-17, wherein the target nucleic acid is single-stranded.
19. The method of any one of paragraphs 1-18, wherein the target nucleic acid is DNA or RNA.
20. The method of any one of paragraphs 1-19, wherein the target nucleic acid is present in a single copy or in low copy.
21. The method of any one of paragraphs 1-20, wherein the target nucleic acid comprises at least one mutation relative to its wild-type counterpart nucleic acid.
22. The method of paragraph 21, wherein the target nucleic acid comprises a single nucleotide polymorphism (SNP).
23. The method of any one of paragraphs 1-22, wherein the method further comprises amplifying the nucleic acid bound to the engineered primer.
24. The method of paragraph 23, wherein the nucleic acid bound by the engineered primer is amplified by polymerase chain reaction.
25. A method, comprising: contacting a pool of target and pseudo-target nucleic acids with (a) nondiscriminatory primer that binds to the target nucleic acid, and (b) an engineered partially double-stranded nucleic acid that comprises first and second nucleic acid strands arranged into (i) one double-stranded pseudo-target non-specific domain, (ii) one double-stranded pseudo-target specific domain, and (iii) one single-stranded pseudo-target specific domain contributed to by the first nucleic acid strand, wherein the double-stranded pseudo-target non-specific domain has a standard free energy approximately equal to the standard free energy for the single-stranded pseudo-target specific domain bound to a pseudo-target nucleic acid, and wherein the 3' end of the first nucleic acid strand and the 3' of the second nucleic acid strand are non-extendable; and extending the nondiscriminatory primer of (a) at its 3' end in a target-complementary manner in the presence of a polymerase.
26. The method of paragraph 25, wherein the first nucleic acid strand and/or the second nucleic acid strand comprises a non-extendable nucleotide at its 3' end.
27. The method of paragraph 25, wherein the non-extendable nucleotide is a non-naturally occurring nucleotide or a dideoxy nucleotide.
28. The method of any one of paragraphs 25-27, wherein the non-naturally occurring nucleotide is isoC, isoG or deoxyuridine.
28. The method of any one of paragraphs 25-28, wherein the nondiscriminatory primer primer of (a) is about 4-35 nucleotides in length.
30. The method of any one of paragraphs 25-29, wherein the double-stranded pseudo-target non-specific domain of (b) is about 4-21 nucleotides in length.
31. The method of any one of paragraphs 25-30, wherein the single-stranded pseudo-target specific domain of (b) is about 4-20 nucleotides in length.
32. The method of any one of paragraphs 25-31, wherein the first and second nucleic acid strands contain a deoxyribonucleic acid (DNA), a ribonucleic acid (RNA), a locked nucleic acid (LNA), a peptide nucleic acid (PNA) and/or a morpholino.
33. The method of any one of paragraphs 25-32, wherein the target nucleic acid is present in a single copy or in low copy.
34. The method of any one of paragraphs 25-32, wherein the target nucleic acid contains at least one mutation relative to its wild-type counterpart.
35. The method of any one of paragraphs 25-34, wherein the target nucleic acid contains a single nucleotide polymorphism (SNP).
36. The method of any one of paragraphs 25-35, wherein the method further comprises amplifying the target nucleic acid bound by the nondiscriminatory primer of (a).
37. The method of paragraph 36, wherein the target nucleic acid bound by the nondiscriminatory primer of (a) is amplified by polymerase chain reaction.
38. A nucleic acid bound to an engineered single-stranded primer that comprises a 5' specificity domain linked to a 3' priming domain, wherein the specificity domain is bound to a specificity domain binding site on the target nucleic acid and the priming domain is bound to a priming domain binding site on the target nucleic acid that is upstream of the specificity domain binding site.
39. A nucleic acid bound to (a) a nondiscriminatory primer and (b) a blocker strand comprising an initial toehold domain, a branch migration domain and a balancing toehold domain, wherein or optionally wherein the 3' end of the blocker strand is non-extendable.
40. An oligonucleotide or a set of oligonucleotides, comprising: (a) a first domain that binds to a first region of the target strand, (b) a second domain that binds to a second region of the target strand, (c) a third domain whose sequence is complementary, partially complementary, identical or similar to a part of the entirety of the first domain, wherein: (i) the said second region is downstream of the said first region on the target strand, (ii) the said second domain comprises a 3'-end that can be extended by a polymerase, and (iii) the first domain and the second domain are connected by covalent or non-covalent interaction.
41. The oligonucleotide or a set of oligonucleotides of paragraph 40, wherein the first region contains a polymorphism.
42. The oligonucleotide or a set of oligonucleotides of paragraph 40, wherein the first domain and the second domain are linked covalently.
43. The oligonucleotide or a set of oligonucleotides of paragraph 40, wherein the first domain and the second domain are linked non-covalently.

44. The oligonucleotide or a set of oligonucleotides of paragraph 43, wherein the non-covalent interaction between the first domain and the second domain is nucleic acid hybridization.
45. The oligonucleotide or a set of oligonucleotides of paragraph 40, wherein the sequence of third domain is identical or similar to a part of the entirety of the sequence of the first domain.
45. The oligonucleotide or a set of oligonucleotides of paragraph 40, wherein the third domain is connected to an additional domain that is complementary to an additional region of the target strand.
46. The oligonucleotide or a set of oligonucleotides of paragraph 40, wherein the third domain is complementary or partially complementary to a part of the entirety of the first domain.
47. The oligonucleotide or a set of oligonucleotides of paragraph 46, wherein the first domain is attached to a first chemical moiety, the second domain is attached to a second chemical moiety, and the first chemical moiety interacts with the second chemical moiety.
48. An oligonucleotide or a set of oligonucleotides of paragraph 47, wherein the interaction between the first moiety and the second moiety is direct.
49. An oligonucleotide or a set of oligonucleotides of paragraph 47, wherein the interaction between the first moiety and the second moiety is indirect.
50. An oligonucleotide or a set of oligonucleotides of paragraph 47, wherein the interaction between the first moiety and the second moiety comprises both direct interaction and indirect interaction.
51. An oligonucleotide or a set of oligonucleotides of paragraph 47, wherein the first moiety and the second moiety are complementary or partially complementary nucleic acids.

EXAMPLES

Example 1 ssPrimer Nucleic Acid Amplification

To determine whether a specificity domain (SD) can help stabilize the binding of the priming domain (PD) to the template, an SD having a length of 20 nucleotides and a PD having a length of 15 nucleotides was used. The linker between the two domains was eight thymidine nucleotides followed by a triethylene glycol moiety. The sequence of the foresight primer was 5'-GCTATCGGCA-CAAATAGCGTTTTTTTTT/iSp9/ATGGA-TAAGAAATAC-3' (SEQ ID NO:6). The ssPrimer of the invention was used as a forward primer in the PCR reactions where a regular primer (sequence: 5'-ACCTTATAT-TCATCAGTGATCACCG-3'; SEQ ID NO:7) was used as the reverse primer. To study how linker length affects yield of an amplification product using the ssPrimer, three oligonucleotides were as the templates in separate polymerase chain reactions (PCRs) (Table 1)

TABLE 1

Oligonucleotide templates

| Oligonucleotide template | 5'-3' | linker |
|---|---|---|
| Template 1 | ATG GAT AAG AAA TAC TCA ATA GGC TTA GCT ATC GGC ACA AAT AGC GTC GGA TGG GCG GTG ATC ACT GAT GAA TAT AAG GT (SEQ ID NO: 8) | none |
| Template 2 | ATG GAT AAG AAA TAC ttttt TCA ATA GGC TTA GCT ATC GGC ACA AAT AGC GTC GGA TGG GCG GTG ATC ACT GAT GAA TAT AAG GT (SEQ ID NO: 9) | 5 thymidines (lowercase) |
| Template 3 | ATG GAT AAG AAA TAC ttttt ttttt TCA ATA GGC TTA GCT ATC GGC ACA AAT AGC GTC GGA TGG GCG GTG ATC ACT GAT GAA TAT AAG GT (SEQ ID NO: 10) | 10 thymidines (lowercase) |

A 8-kb plasmid containing the sequence of Template 1 was also used as the template in a separate PCR. The PCRs were set up as follows. The concentration of each primer was 400 nM. The concentration of the template was 1.25 pM (if oligonucleotide was used as the template) or 4 pg/µL (if plasmid was used as the template). The volume of each PCR reaction was 40 µL. Each reaction contained 2 units (U) of Taq DNA polymerase (New England Biolabs, Ipswich, Mass.) and 1× Standard Taq Buffer (New England Biolabs, Ipswich, Mass.) supplemented with 200 nM of each dNTP. The following thermocycling program was used for the reactions: (1) 95° C., 3 min; (2) 95° C., 15 s; (3) 50° C., 45 s; (4) 72° C., 15 s; (5) Goto (2) for 34 additional cycles; and (6) 4° C., hold.

Figure 9:
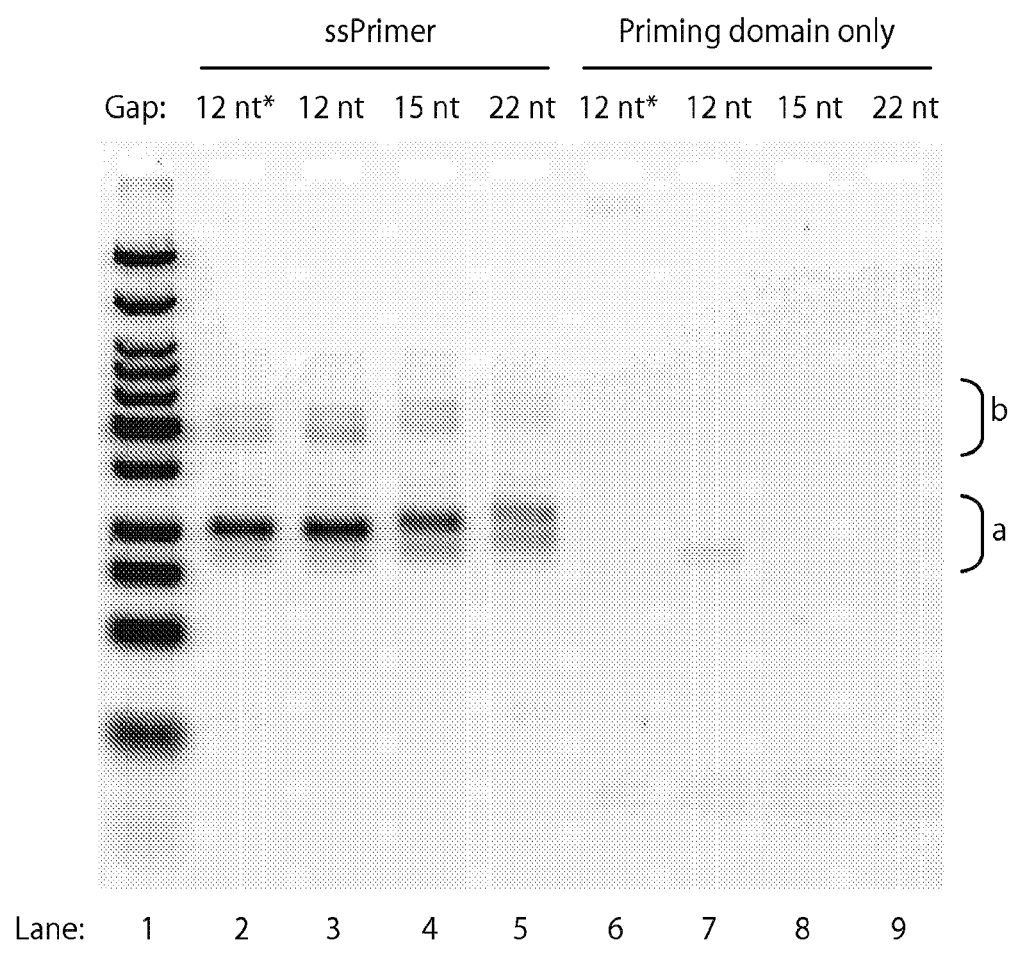
FIG. 9 shows an image of an agarose electrophoresis gel demonstrating the feasibility of a ssPrimer PCR. Lane 1: Low molecular weight ladder (New England Biolabs, Ipswich, Mass.). Lanes 2 to 5: PCR reactions using ssPrimer (i.e., priming domain+linker+specificity domain) as the forward primer. Lanes 6 to 9: PCR reactions using "priming domain+linker" (without the specificity domain) as the forward primer. Plasmid was used as templates.

Two groups of products were observed (groups "a" and "b" in FIG. 9). The strong upper bands of group "a" represent the double-stranded product containing the full-length ssPrimers. The weak lower bands of group "a" may represent amplified product without an SD, as this domain may be degraded by the 5'-to-3' exonuclease activity of Taq. The amplified products of group "b" appear to be dimers of correct PCR product due to fact that some primers form 5'-to-5' linkage spontaneously during synthesis.

As a control, a primer containing only the PD and the linker (sequence: 5'-TTTTTTTT/iSp9/ATGGA-TAAGAAATAC-3'; SEQ ID NO:11) was used in place of the ssPrimer in an identical set of reactions. As shown in FIG. 9, using the ssPrimer yielded products of expected size, and the primer containing only the PD and the linker yielded little or no product.

Example 2 ssPrimer-Based Rare Allele Enrichment

Three species of dsDNA template, named dsWT, dsMut, and dsMutIns, were prepared. Portions of the sequences of these dsDNA templates are shown in Table 2. dsWT and dsMut differ by 1 base pair at position 50 of the shown sequence. dsMutIns represents dsMut with an additional stretch of sequence TTTTACTTTACTTTA (SEQ ID NO: 44) (on the sense strand) inserted between position 108 and 109 of the shown sequence. This insertion serves as a marker for differentiating the amplification products of dsWT/dsMut and dsMutIns on electrophoresis-based analyses. All three dsDNA have short (<200-bp) flaking sequences at the 5' and 3' of the sequences shown in Table 2, but these flanking sequences, as well as the insertion sequence TTTTACTTTACTTTA (SEQ ID NO: 45), are not expected to significantly interact with any oligonucleotide provided in the reactions.

Two template mixtures, named TM1 and TM2, were prepared. TM1 contained dsWT at about 20,000 copies per microliter and dsMutIns at about 200 copies per microliter. TM2 contained dsMut at about 20,000 copies per microliter and dsMutIns at about 200 copies per microliter.

Three versions of ssPrimer (or construct similar to ssPrimer as controls), named ssPrimerA, ssPrimerB, and ssPrimerC were designed.

The ssPrimerB is an example of the design shown in FIG. 2C, bottom-right. In ssPrimerB, the SD is part of strand SD17t16, which has the following sequence: 5'-TTGAGAATGGATTAAGTCAACCTCAtCTTTATT TTTTGGGCgGGCCAAAC ctctacttcatacacc/3InvdT/-3' (SEQ ID NO: 12), where the segment with the sequence "TTTTGGGCgGGCCAAAC" (SEQ ID NO: 46) functions as the SD, the segment with the sequence "ctctacttcatacacc" functions as the AM, the segment with the sequence "TTGAGAATGGATTAAGTCAACCTCA" (SEQ ID NO: 47) functions as the HD, the segment with the sequence "tCTTTATT" functions as a linker between HD and SD, and the moiety '/3InvdT/' is a 3' inverted dT modification that prevents SD17t16 from being extended at the 3' end. In ssPrimerB, the PD is part of the strand PD13, which as the following sequence: 5'-TGAGGTTGACTTAATCCATTCT-CAA/iSp18//iSp18/aacgtactggtga-3' (SEQ ID NO: 13), where the segment with the sequence "TGAGGTTGACT-TAATCCATTCTCAA" (SEQ ID NO: 48) functions as the HD*, the segment with the sequence "aacgtactggtga" (SEQ ID NO: 57) functions as the PD, and the moiety '/iSp18//iSp18/' is an ethylene glycol linker that prevents the DNA polymerase from copying past the PD when the extension production of PD13 serves as the template in the ensuring cycles of PCR. In ssPrimerB, the CD is part of the strand CD_At15c6, which as the following sequence: 5'-gtgtat-gaagtagag GTTTGG/3InvdT/-3' (SEQ ID NO: 49), where the segment with the sequence "GTTTGG" (SEQ ID NO: 50) serves as the CD and the segment with the sequence "gtgtatgaagtagag" (SEQ ID NO: 51) serves as the AM*. As a control of ssPrimerB, ssPrimerA lacks the CD_At15c6 strand but is otherwise identical to ssPrimerB.

The ssPrimerC is an example of the design shown in FIG. 2C, bottom-left. In ssPrimerC, the SD is part of the strand SD16, which has the following sequence: 5'-TTGAGAATG-GATTAAGTCAACCTCAtCTTTATT ttttgggCgGgccaaa/3InvdT/-3' (SEQ ID NO: 14), where the segment with the sequence "TTGAGAATGGATTAAGTCAA CCTCA" (SEQ ID NO: 52) functions as the HD, the segment with the sequence "ttttgggCgGgccaaa" (SEQ ID NO: 56) functions as the SD, and the moiety '/3InvdT/' is a 3' inverted dT modification that prevents SD16 from being extended at the 3' end. In ssPrimerC, the PD is part of the strand PD13, as described above. In ssPrimerC, the CD is part of the strand CD_Bc8t6, which as the following sequence: 5'-TGgccaaa ctgctg/3InvdT/-3' (SEQ ID NO: 53), where the entire sequence functions as the CD and is fully complementary to the pseudo-target (rather than the target), the segment with the sequence "TGgccaaa" is complementary to the CSOR of the pseudo-target strand and partially complementary to the CSOR of the target strand.

In a series of PCR reactions (named A1, B1, and C1), the ssPrimer variants were used as the forward primer to enrich the dsMutIns in the mixture TM1. Similar reactions (named A2, B2, and C2) using TM2 as the template were carried out to provide size markers. In all reactions, two additional oligonucleotides, named RF and RQ, which collectively function as the reverse primer also included in the PCR reactions. RF has the following sequence: 5'-/56-FAM/GCCTGGTCCCTGGTGTCAGGAAA-3' (SEQ ID NO: 15), where the '/56-FAM/' is a fluorescein-based fluorophore. RQ has the following sequence: 5'-CACCAGGGAC-CAGGC/3IABkFQ/-3' (SEQ ID NO: 16), where the V3IABkFQ/' is an Iowa Black quencher. The design of RF and RQ allows the amplification kinetics to be followed in real time (see Example 4).

Each reaction contained 1 unit (U) of Pfu(exo-) DNA polymerase (Agilent) and 1× Standard Taq Buffer (New England Biolabs, Ipswich, Mass.) supplemented with 200 nM of each dNTPs and 5 mM MgSO$_4$.

The ssPrimerA was tested in Reactions A1 and A2. These reactions contained the following oligonucleotides: SD17t16 at a final concentration of 100 nM, PD13 at a final concentration of 120 nM, RF at a concentration of 100 nM, and RQ as a final concentration of 200 nM. One microliter of TM1 and TM2 were added to Reactions A1 and A2, respectively, as the template mixture. The final volumes of Reactions A1 and A2 was both 20 microliters.

The ssPrimerB was tested in Reactions B1 and B2. These reactions contained the following oligonucleotides: SD17t16 at a final concentration of 100 nM, CD_At15c6 at a final concentration of 120 nM, PD13 at a final concentration of 120 nM, RF at a concentration of 100 nM, and RQ as a final concentration of 200 nM. One microliter of TM1 and TM2 were added to Reactions B1 and B2, respectively, as the template mixture. The final volumes of Reactions B1 and B2 were both 20 microliters.

The ssPrimerC was tested in Reactions C1 and C2. These reactions contained the following oligonucleotides: SD16 at a final concentration of 100 nM, CD_Bc8t6 at a final concentration of 120 nM, PD13 at a final concentration of 120 nM, RF at a concentration of 100 nM, and RQ as a final concentration of 200 nM. One microliter of TM1 and TM2 were added to Reactions C1 and C2, respectively, as the template mixture. The final volumes of Reactions C1 and C2 were both 20 microliters.

Figure 15:
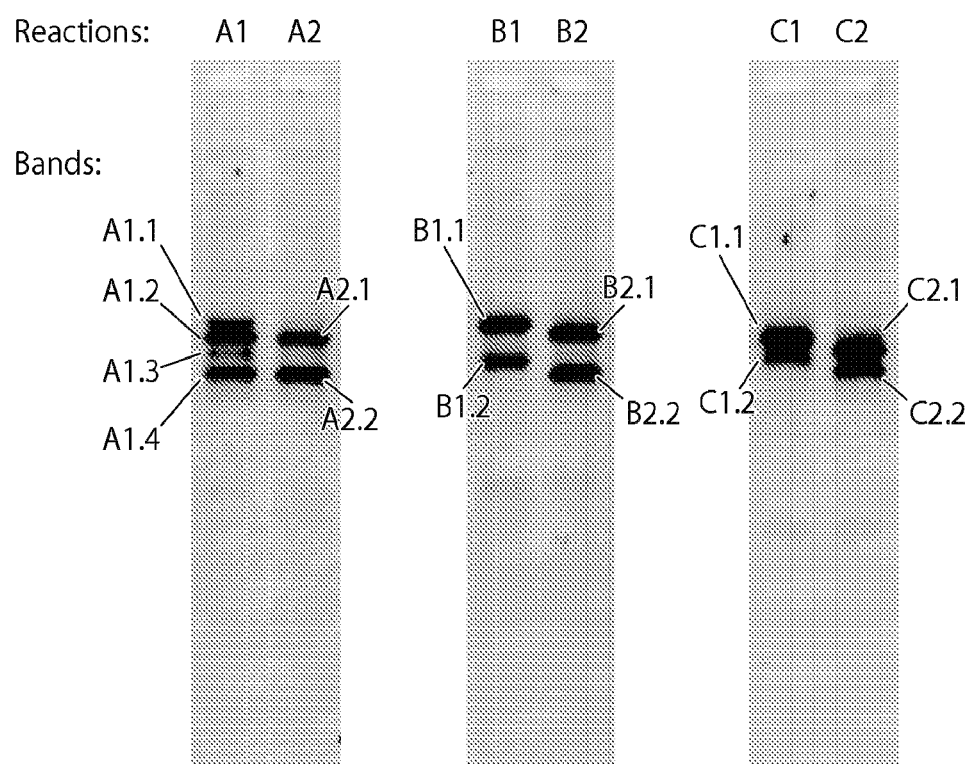
FIG. 15 shows the performance of a ssPrimer.

The reactions were set up on ice and the following thermocycling program was used for the reactions: (1) 95° C., 1 min; (2) 95° C., 15 s; (3) 60° C., 1 min; (4) 70° C., 15 s; (5) 80° C., 15 s; (6) Goto (2) for additional 59 cycles. Five microliters of PCR product were analyzed on 4% agarose gel pre-stained with 1×SYBR Safe (Invitrogen) and the gel image is shown on FIG. 15.

The bands A1.1 and A1.3 represent the amplification products of dsMutIns, and the bands A1.2 and A1.4 represent the amplification products of dsWT. The bands A2.1 and A2.2 represent the amplification products of dsMut, which should have the same mobility as the amplification products of dsWT. The bands A1.1, A1.2, and A2.1 are PCR products with SD17t16 attached; bands A1.3, A1.4, and A2.2 are PCR products without SD17t16 attached; since PD13 was in excess, both groups of complexes are expected to be seen on gel. Similar patterns are seen on other groups of experiments. From the result of Reaction A1 it can be seen that even though the amplification products of the initially rare dsMutIns are visible, the majority of the PCR product were still the initially abundant dsWT, indicating that the enrichment of the rare allele was not effective.

For the results involving ssPrimerB, the bands B1.1 and B1.2 represent the amplification products of dsMutIns; the bands B2.1 and B2.2 represent the amplification products of dsMut, which should have the same mobility as the amplification products of dsWT. Surprisingly, only the amplification products of the initially rare dsMutIns are visible, whereas the amplification products of the initially abundant dsWT are completely invisible, indicating that the enrichment of the rare allele was extremely effective. The difference between Reactions A1 and B1 highlights the importance of the CD.

For the results involving ssPrimerC, the bands C1.1 and C1.2 represent the amplification products of dsMutIns; the bands C2.1 and C2.2 represent the amplification products of dsMut, which should have the same mobility as the amplification products of dsWT. From the result of Reaction C1 it can be seen that only the amplification products of the initially rare dsMutIns are visible, whereas the amplification products of the initially abundant dsWT are invisible, indicating that the enrichment of the rare allele was effective.

caatag-3'; SEQ ID NO: 20) and a reverse primer (5'-taagattttttttgatactgtggcggtctgtatttcccagaaccttg-3'; SEQ ID NO: 21) were designed to amplify a 151-bp PCR amplicon from each plasmids. The amplicon spans the single nucleotide polymorphism between the two plasmids. The antisense strand of the pWT-derived amplicon had the following sequence: 5'-taagattttttttgatactgtggcggtctgtatttcccagaaccttgaacttttagacggaaccttatattcatcagtga tcacCGCCCATC-CGACGCTATTTGTGCCGATA[T]CTAAGCctattgagt-atttcttatccattttgcctc-3' (SEQ ID NO: 22). The antisense strand of the pMut-derived amplicon had the following sequence: 5'taagattttttttgatactgtggcggtctgtatttcccagaaccttgaacttttagacggaaccttatattcatcagt gatcacCGCCCATC-CGACGCTATTTGTGCCGATA[G]CTAAGCctattgagt-atttcttatccattttgcct c-3'(SEQ ID NO: 23). The bases that were different between the two amplicons are enclosed in brackets.

A dsBlocker was designed to block the amplification of the pWT-derived amplicon. The blocker strand had the following sequence: 5'-GCTTAG[A]TATCGGCA-CA|AATAGCGTCGGATGGGCGtcttcttcaaatcggg-3' (SEQ ID NO:24), where the balancing toehold domain is shown in lower case, the initial toehold domain is shown in upper case on the left side of the symbol 'I', and the branch migration domain is shown in upper case on the right side of the symbol 'I'. The nucleotide that differs between the two amplicons is enclosed by brackets. The protector strand had the following sequence: 5'-cccgatttgaagaagaCGCCCATC-CGACGCTATT-3' (SEQ ID NO:25), where the balancing toehold domain and the branch migration domain are shown in lower and upper cases, respectively.

Two separate PCR reactions were carried out, which were identical except for the template (4 ng pWT plasmid in one and 4 ng pMut plasmid in the other). Both reactions contained the following oligonucleotides: 100 nM forward primer, 100 nM reverse primer, 150 nM blocker strand, and 250 nM protector strand. The volume of each PCR reaction

TABLE 2 dsDNA templates

| Name of dsDNA template | Sequence (sense strand, 5'-3') |
|---|---|
| dsWT | Aacgtactggtgaaaacaccgcagcatgtcaagatcacagattttggg CTGgccaaaactgctgggtgcggaagagaaagaataccatgcagaa ggaggcaaagtaaggaggtggctttaggtcagccagcattttcctgac accagggaccaggc (SEQ ID NO: 17) |
| dsMut | Aacgtactggtgaaaacaccgcagcatgtcaagatcacagattttggg CGGgccaaaactgctgggtgcggaagagaaagaataccatgcagaa ggaggcaaagtaaggaggtggctttaggtcagccagcattttcctgac accagggaccaggc (SEQ ID NO: 18) |
| dsMutIns | Aacgtactggtgaaaacaccgcagcatgtcaagatcacagattttggg CGGgccaaaactgctgggtgcggaagagaaagaataccatgcagaa ggaggcaaagtaaggTTTTACTTTACTTTAaggtggcttt aggtcagccagcattttcctgacaccagggaccaggc (SEQ ID NO: 19) |

Example 3 dsBlocker Nucleic Acid Amplification

To demonstrate the efficacy of dsBlocker nucleic acid amplification of the invention, two 8 kb plasmids, pWT and pMut, which differ by one nucleotide base pair, were prepared. A forward primer (5'-gaggcaaaaatggataagaaatactwas 40 µL. Each reaction contained 1 unit (U) of Pfu(exo-) DNA polymerase (Agilent) and 1× Standard Taq Buffer (New England Biolabs, Ipswich, Mass.) supplemented with 200 nM of each dNTPs and 5 mM MgSO$_4$. As controls, two other PCR reactions were used. The controls lacked the blocker and protector strands but were otherwise identical to the other two reactions. The reactions were set up on ice and the following thermocycling program was used for the reactions: (1) 95° C., 1 min; (2) 95° C., 15 s; (3) 35° C., 1 min; (4) 60° C., 1 min; and (5) Goto (2) for 7 additional cycles.

Figure 10:
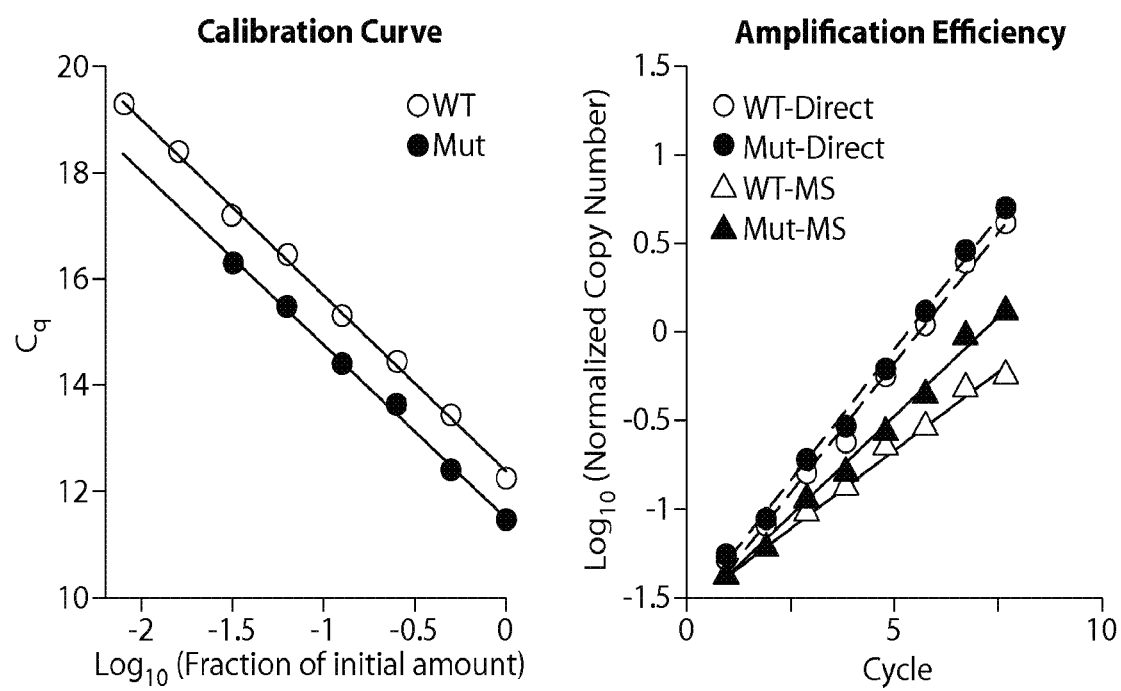
FIG. 10 shows a graph demonstrating preferential amplification of pMut over pWT. Left: Standard curve. Right: Amplication kinetics.

At the end of the 35° C. incubation for each cycle, 2 µL aliquots were taken out from each tube and transferred to another set of tubes on ice. The amount of amplicon in these aliquots were quantified using the QuantiFast SYBR® Green kit and the following two primers: 5'-gaggcaaaaatg-gataagaaatactcaatag-3'(SEQ ID NO:26) and 5'-cagaacctt-gaacttttagacgg-3' (SEQ ID NO:27). A calibration curve was obtained by serial dilution (FIG. 10, left). The results (FIG. 10, right) of qPCR showed that without the dsBlocker, both pWT and pMut were amplified with ~93% priming efficiency. In the presence of the dsBlocker, pWT was amplified with 47% priming efficiency, while pMut was amplified with 65% efficiency. Thus, for each round of PCR, the pMut was preferentially amplified by a factor of 1.65/1.47=1.12. It can be expected that after 30 cycles of dsBlocker nucleic acid amplification (assuming amplification is always exponential), pMut will be preferentially amplified with a factor of $1.12^{30}$=30.

The modest selectivity is a result of the weak duplex-disrupting effect of the A:G mis-match compared to an A:T match. Most mismatches should result in selectivity between 10,000 to 100,000 after 30 cycles of dsBlocker nucleic acid amplification.

Example 4

Real-Time Monitoring of dsBlocker-Based Sequence-Specific PCR Using a Self-Reporting Primer To monitor the amplification progression in real time, essentially the same reaction was performed as in Example 2 using an CFX96 Touch™ Real-Time PCR Detection System (Bio-Rad) with the following modifications. First, the reverse primer was modified by attaching a fluorophore at its 5' end (5'-/FAM/taagatttttttgatactgtggcggtctgtatttccca-gaaccttg-3'; SEQ ID NO:28). Second, an additional quencher-bearing strand (5'-ACCGCCACAGTATCAAAA AAAATCTTA/IowaBlackFQ/-3'; SEQ ID NO:29) that binds to the 27 nucleotides at the 5' end of the reverse primer was introduced. Third, the blocker strand was changed (5'-GCTTAG[C]T ATCGGCACA|AATAGCGTCG-GATGGGCGtcttcttcaaatcggg-3'; SEQ ID NO:30) so that it blocked the amplification of pMut rather than pWT. Fourth, the volume of the reaction was reduced to 20 µL, and the amount of template plasmid was reduced to 10 pg per reaction, while maintaining the concentration of all other reagents. The fluorescent signals were measured at the end of Step 3 (5° C., 1 min) of the thermocycling program.

Figure 11:
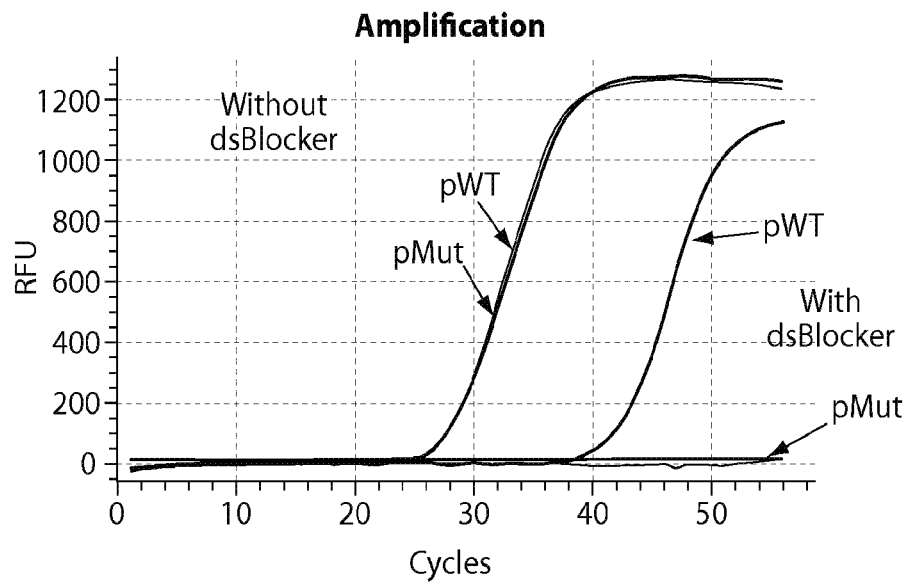
FIG. 11 shows a graph of real-time monitoring of dsBlocker-based sequence specific amplification.

As shown in FIG. 11, without using the dsBlocker, pWT and pMut were amplified with similar efficiency. When dsBlocker targeting pMut was added, the amplification efficiency of pMut was greatly reduced while that of pWT was only modestly reduced. In the presence of the dsBlocker, the ΔCq (difference in the number of cycles required for the fluorescent signal to reach the threshold shown as the horizontal bar) between pMut amplification and pWT amplification was about 16.

Example 5

Enrichment of Rare Allele Using dsBlocker

A mixture of 1% pWT and 99% pMut was made, and 0.1 ng of the mixture was used in two PCR reactions with and without dsBlocker, as described in Example 3. The PCR product was column-purified and subject to Sanger sequencing using a sequencing primer that binds to the sense strand. As shown in the left panel of FIG. 12, without the dsBlocker in the PCR reaction, the 'T' peak indicative of pWT was not unambiguously observed in the chromatogram of the Sanger sequencing, consistent with the fact that pWT was only present in 1% of the mixture and was not enriched during the PCR amplification.

Figure 12:
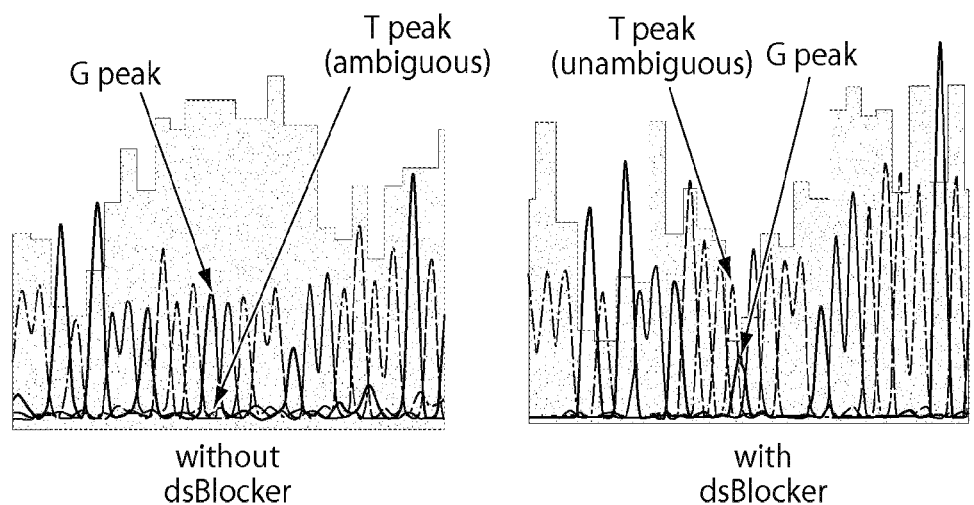
FIG. 12 shows a chromatogram of sequenced PCR products with and without a dsBlocker in the PCR reaction.

By contrast, when dsPseudoPrimer was used in the PCR reaction, pWT was clearly enriched, resulting in an unambiguous 'T' peak in the chromatogram (right panel of FIG. 12).

Example 6

Enrichment of Rare Allele Using dsBlocker and High-Fidelity DNA Polymerase

A dsBlocker was designed to block the amplification of the wild-type sequence of a portion of the exon 20 of the human EGFR gene, and enrich mutant alleles such as the T790M mutant.

The blocker strand had the following sequence: 5'-CT-CATCACGCAGC TCATGCCCTTCGGCTGCCTCCTG-GACT cctgacaccg caaaa/3InvdT/-3' (SEQ ID NO:31), where the segment with sequence "cctgacaccg" (SEQ ID NO: 38) functions as the BT domain, the segment with the sequence "CTCATCACGCAGC" (SEQ ID NO: 39) functions as the IT domain, and the segment with the sequence "TCATGCCCTTCGGCTGCCTCCTGGACT" (SEQ ID NO: 40) functions as the BM domain. The protector strand had the following sequence: 5'-cggtgtcaggAGTCCAG-GAGGCAGCC GAAGGGCATGA aaaa/3InvdT/-3' (SEQ ID NO:32), where the segment with the sequence "cggt-gtcagg" (SEQ ID NO: 41) functions as the BT* domain and the segment with the sequence "AGTCCAGGAGGCAGC-CGAAGGGCATGA" (SEQ ID NO: 42) functions as the BM* domain.

A dsDNA template named gEGFR_E20_MutIns was synthesized. The sense strand of gEGFR_E20_MutIns has the following sequence: 5'-gctgggcatctgcctcacctccaccgtgcagct-catcATGcagctcatgcccttcggctgcctcctggactatgtccgggaaca AATACTTACTATTACTTATA caaagacaatattggctcccagtac-ctgctcaactggtgtgtgcagatcgcaaag gtaatcagggaaggga-3' (SEQ ID NO:33), where the segment with the sequence 'ATG' in upper case contains the T790M mutation, and the segment with the sequence 'AATACTTACTATTACTTATA' (SEQ ID NO: 43) is an insertion of arbitrary sequence so that the amplification product gEGFR_E20_MutIns and the amplification product of the wild-type EGFR can be differentiated in electrophoresis-based analyses. This insertion is not expected to interact with any oligonucleotide used in this example.

Genomic DNA (gDNA) from the cell line HT-29 (ATCC) served as the source of the abundant wild-type allele. Six mixtures were prepared:

Mixture ETM1 contains HT-29 gDNA at 1,000 haploid copies per microliter and no gEGFR_E20_MutIns.

Mixture ETM2 contains HT-29 gDNA at 1,000 haploid copies per microliter and gEGFR_E20_MutIns at 1,000 copies per microliter.

Mixture ETM3 contains HT-29 gDNA at 1,000 haploid copies per microliter and gEGFR_E20_MutIns at 100 copies per microliter.

Mixture ETM4 contains HT-29 gDNA at 10,000 haploid copies per microliter and gEGFR_E20_MutIns at 1,000 copies per microliter.

Mixture ETM5 contains HT-29 gDNA at 10,000 haploid copies per microliter and gEGFR_E20_MutIns at 100 copies per microliter.

Mixture ETM6 contains HT-29 gDNA at 10,000 haploid copies per microliter and gEGFR_E20_MutIns at 10 copies per microliter.

A series of the PCR were set up to enrich the gEGFR_E20_MutIns in each of the mixture described above in the presence of the wild-type EGFR exon 20 sequence from the gDNA. The following oligonucleotide set was used: the blocker strand at a final concentration of 150 nM, the protector strand at a final concentration of 250 nM, the forward primer (5'-TGCACG*G/iSp18/ctcacctccaCCGTGC*A-3', SEQ ID NO:34) at 100 nM and reverse primer (5'-CTCAACTG*G/iSp18/atctgcacacaCCAGTTGA*G-3', SEQ ID NO:35) at 100 nM. In the sequences of forward and reverse primers, symbol * means a phosphorothioate modification between the flanking nucleotides, and the symbol/iSp18/means a hexaethylene glycol linker.

In a series of control experiments, the blocker strand and the protector strand were omitted, i.e., the following oligonucleotide set was used: the forward primer (5'-TGCACG*G/iSp18/ctcacctccaCCGTGC*A-3', SEQ ID NO:36) at 100 nM and reverse primer (5'-CTCAACTG*G/iSp18/atctgcacacaCCAGTTGA*G-3', SEQ ID NO:37) at 100 nM.

All reactions contained 0.4 unit (U) of Hotstart Phusion DNA polymerase (New England Biolabs, Ipswich, Mass.) and 1×HF Buffer (New England Biolabs, Ipswich, Mass.) supplemented with 200 nM of each dNTPs and 2 mM MgSO$_4$. The final volumes of all reactions were 20 microliters.

Figure 16A:
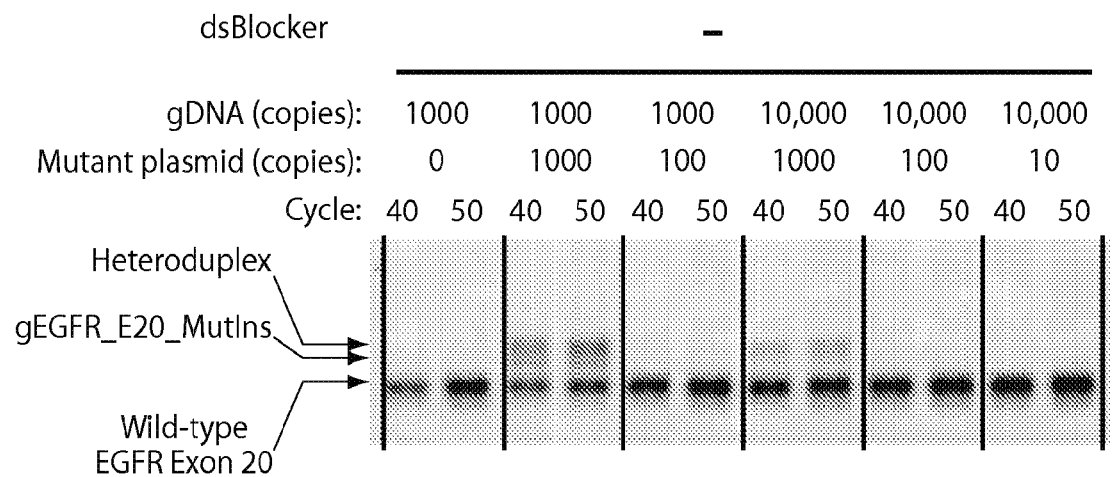
FIGS. 16A and 16B shows the performance of a dsBlocker when used with a high-fidelity DNA polymerase.
Figure 16B:
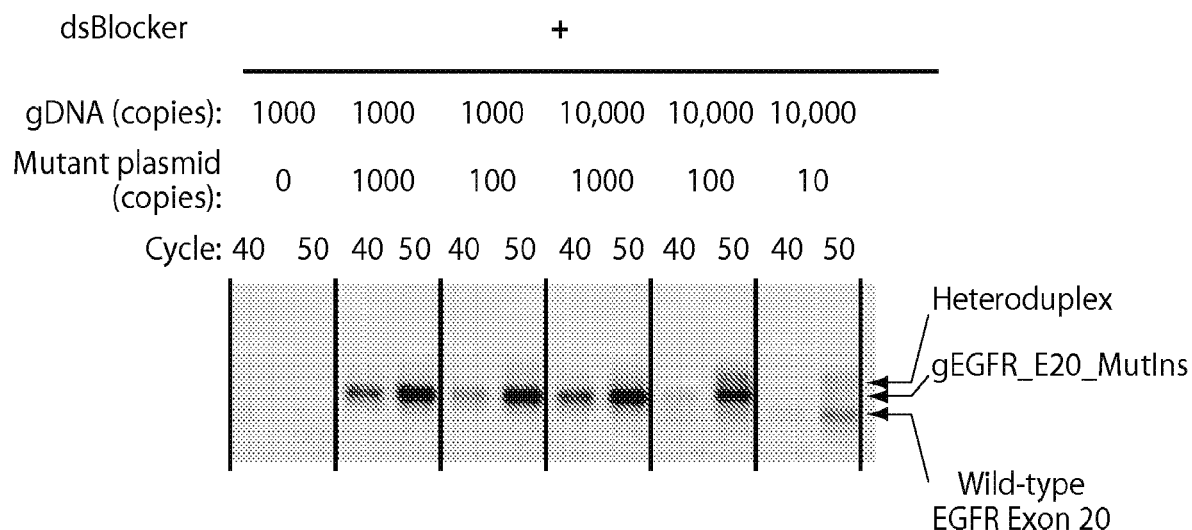

The following PCR program was used: (1) 95° C., 1 min; (2) 95° C., 15 s; (3) 60° C., 1 min; (4) 80° C., 15 s; (5) Goto (2) for 49 additional cycles; (6) 72° C., 2.5 min. After the 40$^{th}$ and the 50$^{th}$ cycles, 2.5 microliter aliquot of each reaction was taken and subject to electrophoresis analysis on a 4% agarose gel prestained with SYBR Safe (Invitrogen). The resulting gel image is shown in FIG. 16. It can be seen that, in the absence of the dsBlocker, only ETM2 and ETM4 yielded bands reflecting the gEGFR_E20_MutIns amplification product; in all reactions the amplification product of the wild-type sequence are the major or only product. In the presence of dsBlocker, however, ETM1, which contained only the gDNA and no gEGFR_E20_MutIns, did not yield visible amplification product, and the amplification product of gEGFR_E20_MutIns was the major product of reactions using ETM2, ETM3, ETM4, and ETM5. Even in ETM6, where mutation allele (i.e., gEGFR_E20_MutIns) is only present in about 0.1% fraction, amplification product of gEGFR_E20_MutIns was still visible. All of these observations were consistent with the expectation that the dsBlocker suppressed the amplification of the wild-type sequence and enriched the T790M mutant sequence.

REFERENCES

[1] H. Gevensleben, I. Garcia-Murillas, M. K. Graeser, G. Schiavon, P. Osin, M. Parton, I. E. Smith, A. Ashworth, and N. C. Turner. Noninvasive Detection of HER2 Amplification with Plasma DNA Digital PCR. Clin. Cancer Res., May 2013.

[2] C. R. Newton, A. Graham, L. E. Heptinstall, S. J. Powell, C. Summers, N. Kalsheker, J. C. Smith, and A. F. Markham. Analysis of any point mutation in DNA. The amplification refractory mutation system (ARMS). Nucleic Acids Res., 17(7):2503-2516, April 1989.

[3] R. S. Cha, H. Zarbl, P. Keohavong, and W. G. Thilly. Mismatch amplification mutation assay (MAMA): application to the c-H-ras gene. PCR Methods Appl., 2(1):14-20, August 1992.

[4] J. R. Dobosy, S. D. Rose, K. R. Beltz, S. M. Rupp, K. M. Powers, M. A. Behlke, and J. A. Walder. RNase H-dependent PCR (rhPCR): improved specificity and single nucleotide polymorphism detection using blocked cleavable primers. BMC Biotechnol., 11:80, 2011.

[5] Q. Liu and S. S. Sommer. Pyrophosphorolysis-activated polymerization (PAP): application to allele-specific amplification. BioTechniques, 29(5):1072-1076, November 2000.

[6] T. Seyama, T. Ito, T. Hayashi, T. Mizuno, N. Nakamura, and M. Akiyama. A novel blocker-PCR method for detection of rare mutant alleles in the presence of an excess amount of normal DNA. Nucleic Acids Res., 20(10): 2493-2496, May 1992.

[7] H. Orum, P. E. Nielsen, M. Egholm, R. H. Berg, O. Buchardt, and C. Stanley. Single base pair mutation analysis by PNA directed PCR clamping. Nucleic Acids Res., 21(23):5332-5336, November 1993.

[8] L. Zhou, R. A. Palais, G. D. Smith, D. Anderson, L. R. Rowe, and C. T. Wittwer. Enrichment and detection of rare alleles by means of snapback primers and rapid-cycle PCR. Clin. Chem., 56(5):814-822, May 2010.

[9] J. Li, L. Wang, H. Mamon, M. H. Kulke, R. Berbeco, and G. M. Makrigiorgos. Replacing PCR with COLD-PCR enriches variant DNA sequences and redefines the sensitivity of genetic testing. Nat. Med., 14(5):579-584, May 2008.

[10] D. Y. Zhang, S. X. Chen, and P. Yin. Optimizing the specificity of nucleic acid hybridization. Nat Chem, 4(3): 208-214, March 2012.

[11] J. SantaLucia and D. Hicks. The thermodynamics of DNA structural motifs. Annu Rev Biophys Biomol Struct, 33:415-440, 2004.

[12] R. M. Dirks, Bois J. S., Schaefer J. M., Winfree E., and N. A. Pierce. Thermodynamic analysis of interacting nucleic acid strands. SIAM Rev, 49(1):65-88, 2007.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition, comprising:
   a pseudo-target nucleic acid and/or a target nucleic acid that comprises a specificity domain binding site and a priming domain binding site that is downstream from the specificity domain binding site; and
   an engineered primer that comprises (a) a specificity domain linked to a priming domain via a linker comprising a non-nucleotide moiety and (b) a competitive domain that binds to the specificity domain of the engineered primer or to the specificity domain binding site of the pseudo-target nucleic acid and/or a target nucleic acid,
   wherein the specificity domain binds to the specificity domain binding site on the target nucleic acid and the priming domain binds to the priming domain binding site that is downstream from the specificity domain binding site on the target nucleic acid.

2. The composition of claim 1 further comprising a polymerase.

3. The composition of claim 2, wherein the polymerase is a DNA polymerase or a reverse transcriptase.

4. The composition of claim 3, wherein the polymerase is a DNA polymerase selected from Vent polymerase, Bsm polymerase, Bst polymerase, Csa polymerase, 96-7 polymerase, and Pfu polymerase.

5. The composition of claim 1, wherein the engineered primer comprises a deoxyribonucleic acid (DNA), a ribonucleic acid (RNA), a locked nucleic acid (LNA), a peptide nucleic acid (PNA) and/or a morpholino.

6. The composition of claim 1, wherein the specificity domain and the priming domain are linked to each other through a 5'-3' linkage or a 5'-5' linkage.

7. The composition of claim 6, wherein the specificity domain comprises a 3' end having a blocking moiety.

8. The composition of claim 1, wherein the priming domain is shorter than the specificity domain.

9. The composition of claim 1, wherein the specificity domain and the competitive domain are covalently linked to each other to form a hairpin structure.

10. The composition of claim 1, wherein the target nucleic acid comprises at least one mutation relative to its wild-type counterpart nucleic acid.

11. The composition of claim 1, wherein the non-nucleotide moiety is a chemical moiety.

12. The composition of claim 11, wherein the chemical moiety is selected from the group consisting of a polyethylene glycol linkage, an alkyl spacer, a PNA linkage or a LNA linkage.

* * * * *